US010799460B2

(12) United States Patent
Saur-Brosch

(10) Patent No.: US 10,799,460 B2
(45) Date of Patent: *Oct. 13, 2020

(54) FORMULATION FOR THE CONTROLLED RELEASE OF ONE OR SEVERAL SUBSTANCES IN THE DIGESTIVE TRACT OF A MAMMAL

(76) Inventor: Roland Saur-Brosch, Heidelberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/343,393

(22) PCT Filed: Sep. 7, 2012

(86) PCT No.: PCT/IB2012/054655
§ 371 (c)(1),
(2), (4) Date: Jun. 16, 2014

(87) PCT Pub. No.: WO2013/035081
PCT Pub. Date: Mar. 14, 2013

(65) Prior Publication Data
US 2014/0302134 A1    Oct. 9, 2014

(30) Foreign Application Priority Data

Sep. 7, 2011   (DE) .................. 10 2011 112 501
Sep. 11, 2011  (DE) .................. 10 2011 112 761
(Continued)

(51) Int. Cl.
*A61K 9/00* (2006.01)
*A61K 9/48* (2006.01)
(Continued)

(52) U.S. Cl.
CPC ............ *A61K 9/4891* (2013.01); *A61K 9/167* (2013.01); *A61K 9/1682* (2013.01);
(Continued)

(58) Field of Classification Search
CPC .. A61K 9/2054; A61K 9/2095; A61K 9/2846; A61K 9/2886; A61K 9/4808;
(Continued)

(56) References Cited

U.S. PATENT DOCUMENTS 6,506,407 B2 * 1/2003 Watanabe ............ A61K 9/2826
424/463
7,288,532 B1 * 10/2007 Payne ................... C08B 37/003
435/101
(Continued)

FOREIGN PATENT DOCUMENTS

DE    1204363 A    11/1965
DE    3812799 A1   10/1989
(Continued)

OTHER PUBLICATIONS

Seipmann et al. (Pharmaceutical Research, 1999, 16(11):1748-1756).*
(Continued)

*Primary Examiner* — Ernst V Arnold

(57) ABSTRACT

The present invention relates to a formulation for the controlled release of active ingredients after the passage of the ileo-cecal-valve, comprising one or more active ingredients or one or more active ingredient containing cores (W), enveloped by one or more envelopments (C), which are dissoluble or permeable above an individual defined pH value and are dissoluble or permeable below another individual defined pH value, again enveloped by an envelopment (E), which is dissoluble or permeable above still another individual defined pH value.

29 Claims, 11 Drawing Sheets

(30) Foreign Application Priority Data

| Dec. 19, 2011 | (DE) | ........................ 10 2011 056 646 |
| Apr. 3, 2012 | (EP) | .................................... 12163560 |
| Apr. 17, 2012 | (EP) | .................................... 12164414 |
| Apr. 30, 2012 | (EP) | .................................... 12166248 |
| May 22, 2012 | (EP) | .................................... 12168985 |
| Jun. 1, 2012 | (EP) | .................................... 12170634 |
| Aug. 14, 2012 | (EP) | .................................... 12180485 |

(51) Int. Cl.
    *A61K 9/28*     (2006.01)
    *A61K 9/50*     (2006.01)
    *A61K 9/16*     (2006.01)
    *A61K 9/20*     (2006.01)
    *A61K 31/167*     (2006.01)
    *A61K 31/196*     (2006.01)
    *A61K 31/573*     (2006.01)
    *A61K 33/24*     (2019.01)
    *A61K 35/741*     (2015.01)
    *A61K 35/00*     (2006.01)

(52) U.S. Cl.
    CPC ............ *A61K 9/2095* (2013.01); *A61K 9/286* (2013.01); *A61K 9/2846* (2013.01); *A61K 9/2886* (2013.01); *A61K 9/4833* (2013.01); *A61K 9/5036* (2013.01); *A61K 9/5042* (2013.01); *A61K 9/5078* (2013.01); *A61K 31/167* (2013.01); *A61K 31/196* (2013.01); *A61K 31/573* (2013.01); *A61K 33/24* (2013.01); *A61K 35/741* (2013.01); *A61K 9/1652* (2013.01); *A61K 9/1676* (2013.01); *A61K 9/2018* (2013.01); *A61K 9/2054* (2013.01); *A61K 9/4858* (2013.01); *A61K 2035/115* (2013.01)

(58) Field of Classification Search
    CPC .. A61K 9/4833; A61K 9/4858; A61K 9/5036; A61K 9/5042; A61K 9/5084; A61K 31/167; A61K 31/573; A61K 35/741; A61K 9/1676; A61K 9/286; A61K 9/4891; A61K 9/5078; A61K 2035/115; A61K 31/135; A61K 31/137; A61K 31/196; A61K 31/513; A61K 31/606; A61K 33/24; H01R 12/714; H01R 13/2435

See application file for complete search history.

(56) References Cited

U.S. PATENT DOCUMENTS

| 2005/0037077 | A1 | 2/2005 | Legrand |
| 2006/0127484 | A1 | 6/2006 | Speirs |
| 2006/0188563 | A1 | 8/2006 | Shuji |
| 2009/0022786 | A1* | 1/2009 | Lee ........................ A61K 9/1676 424/451 |
| 2009/0263340 | A1 | 10/2009 | Ille-Boehler |
| 2010/0209520 | A1 | 8/2010 | Kubo |
| 2012/0141584 | A1* | 6/2012 | Chauhan .............. A61K 9/2072 424/457 |
| 2014/0322316 | A1 | 10/2014 | Saur-Brosch |

FOREIGN PATENT DOCUMENTS

| DE | 69109557 T2 | 9/1995 |
| DE | 69225979 T2 | 12/1998 |
| DE | 19932603 A1 | 1/2001 |
| DE | 69425453 T2 | 4/2001 |
| DE | 69522729 T2 | 7/2002 |
| DE | 69619668 T2 | 10/2002 |
| DE | 69624047 T2 | 8/2003 |
| DE | 69922394 T2 | 12/2005 |
| DE | 69535432 T2 | 12/2007 |
| DE | 60035412 T2 | 3/2008 |
| EP | 1607087 A1 | 12/2005 |
| EP | 1496870 B1 | 9/2009 |
| RU | 2336865 C2 | 10/2008 |
| WO | 95/30422 A1 | 11/1995 |
| WO | 96/36321 A1 | 11/1996 |
| WO | 2004/004696 A1 | 1/2004 |
| WO | 2006/102446 A2 | 9/2006 |
| WO | 2007/006353 A2 | 1/2007 |

OTHER PUBLICATIONS

Aideh et al.(Arch. Pharm. Pharm. Med. Chem. 1999;332:103-107). (Year: 1999).*

Chauhan, Ch. S. et al, Formulation and evaluation of Prednisolone tablet for colon targeted drug delivery system, J. Chem. Pharm. Res., 2010, vol. 2, No. 4, pp. 993-998, ISSN 0975-7384.

Sauer, D. et al, Properties of theophylline tablets dry powder coated with Eudragit E PO and Eudragit L 100-55, Pharmaceutical Development and Technology, 2009; 14(6): 632-641.

Ibekwe, V. C. et al., A comparative in vitro assessment of the drug release performance of pH-responsive polymers for ileo-colonic delivery, International Journal of Pharmaceutics, 2006, vol. 308, pp. 52-60, ISSN 0378-5173.

* cited by examiner

FIG. 4 (only relevant part shown)

FIG. 5 (Detailed construction layer C2 only shown partially)

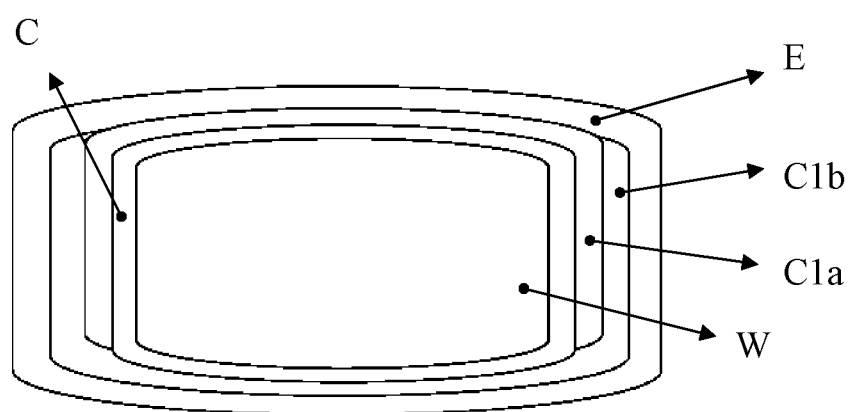
FIG. 6, microtablet (viewed laterally)

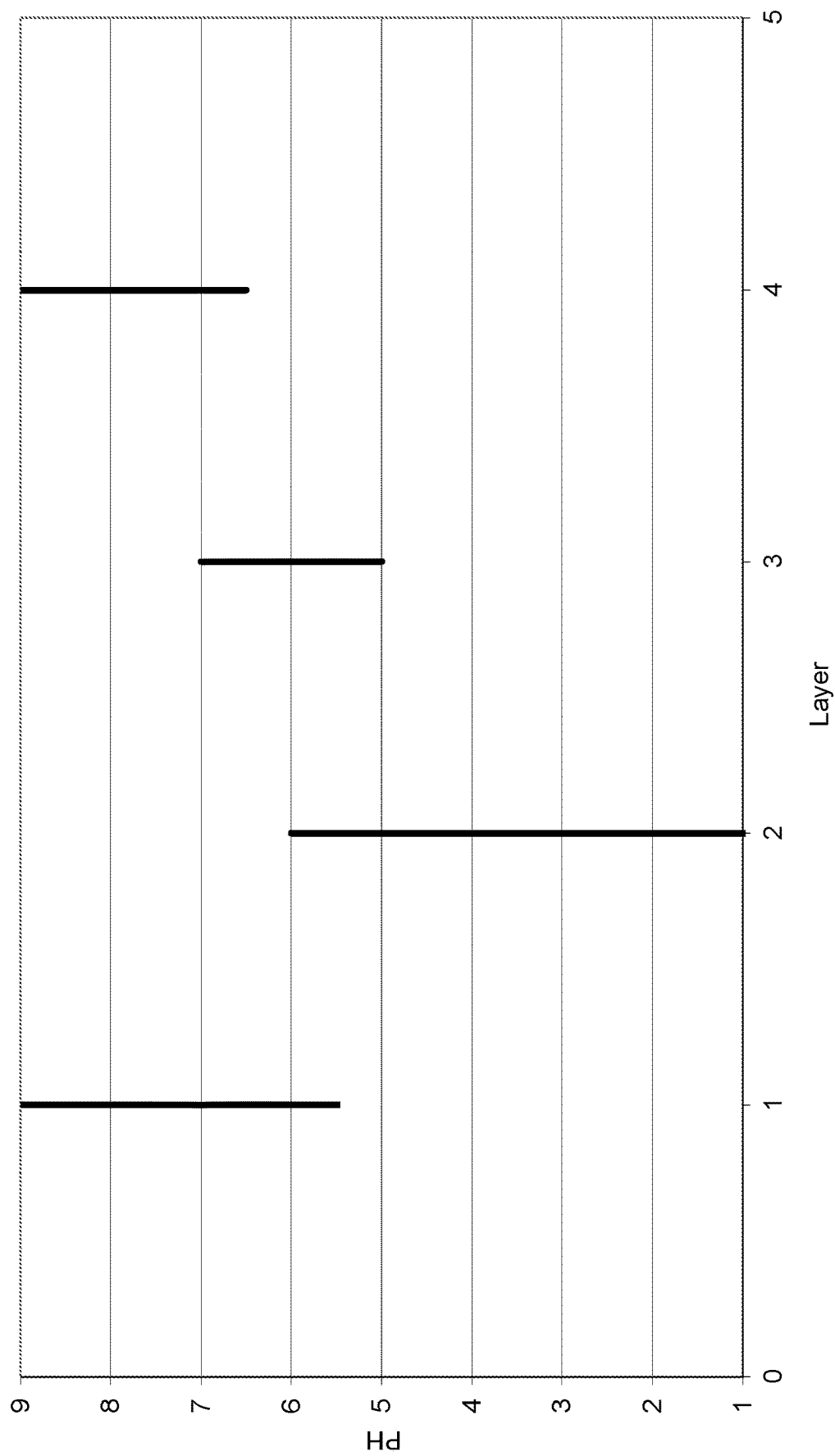
FIG. 7 Ranges of durability of the layers of example 5

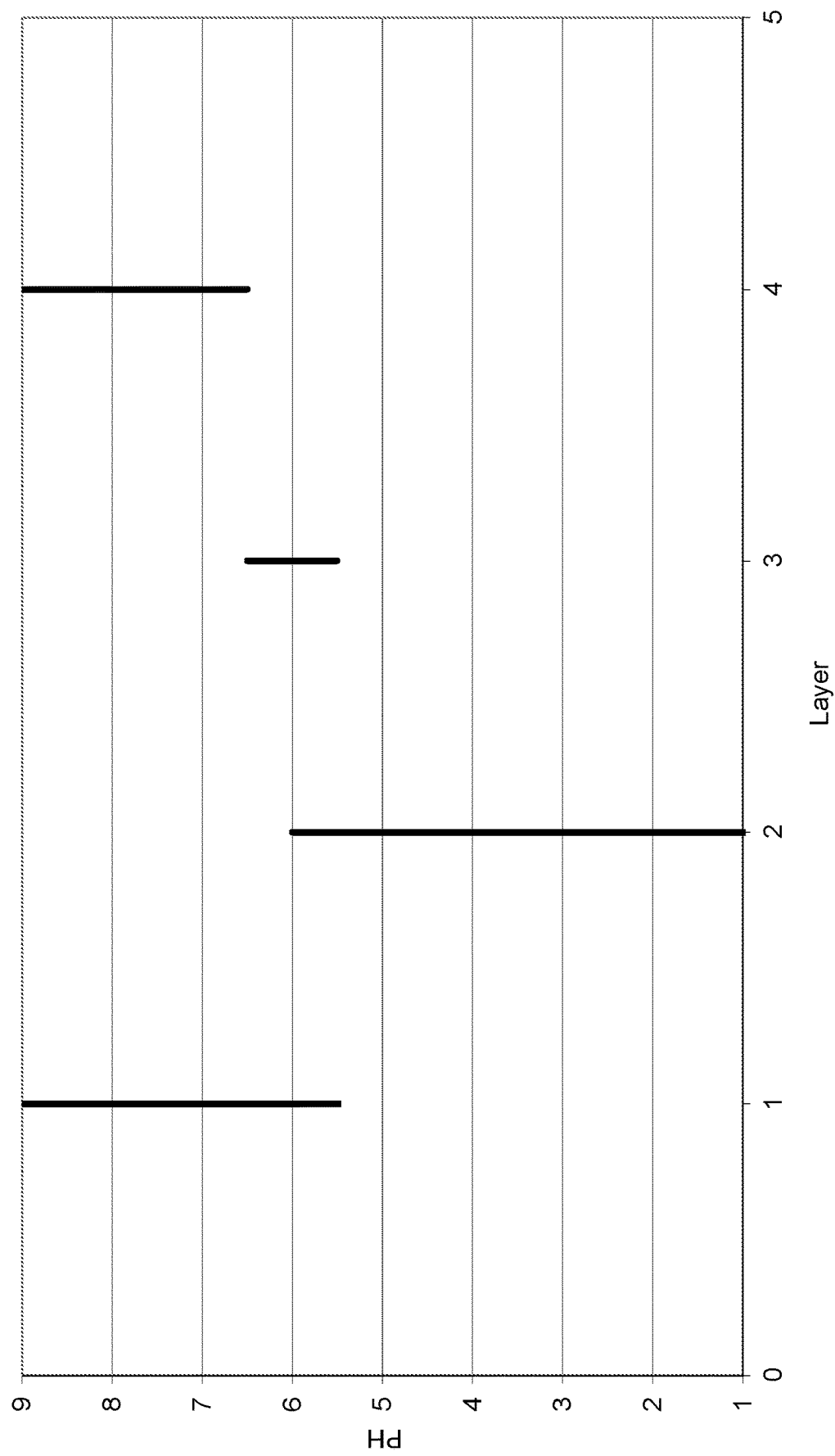
FIG. 8 Ranges of durability of the layers of example 6

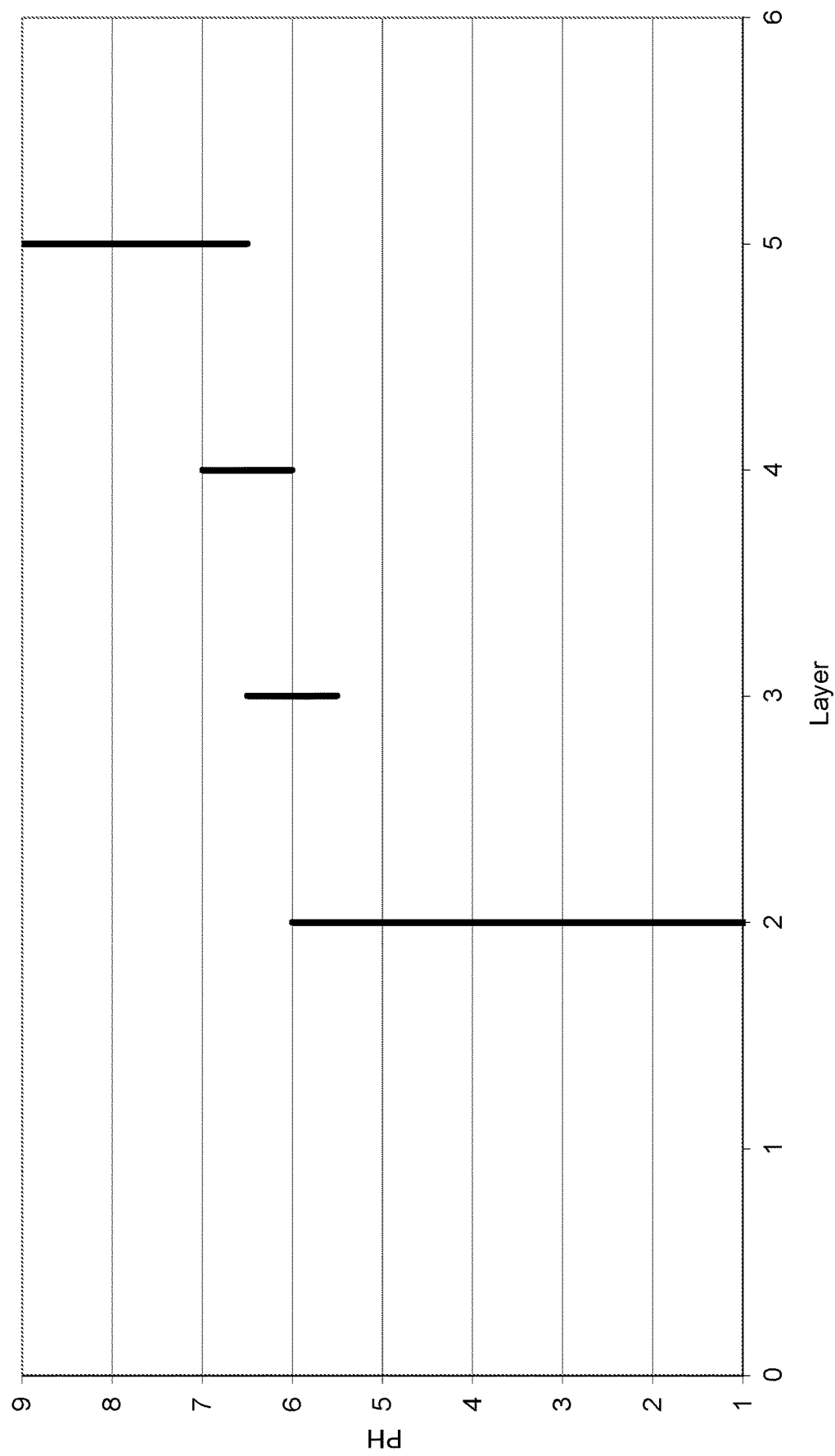
FIG. 9 Ranges of durability of the layers of example 7

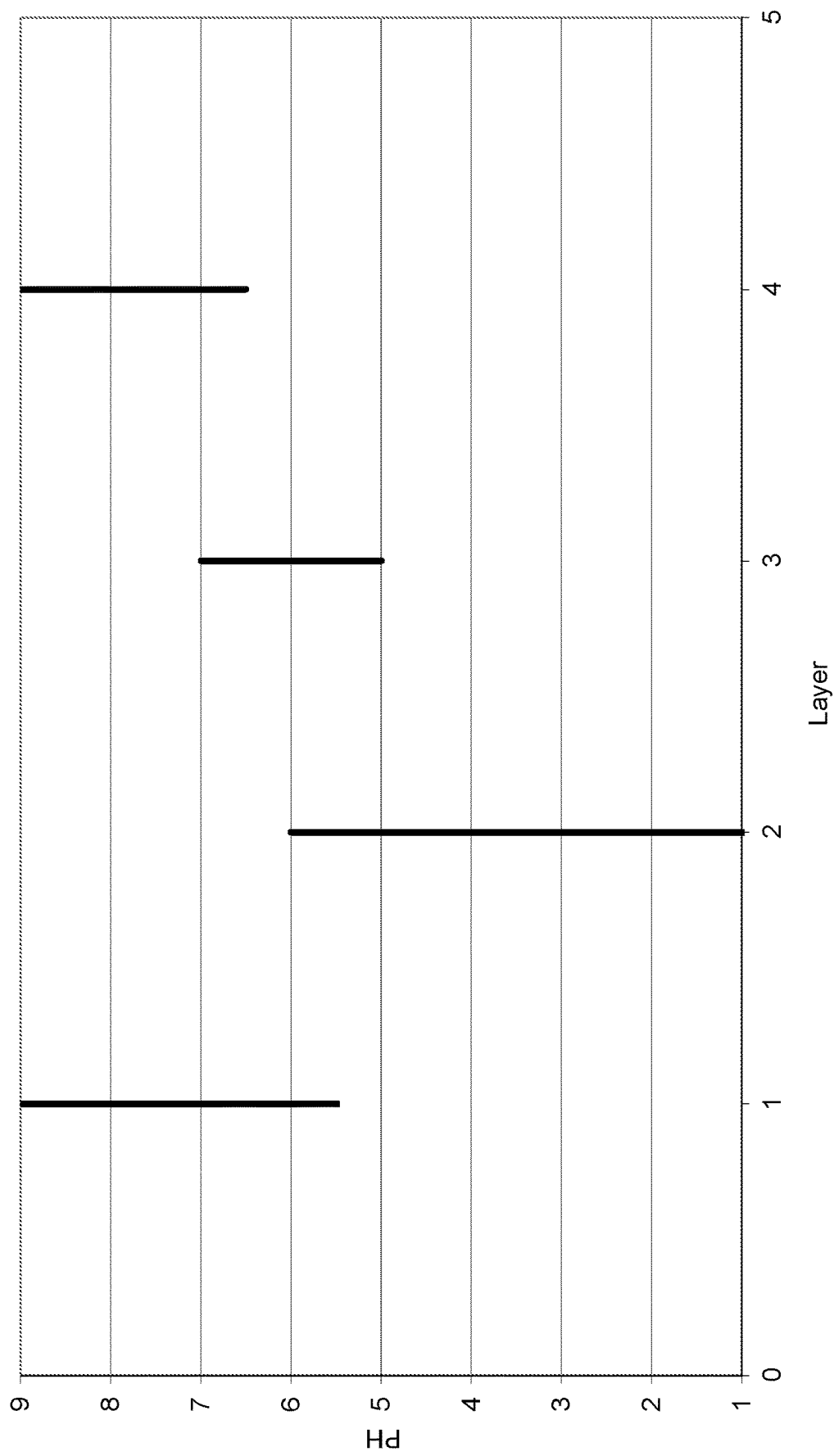
FIG. 10 Ranges of durability of the layers of examples 8a+b

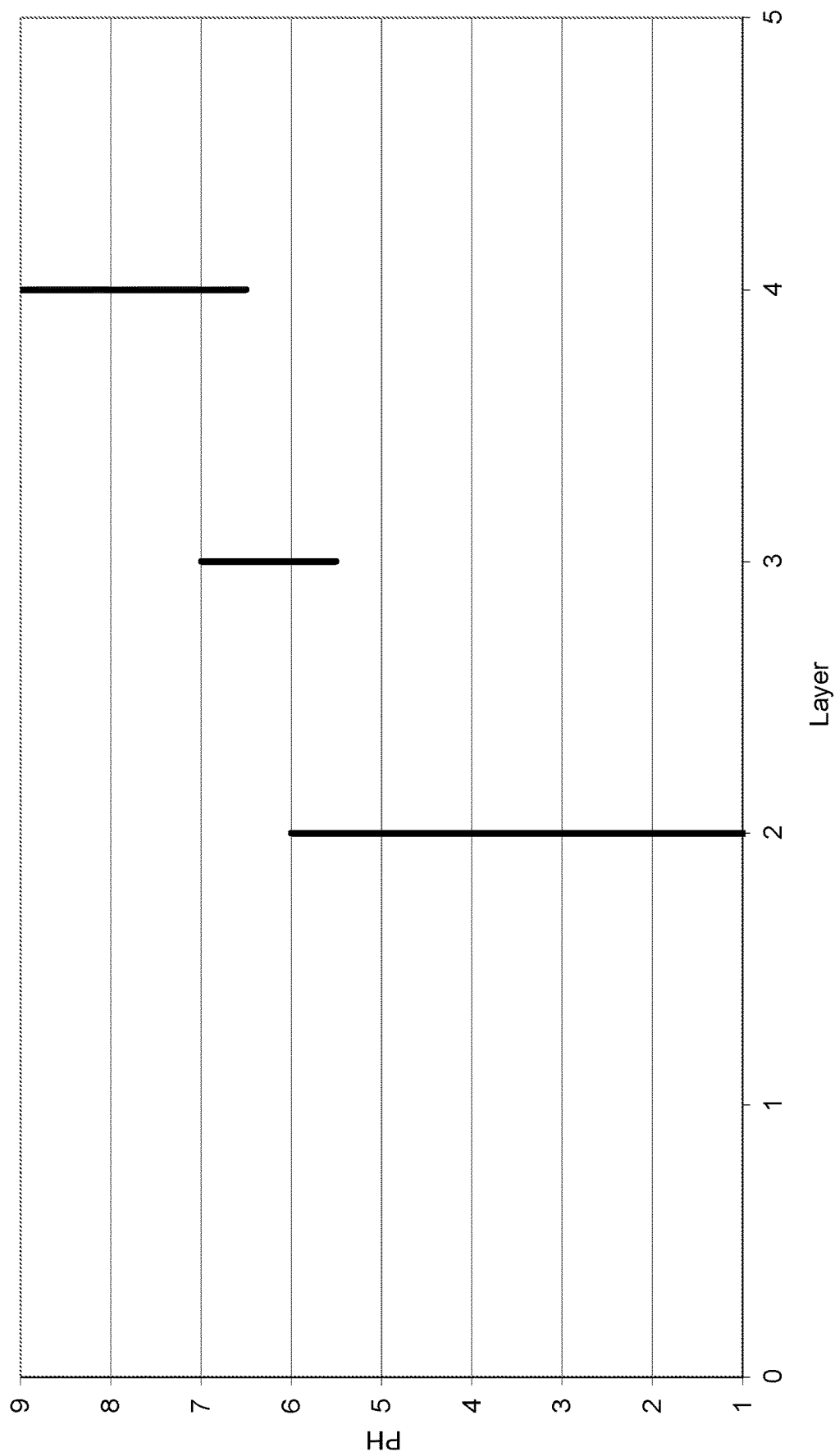

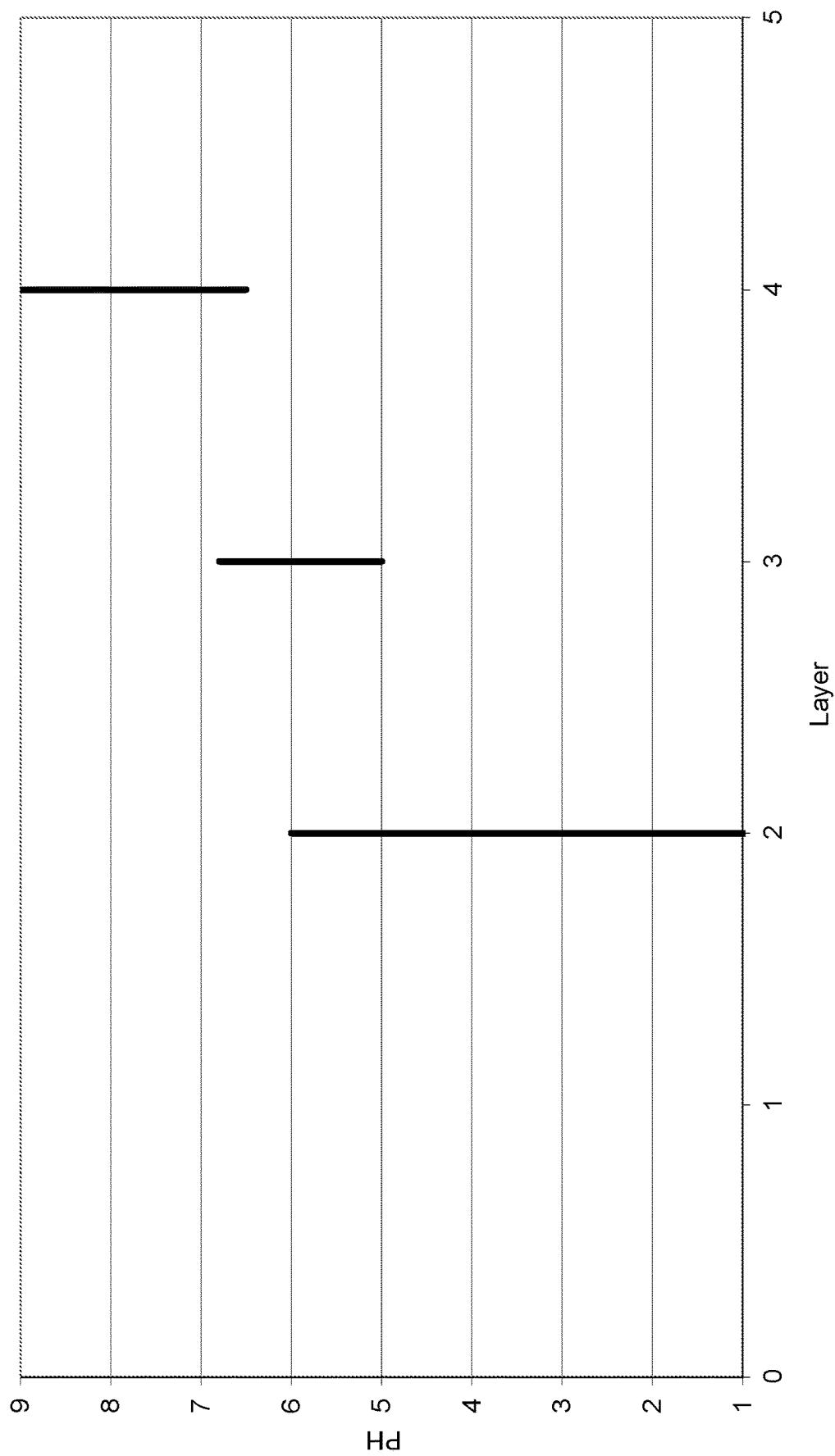
FIG. 12 Ranges of durability of the layers of example 9c

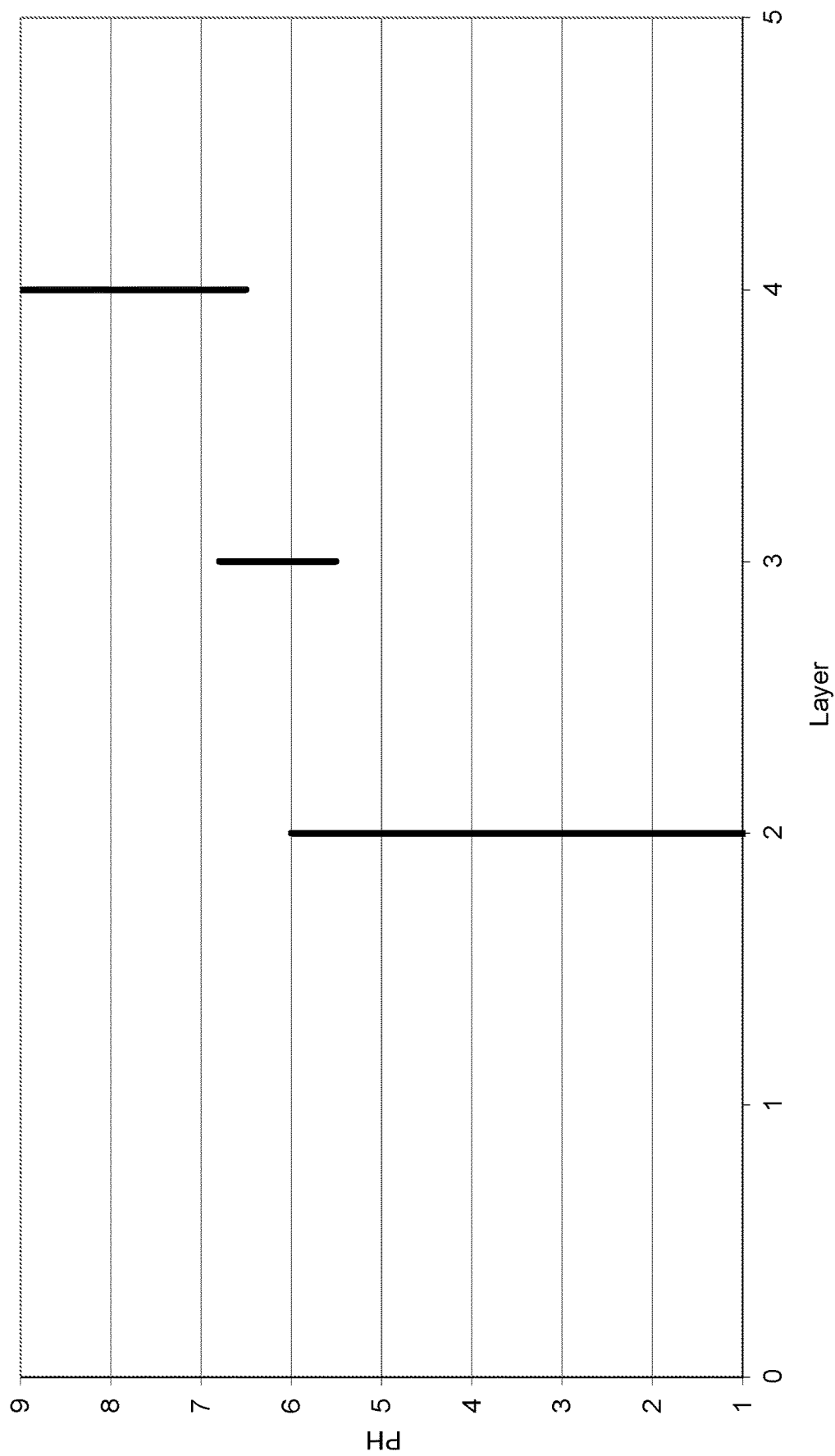
FIG. 13 Ranges of durability of the layers of example 9d

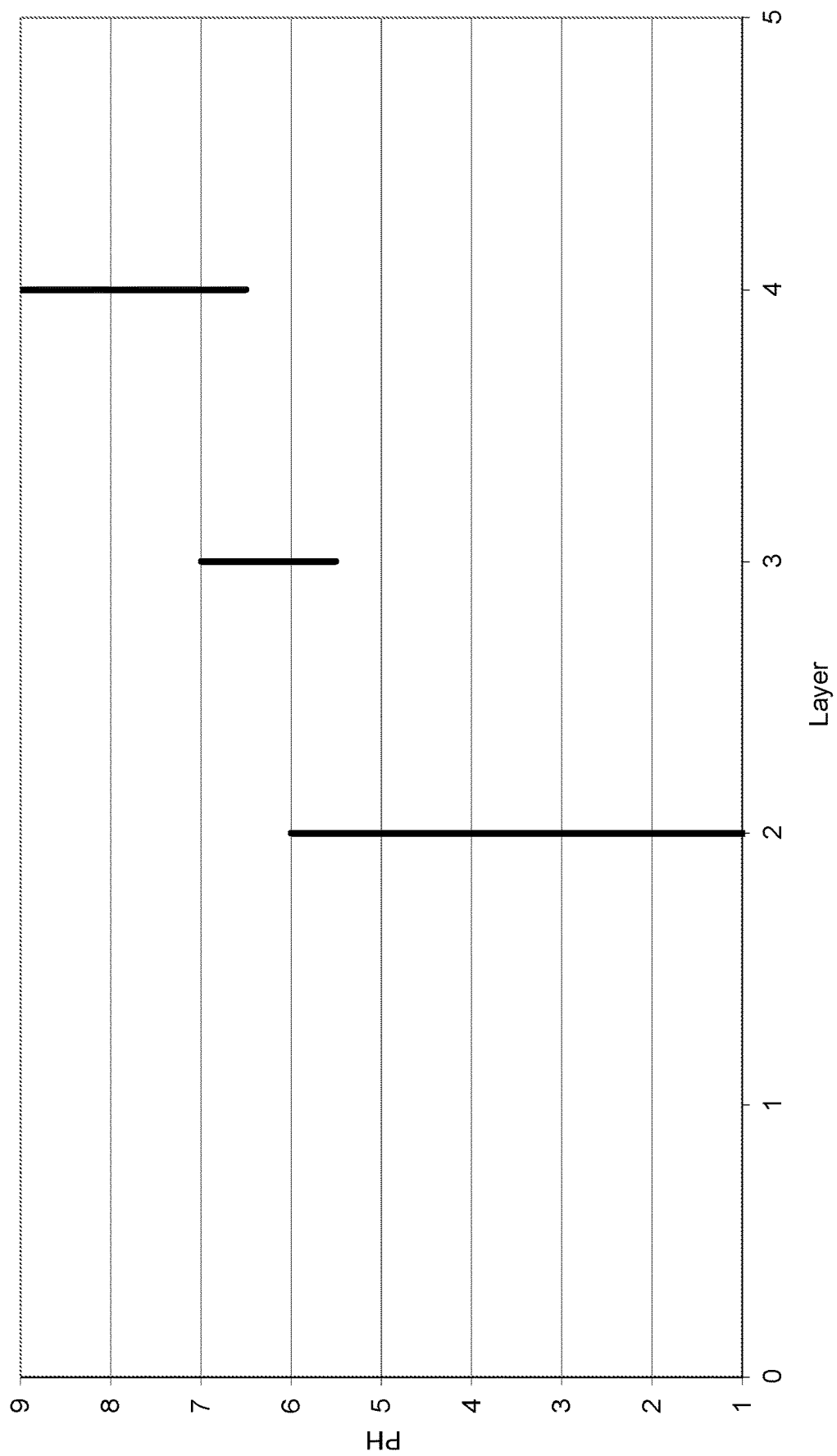
FIG. 14 Ranges of durability of the layers of example 10

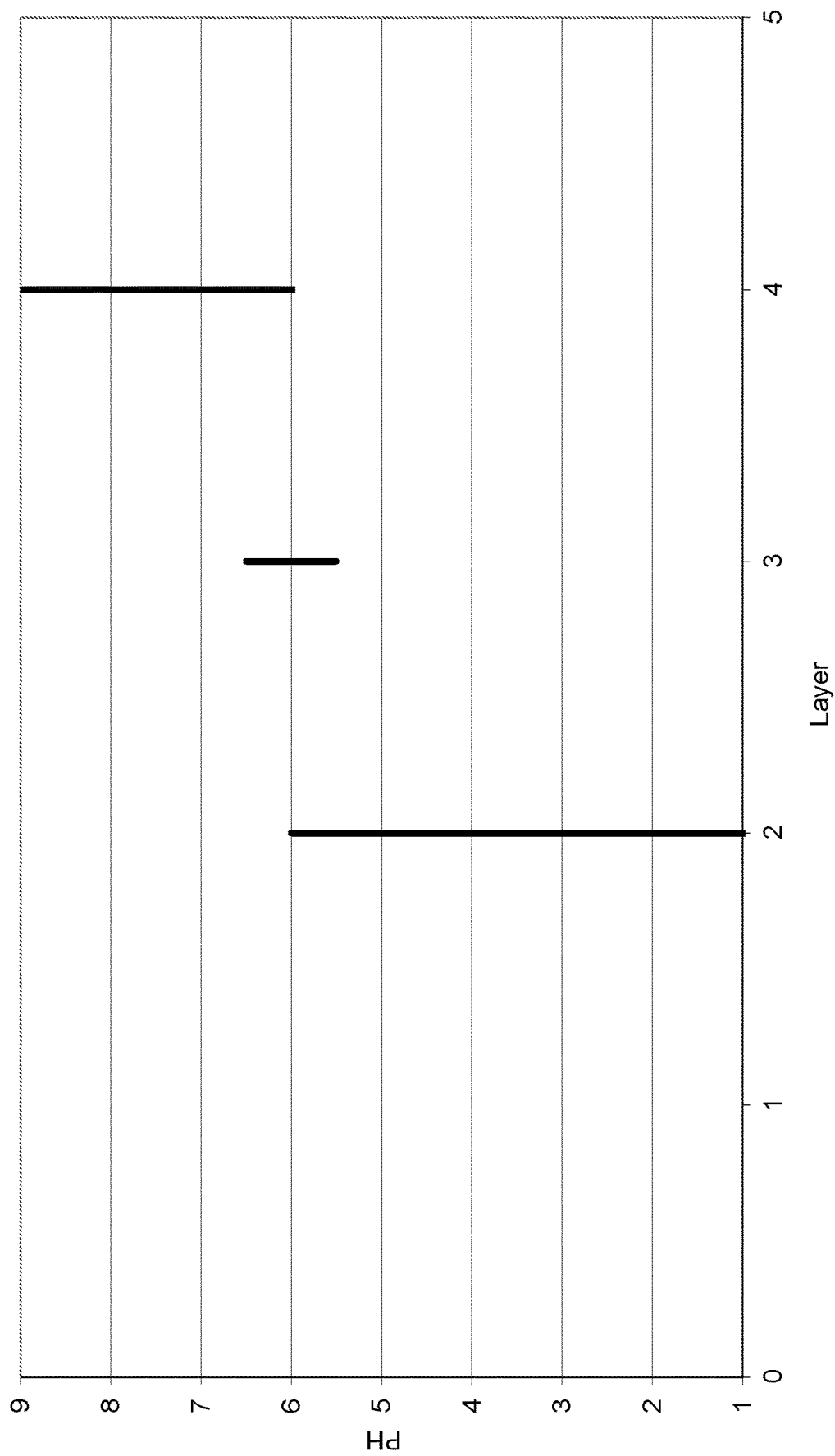
FIG. 15 Ranges of durability of the layers of example 11

FORMULATION FOR THE CONTROLLED RELEASE OF ONE OR SEVERAL SUBSTANCES IN THE DIGESTIVE TRACT OF A MAMMAL

For the achievement of certain desired effects it is advantageous to release one or several substances in the large intestine of a mammal.

The desired effects can be, for example, the specific administration of one or several substances which have a particular therapeutic efficacy if they are released in the large intestine, for example, by the fact that they have an effect there directed on the large intestine mucosa can have an effect on bacteria of the large intestine flora or unfold a better systemic efficacy by special absorption ability of the large intestine mucosa or by avoidance of digestion juices present in the small intestine. Further desired effects of the release of one or several substances in the large intestine of a mammal are known to the person skilled in the art.

One knows that the pH value of the bowel contents, which represent, in principle, a kind of aqueous solution or an aqueous medium, increases after passing the stomach, and that shortly before the reaching of the large intestine reaches a typical value of about 7. It is tried to use this increase to initiate the release of active ingredients. For this purpose active-ingredient containing cores are coated with anionic polymers which are dissolvable in aqueous solutions with a pH value above 7 (FIG. 1 E). If the pH value rises above 7 shortly before the reaching of the large intestine, the coating dissolves and the formulation releases the active ingredients shortly before the entry into the large intestine. In order that the release takes place only in the large intestine, in some cases a slowly dissolving layer is applied underneath the enteric layer which delays the release for a short time, so that the release preferably does not already begin in the small intestine. Because the pH value maximally achieved in the small intestine is subject to an interindividual variability of clearly above one ph unit, a pH value of 7 is not exceeded with all individuals, so that in some cases it does not come to the intended release. If one lowers the threshold of solubility of the anionic polymer, for example, to Ph 6 in order to also achieve a release in these cases, thus with individuals with whom Ph 6 is exceeded shortly before the large intestine, the release takes place as intended, with individuals with whom pH 7 is exceeded shortly before the large intestine, the release, however, possibly takes place too early because with these individuals Ph 6 can already be exceeded in the jejunum. Such formulations which trigger the release depending on the exceedance of a certain pH value are depending on the pH value maximally achieved in the small intestine. They only function reliably, if in the target group of the individuals, with whom a release is intended in the large intestine the maximally achieved pH value, taking into account the interindividual variability, lies within certain margins. The area within these margins is also referred to as operating range in the further course. In order that it does not come to the non-appearance of the release, the threshold value of the anionic polymer must be lower or equal to the lower margin of the desired operating range of the formulation. However, a release can already occur when the pH value exceeds the lower margin of the operating range. Because the slope of the pH value from middle till the end of the small intestine is very low, and the threshold value of the anionic polymer should not already be exceeded in the middle of the small intestine, the operating range of such a technology is very narrow, typically about 0.5 ph units, which is not enough for most applications.

One knows that regardless of the interindividual variability of the intestinal pH value the pH value of the bowel contents falls by typically 1 to 1.5 units on passing the ileocecal valve, and it is tried to use this drop to initiate the release of active ingredients. US20100209520 describes a three-layer system with which two layers control the release. A core free of active ingredient first is coated with an active-ingredient containing layer, there referred to as inner layer. Then the coated core is coated with a layer there referred to as intermediary layer made of a material which becomes dissolvable below a pH value of 6.6. Then a further coating takes place, referred to as outer layer, with a material which becomes dissolvable above a pH value of 7.0. The active ingredient is released if the pH value sinks below 6.6 upon the entry into the cecum, after it had previously risen above 7 after the exit from the stomach.

Because the present invention has similar layers, but calls them differently, in the further course layers like the layer which is referred to as inner layer in US20100209520 are not called inner layers, but are considered as being components of active-ingredient containing cores. Layers similar to the intermediary layer are called most inner layers or "Caecal Coating" (FIG. 2, C), because these do not dissolve before the entry into the cecum. Layers similar to the outer layer of US20100209520 or similar to the layer made of the anionic polymers which are used for triggering of the release after exceedance of a certain pH value are called inner layers or "Enteric Coating" (FIG. 2, E). As outer or most outer layers only such layers are called which lie above an inner layer and preferably offer protection from humidity or neutral to basic saliva, in other words so-called "Protective Coatings" (FIG. 2, P).

The system disclosed in US20100209520 has the disadvantage that the pH value must at least rise above 7, and afterwards must at least drop below 6.6, in order that the release takes place.

Therefore the system is unsuitable if the pH value does not reliably exceed a value of 7 in the small intestine with the target group. With individuals with a lower maximal pH value in the small intestine no release takes place. It is as unsuitable if the pH value does not sink below 6.6 upon the entry into the small intestine. With individuals with a high maximal pH value in the small intestine and/or with individuals with a not very distinctive drop of the pH value upon the entry into the large intestine, also no release takes place. The range of pH values in which such a system can reliably release active ingredients in the large intestine (the operating range) is limited at the lower end by the threshold value of the inner layer, and at the upper end by the threshold value of the most inner layer, increased by the amount by which the pH value drops upon the entry into the large intestine. The reduction of the pH value upon the entry into the large intestine maximally necessary for the release is calculated as follows: Maximal value of the pH value in the small intestine to be expected with the target group less the threshold value below which the most inner layer becomes dissolvable. Because the height of the maximal pH value in the small intestine and the height of the drop of the pH value upon the entry into the large intestine are neither proportional, nor do they otherwise correlate, for a reliable release the reduction of the pH value maximally necessary for the release of a system must be lower, than the slightest drop of the pH value with the achievement of the large intestine occurring in the target group.

If the drop is not reliably higher than 1.4 pH units in the target group, the system disclosed in US20100209520 releases the active ingredient or ingredients reliably in the large intestine only in a range of the pH values maximally occurring in the small intestine from above 7 to below 8. If a maximal pH value in the small intestine of Ph 8.5 is reached with individuals of the target group, a drop of the pH value of over 1.9 pH units upon the achievement(reaching) of the large intestine can be necessary. The threshold value of the most inner layer, below which this becomes dissolvable or permeable (in the further course also called defined first pH value) is in addition not to be increased above the threshold value of the inner layer above which this becomes dissolvable or permeable (in the further course also called defined last pH value), because otherwise with very slow slope of the pH value the most inner coating would become dissolvable immediately after the inner coating without a drop of the pH value being necessary. Even an only slight increase of the threshold value of the most inner layer can lead to unintended release, because the pH value can have slight fluctuations in the course of the small intestine.

Also the threshold value of the inner layer may not be lowered below that of the most inner layer. It is not possible with this system to expand the limited operating range, to reduce the drop of the pH value upon the reaching of the large intestine maximally necessary for the release, or to increase the insensitiveness with respect to fluctuations of the pH value within the small intestine, without making worse at least one of both other parameters in each case. With a target group of individuals with which the slightest occurring drop of the pH value upon the reaching of the large intestine is not greater than the range, within which the individual maximal values of the pH value lie in the small intestine no reliable release in the large intestine can be achieved with this known technique. With this technique it is possible to reliably release active ingredients in the large intestine only if the drop of the pH value after passage of the ileocecal valve is larger than the interindividual variability of the maximal pH value in the small intestine. So the drop of the pH value within the digestive tract maximally necessary for the release is greater than the interindividual variability of the pH value maximally expected within the digestive tract before reaching of the ileocecal valve in the group of individuals, for which the substance or the substances are to be released, therefore greater than the necessary operating range. Operating range (AB), tolerance with respect to fluctuations of the pH value in the small intestine (ST) and necessary drop of the pH value upon the entry into the large intestine (EA) are tied together with systems in the state-of-the-art as follows: EA=AB+ST

PROBLEM TO BE SOLVED

In order to improve the reliability of the release in the large intestine and to reduce the risk for a too early release, as well as for a too late one or a not at all occurring release, need exists for a formulation for the large intestine-specific release of one or several active ingredients or one or several active-ingredient containing cores with which the release is not already then triggered (even not delayed) if the lower margin of the operating range is exceeded and with which the necessary drop of the pH value upon the entry into the large intestine (EA) is smaller than the sum of the width of the operating range and the necessary fluctuation tolerance (AB+ST) and preferably also is smaller than the width of the operating range in itself, if ST is not greater than 20% of the width of the operating range.

DESCRIPTION OF THE INVENTION

A formulation coated in wrong order which was intended for the release by bacterial enzymes of the large intestine flora released the active ingredients unintentional-wise and, hence, unexpectedly also in a simulated cecum medium which, for control purpose, contained no suitable bacterial enzymes.

Investigations showed that an exchange of the order had happened, so that the Kollicoat Smartseal 30D thought as a protective Coating had been applied as the first layer instead of as the last layer, and that such a layer sequence is suitable astonishing-wise for an administration specific to the large intestine.

Originally it had been intended to apply the Kollicoat Smartseal 30D as a most outer layer to cause a protection against neutral to slightly basic saliva, Eudragit L 100 as an underlying layer in order to form a protection against the gastric acid and as the lowest layer a Chitosan grafted with chlorogenic acid to achieve on the one hand a dissolution of the layer by bacterial enzymes of the large intestine-residential bacteria and to allow a release, on the other hand, also if on account of the composition of the large intestine flora none or not enough corresponding saccharolytic enzymes are present, but the pH value in the cecum is higher than usual due to proteolytic bacteria.

Due to the exchange of the order it was found out astonishing-wise that with such a layer order also without the availability of specific bacterial enzymes which can degrade the used polymer a large intestine-specific administration form can be realized.

By further investigations it could be found out astonishing-wise that also without the most inner layer a large intestine-specific administration could be realized with which the operating range is greater, than with use of formulations described in the state-of-the-art.

The invention solves the problem, by providing a formulation which has a coating or other envelopment which is dissolvable or permeable above the defined last pH value.

Under this coating, respectively enveloped by this envelopment, the formulation according to the invention has one or several further coatings underneath each other or further envelopments enveloped by each other which are dissolvable or permeable in each case above an individual defined upper pH value and below an individual defined lower pH value.

Underneath this or these further layer or layers, or enveloped by this or these further envelopments, it has one or several active ingredients or one or several active-ingredient containing cores.

In a preferred embodiment of the invention between the one or more further layers or envelopments and the one or more active ingredients or active-ingredient containing cores an additional, most inner layer or envelopment is arranged which is dissolvable or permeable below a defined first pH value. In a further preferred embodiment this most inner coating or in other way carried out envelopment has a defined second pH value, above which it is dissolvable or permeable as well.

The invention provides, so to speak, a formulation which has a sort of inner layer (layer E, FIGS. 1 to 3), optionally has a sort of most inner layer (layer C in FIG. 2, layer C1 in FIG. 3), and one or more active ingredients or one or more active-ingredient containing cores (W in FIGS. 1-3), and it arranges one or several further layers between the above-mentioned most inner layer and the above-mentioned inner layer or between the one or more active ingredients or the one or more active-ingredient containing cores and the above-mentioned inner layer, where this layer or layer sequence can be realized for example by coating steps, as well as compression steps, emulsification steps or dispersion steps (FIG. 3, layers C2 to Cn). Those layers lying between the inner layer and the most inner one or between the inner layer and the one or more active ingredients or the one or more active-ingredient containing cores are hereinafter also referred to as further layers.

These one or several further layers also have, similar to the above-mentioned inner or most inner layer, solubility or permeability characteristics dependent on pH nevertheless in such a way that they are or become dissolvable or permeable in each case below a defined lower pH value, and in addition, are or become dissolvable or permeable above a defined upper pH value. In the range between their individual defined lower and defined upper pH value this layer is, or these layers are not dissolvable or permeable in each case, at least not within a timeframe in which they are, in the gastrointestinal tract before the ileocecal valve, exposed to the contents of the same.

In order that the individual further layers become dissolvable or permeable only successively with monotonously increasing pH values, and this also only with further increasing pH values, the defined upper pH value of each further layer previously applied, or subsequently exposed to the bowel contents, is higher, not by necessity always by the same, but always by a positive value, than the defined upper pH value of the layer subsequently applied, or previously exposed to the bowel contents.

In order that with falling pH value (excluded upon the reaching of the stomach) with a drop of the at least the desired height, or anyway with a drop at least by height of the difference between the defined upper pH value and the defined lower pH value of the layer currently exposed to the aqueous solution, all other layers still being present become dissolvable or permeable, and thus the one or more active ingredients or one or more active ingredient cores are released, the defined lower pH value of each layer previously applied, or subsequently exposed to the bowel contents is preferably higher than or as high as the defined lower pH value of the layer subsequently applied, or previously exposed to the bowel contents.

The defined upper pH value of every further layer is higher by a defined amount "delta 1" than the defined upper pH value of the overlying layer. The defined lower pH value of every further layer is lower by a defined amount "delta 2" than the defined upper pH value of the overlying layer, but preferably is not lower than the defined lower pH value of that.

The following is thereby ensured: With monotonous increase of the pH value in each case only one layer dissolves or becomes permeable in order to expose the next layer.

With embodiments with no most inner layer the one or more active ingredients are only released after the dissolving of the farthest inside lying further layer or it becoming permeable.

With embodiments with most inner layer no release is triggered by monotonous increase of the pH value, unless, the defined second pH value of the most inner layer is exceeded.

However, with a renewed decrease of the pH value after the occurred stomach passage by at least the defined amount "delta 2" and at most by the sum of the defined amounts "delta 1" and "delta 2" all coatings are dissolved or become permeable, so that the one or more active ingredients are released.

The inner layer has a defined upper pH value "last pH value" which usually lies above the pH value to be expected in the stomach, and above which this layer is dissolvable or permeable. If the underlying layers are durable long enough in the Ph range in which they should not become dissolvable or permeable, the defined upper pH value of the inner layer can also lie below the pH value maximally to be expected in the stomach. This is especially advantageous with administration to individuals who have, on the basis of inner or external circumstances, as for example diseases or drugs, relatively high Ph values in the stomach, as well as also for individuals who have, on the basis of inner or external circumstances, as for example diseases or drugs, relatively low small pH values in the bowel, as well as for individuals which belong to both groups, which is why a further preferred embodiment of the invention provides this.

To make sure that the inner layer becomes dissolvable or permeable before the reaching of the ileocecal valve, the invention provides in a further preferred embodiment that the pH value, above which the inner layer becomes dissolvable preferably is not higher than the lowest maximal value of the pH value to be expected being present with the target group (humans or animals to which the one or more active ingredients are to be administered) in the small intestine. This value is, for example, with humans typically 6.5, however, can be also higher with certain groups of persons, for example, with gastrointestinal diseases, but particularly also be lower, for example, 6 or partially also thereunder (minimum values of 5.5 or 5 occur in some cases). Interindividual variability can cause that in the small intestine a pH value of 7 is not exceeded reliably, even with otherwise bowel-healthy individuals. With some diseases, as for example Crohn's disease or with individuals whose small intestine was removed partly, the pH values maximally reached in the small intestine can lie, for example, below Ph 6, according to the severity of the disease also under 5, e.g., if both diseases are present, or with combinations of further causes for low pH values even maximal pH values of less than 4.5. Therefore, the invention provides in a further preferred embodiment that the defined upper pH value of the inner layer is lower than Ph 7, preferred lower than Ph 6, more preferred lower than Ph 5 and particularly preferred lower than Ph 4.5.

The inner layer can be also dissolvable or permeable below certain pH values, nevertheless only below a pH value which lies below the value which minimally is to be expected with the target group within the gastrointestinal tract. Also the most inner layer may be dissolvable or permeable above a certain pH value (the defined second pH value). This range above the defined second pH value can extend over the whole range above the maximal value which is maximally to be expected with the target group, without the release behavior being significantly changed thereby, which is why this is provided in a further preferred embodiment of the invention. For particular applications it can be advantageous that the defined second pH value lies below the pH value maximally to be expected with the target group in the course of the small intestine. This can be used, for example, to initiate a release if in a part of the target group a certain pH value is exceeded shortly before reaching of the large intestine. A further preferred embodiment of the invention provides that the defined second pH value lies below the pH value maximally to be expected with the target group in the course of the small intestine, namely preferably by 0.2 to 1.2 pH units, more preferably by 0.4 to 0.8 pH units, particularly ably by 0.5 to 0.65 pH units, for example, by 0.55 pH units.

Due to the possibility to be able to keep the defined upper pH value low, because a release takes place only after a likewise occurred dissolution or permeabilization of the next inner layer, the defined lower pH value of the next inner layer can also be kept low, what is of benefit just particularly for the feasibility of accordingly release-controlled administration forms for individuals who have, on the basis of inner or external circumstances, relatively low small intestine pH values.

The defined lower pH value of the most outer further layer can be held low, for example in order to take account for the above-mentioned diseases like Crohn's disease, short bowel syndrome or the like, which is why the invention provides in a further preferred embodiment that the defined lower pH value of the most outer further layer is lower than pH 7, preferably lower than pH 6, more preferably lower than pH 5 and particularly preferably lower than pH 4.

The inner layer is durable either in the whole pH range below its defined upper pH value or at least till below the pH value minimally to be expected in the stomach.

With the definition of the parameters "Delta 1" and "Delta 2" of the individual layers these parameters can be identical with all further layers, but also different values can be taken to achieve desired release characteristics.

The value "last pH value" preferentially has a value of 2 to 9, more preferred a value of 4 to 8 and particularly preferred a value of 4.5 to 7.5, because maximal stomach pH values almost never reach Ph 7.5, and the pH value maximally to be expected in the small intestine most often does not lie below 4.5.

The value "first pH value" preferentially has a value of 2 to 9, more preferred a value of 3.5 to 8 and particularly preferred a value of 4.5 to 7.5, because maximal cecum pH values less often reach pH 8, and the pH value maximally to be expected in the small intestine most often does not lie below 4.5.

The parameters "Delta 1" and "Delta 2" of the individual layers preferably have values of 0.1 to 2, more preferred values of 0.25 to 1, and particularly preferred values of 0.4 to 0.7. Thereby a controlled release can be also achieved if the interindividual variability of the small intestine pH value maximally to be expected is smaller than 2 ph units, like with very heterogeneously composed target groups, if the variability is smaller than 1, like with normally composed target groups, and it can also be taken benefit of relatively small Ph decreases upon the passage of the ileocecal valve or with accordingly homogeneously composed target groups or with the use of several further layers by choosing small "Delta 1" and "Delta 2" values. In particular with the use of several further layers a controlled release can be also achieved if the interindividual variability of the pH value maximally to be expected in the small intestine is higher than 1 pH unit, preferably higher than 2 pH units, more preferred higher than 3 pH units, and particularly preferred higher than 4 pH units.

The pH value below which the most inner layer or a further layer dissolves, preferably does not lie above the defined pH value, above which the overlying layer dissolves, because otherwise with a too slow increase of the pH value the most inner or further layer would become dissolvable or permeable immediately after the overlying layer, without a drop of the pH factor being necessary, which is why a further preferred embodiment of the invention provides such a preferred implementation.

However, Delta 2 can also be 0. With relatively low dissolution speed of the layers and relatively quickly increasing pH values in the small intestine, Delta 2 can be also negative, without thereby a too early release taking place. The operating range can thereby be further increased, or the necessary drop of the pH value upon the entry into the large intestine be further decreased. Therefore, in a further preferred embodiment of the invention it is provided that Delta 2 does not have to be positive, however, preferably is not more negative than −0.5, particularly preferred not more negative than −0.25.

In order that the next inner layer does not dissolve or becomes permeable already when the increase of the pH value takes place very slowly, and fluctuations of the pH value occur, for example, by non-uniform mixing of the bowel contents with digestion juices, a further embodiment of the invention provides, that the pH threshold value below which the next inner layer becomes dissolvable or permeable (the defined first pH value of the most inner layer or the defined lower pH value of a further layer), is lower by a certain amount than the pH threshold value, above which the layer lying above it becomes dissolvable or permeable (the defined last pH value of the inner layer or the defined upper pH value of a further layer).

This amount should be at least 0.1 ph units, because fluctuations below this value occur very often, preferred 0.2 pH units, because fluctuations around this value occur on occasion, and particularly preferred at least 0.4 units, because fluctuations by 0.2 to 0.4 units are not impossible. However, the amount should not be higher than 2.5 pH units, because the drop of the pH value after passage of the ileocecal valve usually does not amount to more than 2.5 pH units, preferably not higher than 1.5 units, because it often does not fall more than 1.5 units, and particularly preferred by no more than 1 pH units, because the drop does not amount to more than 1 pH units with all mammals.

It was also found out unexpectedly that it was possible with the analyzed layer sequence to tolerate even greater fluctuations of the pH value within the small intestine without impairing the targeted release in the large intestine, and that such a layer sequence was advantageous.

Because of that, a further preferred embodiment of the invention provides that the formulation is also suitable for individuals with whom the fluctuations of the pH value after exit from the stomach and before reaching of the ileocecal valve, or the deviations from the monotonicity of the course of the pH in this area are greater than 0.1 pH units, preferred greater than 0.3 pH units, particularly preferred greater than 0.6 pH units.

In particular with ruminating mammals higher and under circumstances repeated fluctuations of the pH value are possible, which is why the invention provides in a further preferred embodiment that the described formulation is not determined for the use with ruminating mammals, preferably not for the use with ruminant mammals with whom the fluctuations of the pH value after the exit from the stomach are greater than 1.0 pH units, particularly preferred not for the use with ruminant mammals with whom these fluctuations are greater than 2.0 pH units.

The use of the described formulation is especially advantageous with mono-gastric mammals, which is why the invention provides this in a further preferred embodiment.

A further preferred embodiment of the invention provides that the mammal for whom the formulation is determined is a human.

A further preferred embodiment provides that the coating or envelopment of the one ore more active ingredients or the one or more active-ingredient containing cores only dissolves completely or becomes permeable when the pH value of the food pulp surrounding the coating decreases by an amount of 0.2 to 4, more preferred by an amount of 0.4 to 1.5, particularly preferred by an amount of 0.5 to 0.8, after it had increased before above a certain value. By the requirement that a certain minimal amount of pH-decrease is necessary for the dissolution it is achieved that the one or more active ingredients are not already released with smaller fluctuations of the pH value within the small intestine.

Due to the one or several further layers it is possible to choose the defined upper pH value of the inner layer lower, than the defined lower pH value of the most inner layer or the farthest inside lying further layer, without an unintentional release taking place, even if the pH value only increases slowly or not at all for longer time in the course of the small intestine. Therefore, a further preferred embodiment of the invention provides that the defined upper pH value of the inner layer is lower, than the defined lower pH value of the most inner layer. A further preferred embodiment of the invention provides that the defined upper pH value of the inner layer is lower, than the defined lower pH value of the farthest inside lying further layer, provided that between these both layers at least one additional further layer is arranged. The amount by which the defined upper pH value of the inner layer is lower in each case is preferably from 0.2 to 1.2 pH units, more preferred 0.4 to 0.8 pH units, particularly preferred 0.5 to 0.65 pH units, for example, 0.55 pH units.

In order that the inner layer is not already dissolved in the oral cavity, several possibilities are known to the person skilled in the art. Among others, the administration of the active ingredients coated as described inside a capsule made of hard gelatin or hydroxypropylmethylcellulose or also the application of an additional, outer coating which dissolves not until in the stomach.

The different embodiments of the invention allow that the reduction of the pH factor within the digestive tract maximally necessary for the release is smaller, than the interindividual variability of the pH value maximally to be expected within the digestive tract before reaching of the ileocecal valve in the group of individuals for whom the substance to be released, or the substances to be released are determined.

The reduction of the pH value within the digestive tract maximally necessary for the release is calculated by the following equations:

Value A: Maximal value of the pH value in the small intestine to be expected with the target group less the certain pH value under which the most inner coating dissolves or becomes permeable.

Value B: Distance between defined upper and defined lower pH value above which, or below which that further layer becomes dissolvable or permeable with which this distance is the greatest.

The greatest one of the two values A to B represents the reduction of the pH factor within the digestive tract maximally necessary for the release.

With embodiments of the invention without most inner layer only value B applies. With embodiments with which the defined second pH value of the most inner layer is lower than the pH value in the small intestine maximally to be expected with the target group, value A is calculated from the difference between the defined second pH value and the defined first pH value of the most inner layer. The ratio of necessary decrease of the pH value to the operating range is improved by the difference between the pH value in the small intestine maximally to be expected with the target group and the defined second pH value of the most inner layer or the defined upper pH value of the farthest inside lying further layer. With such embodiments this difference also determines the amount by which the operating range can be extended upwards with the necessary drop of the pH value being unchanged.

This difference should not be chosen too high, because otherwise with individuals whose pH value maximally achieved in the small intestine lies at the upper edge of the operating range the defined upper pH value of the farthest inside lying further layer, or the defined second pH value of the most inner layer, is, perhaps, exceeded too long before the reaching of the large intestine, and the risk of a release already before the reaching of the large intestine rises. Therefore, the difference preferably amounts to between 0.1 and 1.2 pH units, more preferred between 0.4 and 0.8 pH units, particularly preferred between 0.5 and 0.65 pH units, for example, about 0.55 pH units.

The utilization of the change of the pH value for the release of the one or more active ingredients is realized by coating, mixture, dispersion, emulsion, compression, granulation or otherwise performed envelopment of the one or more active ingredients which if necessary, are mixed, compressed or otherwise processed with or without further additives, with materials or material mixtures which have defined durabilities against aqueous solutions with certain pH values, preferably taking place successively several times. The materials or material mixtures are dissolvable or permeable in watery solutions of certain ranges of the pH value, and indissoluble or not permeable in aqueous solutions of other ranges of the pH value.

The materials are selected, for example, from the group of polymers, copolymers, monomers, gels, polysaccharides, if necessary mixed or otherwise processed with pharmaceutical excipients.

Due to the sequence of different coatings it is achieved that only then all layers are removed, dissolved or have become permeable if after an increase of the pH value above a certain value a drop of the pH factor has taken place by another certain amount, or under a certain value, or with particular embodiments if the increase has taken place above a certain higher value.

This is achieved by the fact that every layer only then dissolves or becomes permeable if a defined upper pH factor is exceeded, or another defined lower pH factor is undershot.

For the construction of the further layers, for example, materials are used which are durable only in certain ranges of the pH value against aqueous solutions, or mixtures of different materials of which at least one is dissolvable or at least permeable above certain pH values in aqueous solutions and at least one other is dissolvable or permeable below certain pH values in aqueous media to obtain a layer which is durable against aqueous solutions only in the range in which at least these both used materials are durable.

For example, but not limiting the invention to these, the following materials which can serve preferably as components of such mixtures are mentioned here: Eudragit L 100, Eudragit FS 30D, Eudragit E 100, Kollicoat Smartseal 30D, polyvinylacetal-diethylaminoacetate, polyvinylacetal-dimethylaminoacetate, poly(N-acryloyl-N-'-ethyl piperazine-co-methyl-methcrylate), poly(diethylaminoethylmethacrylate-HCl)("Potentiometric Titrations of Polyelectrolytes with Separation of Phases", Shatkay et al.).

The construction, or the production of such layers is based, for example, however not limiting the invention, on the same or similar steps and materials like with the already mentioned layers which are dissolvable or permeable only below or only above a certain pH value where the components which are primarily responsible for the pH-dependent properties, as for example the cationic or anionic polymers or copolymers, are exchanged for polymers or copolymers or other film-forming pH-dependent dissolvable or permeable materials which have preferably cationic as well as anionic properties. This can be, for example, cationic polymers whose molecule structure is grafted with anionic subunits, or anionic polymers with cationic subunits. Also polymers can be used, with which single, or certain portions of Ionic molecule constituents, also called as functional groups, are exchanged for other Ionic molecule constituents which have contradicting Ionic properties, for example, carboxyl groups against amino groups. Also other materials which are dissolvable or permeable below and above a certain range of the surrounding pH value and are durable within the certain range can be used.

An example not limiting the invention is a Chitosan polymer which has cationic properties, and therefore is dissolvable at acidic pH values, but undissolvable at neutral and basic pH values of the surrounding solution. Subunits with anionic properties are inserted by enzymatic grafting with chlorogenic acid whereby the polymer also becomes dissolvable in basic solutions, and therefore is undissolvable only in a limited range around the neutral pH value.

The solubility of the polymer in the basic and acidic range can be adjusted by the percental portion of the grafting with which primarily the upper, but also the lower pH value, above or below which a layer made with this polymer is dissolvable, can be determined. See "Enzymatic Grafting of a Natural Product onto Chitosan to Confer Water Solubility Under Basic Conditions" (Guneet Kumar et al, BIOTECHNOLOGY AND BIOENGINEERING, VOL. 63, NO. 2, Apr. 20, 1999).

EP0466566B1 also describes that the pH value, below which Chitosan is dissolvable, is dependent on the degree of the deacetylation and the degree of the polymerization, so that appropriate options for the adjustment of the desired parameters are known to the person skilled in the art.

Among other reasons, because Chitosan is a modified natural product, the solubility parameters also depend on the used production process, so that according to manufacturer, degree of polymerization and deacetylation different degrees of grafting can be necessary, as well as the coating thicknesses have to be adapted under circumstances.

Other polymers, as for example amylose, can be modified in similar manner to achieve suitable solubility profiles, as for example the publications mentioned in the above-mentioned publication show. For this purpose it is not mandatory that enzymatic processes are used.

Another example of a polymer which can be used for the production of one or several further layers is a Chitosan polymer which is modified with succinic anhydride, as for example described in "Zwitterionic chitosan derivatives for pH-sensitive stealth coating", Peisheng Xu et al., Biomacromolecules, 2010 Sep. 13; 11(9): 2352-2358. Further descriptions, how functional molecule groups can be modified, are described in the chemical technical literature, for example, the modification of amino groups in "Modification of Amino Groups" in "Current Protocols in Protein Science", Supplement 4, 1996, Wiley, here in particular the succilylation, amidation and methylization, as well as assistances with possibly occurring problems, as well as also in Klotz, I. M. 1967. "Succinylation". Methods Enzymol. 11:576-580. Polyaspartamide polymers, according copolymers and/or grafted variations as for example PHEA-g-$C_{18}$10-IM50, PHEA-g-$C_{18}$10-IM90, PHEA-g-$C_{18}$10-PY45, PHEA-g-$C_{18}$10-PY70 described in "Tunable phase transition behaviors of pH-sensitive polyaspartamides having various cationic pendant groups", Han Woong Park, Colloid Polym Sci (2009) 287:919-926, are as usable. The weight proportions of the individual functional groups can be varied as described, also in ratios which are not stated explicitly there.

To the person skilled in the art some ways of realization of formulations are known which he can apply to prevent the release of active ingredients or of active-ingredient containing cores so long, until a certain pH value has been exceeded.

For this purpose means are available to him, for example, provided by the industries which are usually called "Enteric Coating". Inter alia, also in the present invention such coatings and if applicable the materials intended for them are called "Enteric Coating" (E). The inner layer of the present invention is usually produced with the use of such or similar materials. Inter alia, examples of products usable for this are, but not limiting the invention, Eudragit FS 30D, Eudragit S 100, Eudragit L 100, Eudragit L 100-55, Eudragit L 30 D-55. In several brochures of the company Evonik, Darmstadt, the realization of suitable coatings is described. Further examples are hydroxypropyl-methylcellulose-acetate-succinate (HPMCAS; Shin-Etsu AQOAT®, types AS-LF, AS-MF, AS-HF; Shin-Etsu Chemical Co., Ltd. Niigata, Japan), cellulose acetate phthalate (CAP), hydroxypropyl methylcellulose phthalate (HPMCP), polyvinyl acetate phthalate (PVAP), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L 30 D-55), Kollicoat EMM30D, Estacryl 30D, Coateric, and Aquateric).

Also some ways of the realization of formulations are known to the person skilled in the art that he can apply to prevent the release of active ingredients or of active-ingredient containing cores, so long until a certain pH value has been undershot. For this purpose means are available to him, for example, provided by the industries which are usually called "Gastric Coating" or "Protective Coating". Inter alia, also in the present invention such coatings and the materials intended for it are called "Protective Coating" (P), however, can serve also as a "Cecal Coating" (C). The most inner layer of certain embodiments of the present invention is usually produced with the use of such or similar materials. Among others, examples of products usable for this are, but not limiting the invention, Eudragit E P O, Eudragit E 100, Kollicoat Smartseal 30D, poly(methylmethacrylate-diethylaminoethylmethacrylate)-copolymers (poly (MMA-DEAEMA)), poly(N-acryloyl-N'-ethyl piperazine-co-methyl methacrylate)-copolymers, poly(methylmethacrylate-dimethylaminoethylmethacrylate)-copolymers (Poly(MMA-DEAMMA)). In several brochures of the company Evonik, Darmstadt, or the company BASF, the realization of suitable coatings is described.

An adjustment of the pH value, above or below which a layer becomes dissolvable or permeable, can also be made by copolymerization of different monomers which have different hydrophobic, hydrophilic or Ionic properties.

Exemplarily would be referred here to "Tunable phase transition behaviors of pH-sensitive polyaspartamides having various cationic pendant groups", Han Woong Park, Colloid Polym Sci (2009)287:919-926. There various polymers are synthesized which are indissoluble within limited Ph ranges but dissolvable above and below. The adjustment of the pH values, above or below which a layer becomes dissolvable or permeable, can be made on the one hand by the type of monomers used, in particular by use of monomers with different pKs values, or by their percentages in the copolymer, for example, via variable quantitative proportions, see "Enteric microparticles coated with smart polymers for controlled drug delivery applications" (Annalisa Dalormo), in particular chapter 3, as well as especially FIG. 29. For example, the threshold values of Poly(MMA-AA)-copolymers can be adjusted between pH 2.7 and pH 8.3 whereby they preferably can be used between pH 2 and pH 9.

Analogous to the adjustment of the pH value above which, e.g., a Poly(MMA-AA) copolymer becomes dissolvable by alteration of the proportional content in acrylic acid, for example, also the pH value below which, e.g. a poly (MMA-DEAEMA) copolymer, as it is used in Kollicoat Smartseal 30D, becomes dissolvable, can be adjusted by alteration of the proportional content in diethylaminoethylmethacrylate. Various options are known to the person skilled in the art for this purpose. Also polyvinylacetal-diethylaminoacetate can be adjusted by the ratio of the monomers accordingly. The pH value below which a poly (N-acryloyl-N'-ethyl piperazine-co-methyl methcrylate)-co-polymer becomes dissolvable in aqueous solutions at 37° C. can be adjusted, for example, by the percentage of N-acryloyl-N'-ethyl piperazine, for example, between pH 7 and pH 9 with from 52 to 62 mol % of AcrNEP as described in "Solution Properties of Water-Soluble "Smart" Poly(N-acryloyl-N'-ethyl piperazine-co-methyl methacrylate)", G. Roshan Deen, Polymers 2012, 4, 32-45; doi:10.3390/polym4010032. With the poly(MMA-DEAEMA)-, Poly (MMA-DEAMMA)-, and poly(MMA-ArcNEP)copolymers which are dissolvable below a certain pH threshold value a field of application between Ph 2 and Ph 9 can be covered.

In particular with threshold values of pH 7.0 and above that it can be advantageous to replace corresponding poly (MMA-DEAEMA) copolymers with poly(MMA-ArcNEP) copolymers with comparable threshold values, e.g., to achieve higher glass transition temperatures. Thereby a lower risk of the particles sticking together during the coating can be achieved. The execution examples can be modified accordingly.

To be able to adjust fine gradations of the solubility threshold values, special polymers or copolymers with separate monomer ratios do not necessarily have to be synthesized in each case for every coating. In certain ranges an adjustment of the solubility threshold values is also possible by mixture of copolymers with different monomer portions, as for example by mixture of organic spray solutions of Eudragit L and Eudragit S in different weight proportions.

Preferably the used polymers or copolymers contain up to 95% of hydrophobic components, more preferably up to 70%, even more preferably up to 50% and particularly preferably up to 30%.

With the use of grafted polymers these are grafted preferably by 15% to 85%, more preferably by 30% to 70% and particularly preferably by 42% to 60%.

The molecular weights (in Dalton or g/mol) of the used polymers lie preferably above 10000, more preferably above 35000, particularly preferably above 100000 and especially preferably between 150000 and 375000.

It can be also advantageous if the used polymers have rather low molecule weights. For example, this can be advantageous if the layers should be dissolved as quickly as possible after exceedance or undershoot of certain pH values. Preferably the molecule weights (in Dalton or g/mol) of the used polymers lie below 220000, more preferably below 100000, particularly preferably below 40000, even more preferably below 23000 and especially preferably between 15000 and 45000.

The produced layers preferably have a polymer portion of more than 30%, more preferably of more than 50%, particularly preferably more than 70%, and particularly preferably of more than 90%.

The percentage of pH-dependent dissolvable or permeable polymers in the polymer portion of one or several layers amounts preferably to more than 5%, more preferably more than 10%, even more preferably more than 25%, particularly preferably more than 50% and especially preferably more than 80%.

The percentage of plasticizer in proportion to the polymer portion amounts preferably to less than 60 weight percent, more preferably less than 25 weight percent, even more preferably less than 15 weight percent and particularly preferably between 2 and 7 weight percent or between 8 and 13.5 weight percent.

Monomers preferably contained in the polymers of the most inner layer and/or the one or several further layers are acrylic acid, methacrylic acid, diethylaminoethylmethacrylic acid, dimethylaminoethylmethacrylic acid, diethylaminomethylmethacrylic acid, dimethylaminomethylmethacrylic acid, vinyl acetate, diethylaminoacetate, dimethylaminoacetate, glucosamin and preferably at least one of the monomers has a portion in the entire monomers of more than 15% (weight), more preferably more than 25%, even more preferably more than 50%, particularly preferably more than 65% and especially preferably between 45% and 75%. Monomers preferably contained in the polymers of the inner layer and/or the one or several further layers are acrylic acid, methacrylic acid, methylmethacrylic acid, ethacrylic acid, vinylpyrrolidone, vinyl acetate, glucosamin.

Preferably at least one of the used monomers, particularly preferably the lowest molecular used monomer, has a portion in the entire monomers of more than 15% (weight), more preferably more than 25%, even more preferably more than 50%, particularly preferably more than 65% and especially preferably between 45% and 75%.

In order that the pH values, above or below which the used materials become dissolvable or permeable, can be well adjusted, it can be advantageous to use materials whose isoelectric point is not too far away from the aimed threshold value between both states (dissolvable and indissoluble, or permeable and unpermeable).

Therefore, the invention provides in a further preferred embodiment that the used materials, as for example, but not limiting the invention, polymers, copolymers polysaccharides, monomers, etc. have a distance between their isoelectric point and at least one intended threshold value between the dissolvable and indissoluble state, or the permeable and unpermeable state, which is not greater than 6 pH units, preferably not greater than 3 pH units, and particularly preferably not greater than 1.5 pH units.

The mentioned copolymers and monomers represent only examples and should not limit the invention to the use of exactly these, but only serve as examples.

Exemplary realizations are represented in the execution examples 5 and 6. The accompanying diagrams in the FIGS.

7 and 8 show the durability of the individual layers against solutions with certain pH values.

Because the individual layers have to resist the bowel contents surrounding them in the gastrointestinal tract in each case only for a limited time, because, for example, the small intestine passage time admittedly has certain interindividual variations, but does not exceed to few exceptions six hours, a layer or a matrix does not have to be durable at a certain pH factor for boundless time to be considered as not dissolvable, or not permeable for the purposes of this invention. It is sufficient if the layer or matrix protects the underlying layer or the one or more underlying active ingredients against the surrounding solution as long as it is necessary in the course of the bowel passage.

Preferably the layers are, in the range called as durable, indissoluble or not permeable, soluble to no more than 80% of their thickness, more preferably to no more than 65%, even more preferably to no more than 50%, particularly preferably to no more than 35%, or are not permeable for more than 50% of the active ingredients, preferably not for more than 30%, more preferably not for more than 10%, particularly preferably for not more than 5%, namely preferred within a time span of more than one hour, more preferred longer than 2 hours, even more preferred longer than 3 hours, particularly preferred longer than 4 hours. Various methods are available to the person skilled in the art to adjust the solubility or permeability of a layer, in particular also the duration up to a sufficient dissolution or the reaching of a sufficient permeability or the duration of a suitable durability by variation of the portions of the components of that layer, as for example plasticizer, pore former, further polymers or copolymers, further pharmaceutical auxiliary materials (excipients) their thickness, particle size etc.

Also options are known to the person skilled in the art to accelerate the dissolution of a layer becoming permeable or dissolvable, for example, by an additional layer arranged under this layer with a disintegrant which already swells with low permeability of the overlying layer and thereby caused contact with the surrounding solution and blows off the layer which has become permeable.

An exemplary layer sequence is shown in FIG. 4.

An acceleration of the dissolution can also be achieved in that a disintegrant is incorporated directly into the functional layer, which is why this is provided in a further embodiment of the invention. Exemplary realizations of such layers are found in the literature known to the person skilled in the art, for example, in "Pulsatile drug delivery to ileo-colonic segments by structured incorporation of disintegrants in pH-responsive polymer coatings.", Schellekens et al., Journal of Controlled Release, 2008.

To the person skilled in the art also different options are known to influence the swelling behaviour of the used materials or material mixtures. For example, hydrophilic, hydrophobic or amphiphilic materials can be added. Further polymers, copolymers, film-forming substances, fillers or other accordingly suitable excipients can be also used. Ester of fatty acids, e.g. decaglycerin monopalmitic acid ester, but also ethylcellulose, microcrystalline cellulose, polymethylmethacrylates are exemplary mentioned. Which materials can be used for this, among others, as well as instructions for the easy determination of the purposeful quantity proportions, the person skilled in the art can take from the accordingly appropriate literature. Examples for this would be US20050220861 (e.g., use of ethylcellulose), US 2010/0047323 (e.g., use of esters of palmitic acid) and the documents mentioned there.

Execution example 5c shows a preferred embodiment.

A further option to influence swelling properties and dissolution properties of a layer consists in the reprotonation or deprotonation of the layer, or at least of its superficial portions, which is why the invention provides this in a further embodiment. For example, a layer made of a cationic polymer which was dissolved by means of an acid can still contain small portions of the corresponding acid even after the completion of the film-formation and drying which can lead to the fact that the layer swells or becomes partially dissolved even if it is surrounded by an aqueous solution whose pH value still lies above the pH value below which it should become dissolvable or permeable.

The remained residuals of the acid can be removed or be converted to salts by an aftertreatment of the layer with an alkaline buffer solution, so that they can cause no relevant shift of the inner pH value.

An exemplary implementation would be the aftertreatment of the layers made from an acetic acid-containing solution from different presented execution examples with a 0.1-molar phosphate buffer with a pH value of one ph unit above the pH value below which the corresponding layer should become dissolvable. The particles to be after-treated (capsules, tablets, pellets etc.) are immersed for 5 to 20 seconds into the aftertreatment-solution or are sprayed with it. Then the aftertreatment-solution is removed by immersion of the particles in (or spraying with) deionized water, and the particle are dried.

The pH value of such an aftertreatment-solution can be also higher between 0.5 and 3 pH units. Preferably it is higher between 0.8 and 2 pH units. In some cases differences greater than 3 pH units also make sense. The optimum pH value, the optimum molar concentration of the aftertreatment-solution and the duration of the aftertreatment for the individual application can be determined by simple dissolution tests of the layers after-treated. According to coating thickness and process an aftertreatment time of up to 10 minutes or beyond that can also be necessary to achieve the desired dissolution behavior of the layer.

After application of the aftertreatment-solution this is rinsed with deionised water and the after-treated layer is dried.

Suitable realization possibilities are also shown in the execution examples 20 and 21.

Like with the cationic polymers which can be used for the layer formation when they are dissolved in acids and with which mainly alkaline solutions are used for the aftertreatment of the produced layers, mainly acidic solutions can be used for the aftertreatment with anionic polymers which can be used when dissolved in alkaline solutions.

For example, layers which were produced from polymers which were dissolved in water with the help of ammonium salts (e.g., ammonium hydroxide), can be after-treated with buffer solutions which have a pH value, that lies 0.5 to 3 pH units, preferably 1 to 2 pH units, particularly preferably 1.5 pH units below the pH value above which the layers to be after-treated should dissolve or become permeable. The determination of the optimum pH values, the molar concentrations and the aftertreatment times is made as described above.

Also layers which are produced using materials which have anionic, as well as cationic properties, a reprotonation and/or deprotonation can be carried out according to the used solution. The solutions or buffers used for that have pH values which preferably lie within the range within which the corresponding layer should be durable. A further option to improve the swelling behavior and dissolution behavior particularly that of chitosan-containing layers consists in the use of carbonic acid as a solvent for the Chitosan. On account of the increased volatility of carbonic acid compared with many other acids, it is possible to produce chitosan-containing layers which have lower residual concentrations of solvent, and thereby show fewer tendencies to swell in contact with aqueous solutions above their pH threshold value below which they become dissolvable. The processes for the production of Chitosan-containing layers shown in the execution examples can, with small modifications, also be carried out with carbonic acid instead of acetic acid. The used solutions should be kept under exposure to $CO_2$ (in the pressure tank with $CO_2$ pretension or by constant blowing in of $CO_2$ into the solution container) up to the use if possible and preferably also during the spray process. With coating processes in the granulator and other powder layering processes with which the film formation takes place more slowly, the equipment, if necessary, is to be exposed to a controlled $CO_2$ atmosphere in order to achieve an even evaporation of the water and the $CO_2$ dissolved in it, so that the dissolved Chitosan does not precipitate before onset of the film formation.

If necessary the concentrations of the used solutions have to be adjusted in order to obtain solutions with desired viscosities. Accordingly the applied quantities of the solutions are to be adjusted) to achieve the desired application quantities of polymer. The preparation of suitable Chitosan solutions can be carried out, for example, like described in "A Novel Method of Dissolving Chitosan in Water for Industrial Application", Yasuo SAKAI et al., Polymer Journal, Vol. 33, No. 8, pp 640-642 (2001), or "Chitosan-Coating of Cellulosic Materials Using an Aqueous Chitosan-$CO_2$ Solution", Yasuo SAKAI et al., Polymer Journal, Vol. 34, No. 3, pp 144-148 (2002). The application of carbonic acid as a solvent can also be used with other materials with cationic properties.

An acceleration of the dissolution can also be achieved, while, for example, underneath the layer becoming dissolvable or permeable dependent on Ph an additional layer is arranged which is dissolvable or swellable in aqueous solutions, and which by solution or swelling releases substances which can change the pH value of the solution in the closer surrounding, and therefore can contribute to a quicker dissolution of the overlying layer. A further preferred embodiment of the invention uses this option. For example, below a layer which should dissolve as quickly as possible below a certain pH value (for example, made by use of Kollicoat Smartseal 30D or Chitosan), a water-soluble polymer layer is arranged (e.g. based on hydroxypropylmethylcellulose) in which a substance is embedded which is likely to lower the pH value of the surrounding solution, for example, citric acid, acetic acid, hydrochloric acid etc.

An exemplary realization is represented by execution example 7. The accompanying diagram in FIG. 9 shows the durability of the individual layers against solutions with certain pH values.

A further preferred embodiment of the invention provides that the layer under which such an accelerating layer is arranged becomes permeable enough to let the accelerating layer become effective, only if the pH value of the surrounding solution has undershot either the defined lower, or first pH value, or has exceeded the defined upper or last pH value, or has closely approached the mentioned defined pH values, so that the activation of the accelerating layer does not take place because of time-dependent diffusion of water molecules through the overlying layer, at least not when the surrounding pH value is in the range, in which the overlying layer should be durable, and preferably not during time span, in which the overlying layer should be durable.

Because the increase of the pH value within the small intestine takes place more slowly than the drop with the transit of the ileocecal valve, and therefore with exceedance of the defined upper pH value of a layer, the layer is exposed longer to the solution with this pH value than to a solution which undershoots the lower pH value it is not critical if the dissolution of the layer is accelerated only with undershoot of the defined lower pH value, so basically from the underlying layer only substances decreasing the pH value are released. Therefore, the invention provides this in a further preferred embodiment.

There are also substances known which by contact with the surrounding solution participate in chemical reactions with it, and by this way, for example, by a further change of the pH factor contribute to a quicker dissolution of the Ph-sensitive layer or it becoming permeable quicker.

For example, such interlayers are described in US2010/0129446A1.

A further option to accelerate the dissolution of pH-sensitive layers is the at least partial neutralization of the polymer dispersions, like, among the rest, it is described in EP0978275A1, EP1906939A2 and EP1848751B1. This technology can also be used with the present invention to realize suitable further preferred embodiments. Also the coating processes described in EP0978275A1 and EP1848751B1 can be used for the realization of layers with which certain embodiments of the invention can be carried out, in each case if necessary with exchange of the polymers or copolymers against such ones that have the desired pH-dependent solubility properties or swellability properties.

A further preferred embodiment of the invention provides that the formulation contains one or several additional interlayers which are suitable to reduce or avoid interactions and/or incompatibilities between the layers between which they are arranged or between the most inner layer and the one or more active ingredients or the one or more active-ingredient containing cores. For this purpose this embodiment of the invention uses, for example, suitable polymers and if necessary other pharmaceutical excipients as for example plasticizers, anti-adhesives, etc. The polymers can be, for example, water-soluble polymers like HPMC or PVP.

This layer or layers can be realized similar to the already mentioned layers for the accelerated release, however, without accordingly active substances which modulate, for example, the pH value of the surrounding solution or have particular swelling properties.

A further preferred embodiment of the invention provides, to combine these interlayers which shall avoid incompatibilities or interactions with the release-accelerating properties, while they also contain accordingly active substances which modulate, for example, the pH value of the surrounding solution or have particular swelling properties.

In order to avoid or minimize interactions or incompatibilities between the one or more active ingredients or the one or more active-ingredient containing cores and the functional layers an interlayer, or if necessary also several of them can be applied, with or without one or several release-accelerating ingredients, also directly on the one or more active ingredients or the one or more active-ingredient containing cores, what is provided in a further preferred embodiment of the invention. A corresponding layer can be e.g. also used to seal the gap between both capsule halves with the use of capsules.

Additional interlayers can also have properties which are dependent on the pH value of the bowel contents surrounding them, for example, for the compensation of pH-dependent solubility properties of one or several active ingredients. Preferably such additional interlayers do not have such pH-dependent properties as they are described for the one or several further layers.

The materials, or material mixtures which are used for the coatings, dispersions, emulsifications or compressions can also contain further excipients, for example, the excipients mentioned in appropriate pharmacopoeias (e.g., Ph. Eur., USP, JP).

Suitable are, among others, plasticizer, separating agents, flavorings, wetting agents, dyes, neutralization agents, preservatives, pore formers, antioxidants, lubricants, anti-tacking agents, sweeteners, etc. Descriptions of these substances can, for example, be taken from "Lexikon der Hilfsstoffe für Pharmazie, Kosmetik and angrenzende Gebiete", Fiedler, H. P.

By use of such techniques, a further preferred embodiment of the invention causes a particularly quick dissolution of the layers, and thus a particularly quick release of the one or more active ingredients after the passage of the ileocecal valve, preferably already up to more than 30% before the first flexure, with suitable adjustment of the coating thicknesses preferably more than 50% before it. Especially dissolvable active ingredients, or active ingredients which are applied onto or into disintegrant-containing cores, are released even up to more than 75% before the first flexure.

In a further preferred embodiment the invention provides that the further layer or one or several further layers are realized, while for their production a mixture of several materials is used from which at least one is dissolvable or permeable below the defined lower pH value of the respective layer, and at least one other above the defined upper pH value.

With the production of the layer these materials are arranged effectively in parallel, so that one of the materials becoming dissolvable or permeable causes a sufficient solubility or permeability of the layer.

A further preferred embodiment of the invention realizes this with a mixture of several dispersions with which the single dispersions contain in each case dispersion particles which have certain durabilities against aqueous solutions with special pH values.

For example, 2 dispersions are mixed with which the first dispersion contains polymer particles which are dissolvable above a certain pH value (e.g., a poly(MMA-AA) copolymer), while the second dispersion contains polymer particles which are dissolvable below a certain pH value (e.g. a poly(MMA-DEAEMA) copolymer).

A layer made by means of the mixed dispersion is dissolvable above a defined upper pH value, as well as below a defined lower pH value and it is durable in the range between the both defined pH values (a schematic section of such a layer is shown in FIG. 5, layer C2).

Exemplary realizations are shown in the execution examples 9a and 9b. The accompanying diagrams in FIG. 11 show the durability of the individual layers against solutions with certain pH values.

In a further preferred embodiment of the invention this can be carried out, for example, by the use of dispersion with accordingly large dispersed particles as for example flakes which are distributed statistically in a way that they at least simply overlap over the whole surface to be coated, so that a closed layer is created, however, that not over the whole surface an overlapping of both materials occurs, but it is possible at least in a part of the layer that an aqueous solution whose pH value allows it to dissolve or make permeable at least one of the materials can penetrate through this layer.

For the production of these dispersion particles, for example, the same or similar polymers and copolymers can be used as they are also used for the production of the protective coatings or enteric coatings known in the state-of-the-art. Also ungrafted Chitosan polymers or ones grafted with anionic molecule groups can be used. So it is possible to carry out the invention, without acrylates being required. Also without the use of phtalates the invention is realizable.

Some examples for the production of suitable polymers and dispersions based on them, as well as options for the modifications of single parameters can be taken, e.g., from WO 2009/016258A1.

Also in "Entwicklung eines lösungsmittelfreien Befilmungsverfahrens für feste Arzneiformen", Engelmann S., Dissertation, Freiburg im Breisgau, Albert-Ludwigs-Universität, 2004, suitable processes for the production of polymers and modification of their properties are described. As well in WO/2005/115352.

Further options for the production of such polymers are also described in EP1496870B1, EP0704207A2, EP0704207A2.

With the production of coating solutions with different polymer particles, e.g., with the mixing of 2 or more dispersions with polymer particles of different solubility properties, with which polymers with anionic, as well as polymers with cationic properties are used, under circumstances premature agglutination of the polymer particles or partial or entire swelling or dissolution of polymer particles can occur.

This is prevented or minimized by a further preferred embodiment of the invention with which the dispersions are brought to roughly the same pH value before mixing them by addition of substances which are likely to change the pH value of the dispersions, for example, acids or bases, as for example citric acid, hydrochloric acid, ammonia, NaOH, KOH, ammonium hydroxide or organic bases, as for example triethanolamine etc.

This is already realized in the examples 9a and 9b.

Preferably the pH value of the individual dispersions is, as possible, not changed so much that the dispersion particles become dissolvable, or only so much that none or only a tolerable swelling occurs. This can also result in a certain distance between the pH values of the dispersions to be mixed and it is possible by simple solubility tests to find the optimum pH values.

In a further preferred embodiment of the invention the dispersions to be mixed are adjusted in their pH factor, as well as in their buffer capacity so that the pH value resulting after the mixture is located between the isoelectric points of the used polymers as possible, preferably as centrally in between as possible. If individual used polymers have a significantly higher solubility or swellability, at this pH value, than others, the pH value of the mixture can also be adjusted in such a way that all used polymers are equally durable as possible.

The adjustment of the pH value of the mixture can take place instead of or in addition to the adjustment of the dispersions to be mixed also by addition of suitable substances with or after the mixture.

If not all used polymers are durable with the pH value realized in the mixture, it can be advantageous to mix the individual dispersions only shortly before the use for the production of the coating, so that possibly no entire dissolution of the particles or only a tolerable swelling occurs. This represents a further preferred embodiment of the invention.

If all polymers to be used are dispersible in a solution in which none is dissolvable or swellable above a tolerable amount, a suitable dispersion can also be produced directly from predried powders of redispersible polymer particles without producing two or more different dispersions beforehand and then mixing them.

Depending on the used polymers it can be difficult to impossible to produce a mixed dispersion, e.g. if no pH value can be found with which all used polymers are durable enough at least for the time between mixture of the dispersions and initial drying on the substrate to be coated.

Therefore, a further preferred embodiment of the invention provides that two dispersions are prepared and are sprayed onto the substrates to be coated out of different nozzles at the same time.

In a further preferred embodiment of the invention the different dispersions are sprayed out of separate nozzles, so that they meet only in the coating equipment, preferably only shortly before the contact and particularly preferably only with the contact with the particles to be coated, as for example tablets, pellets, capsules or similar. This prevents a premature dissolution or agglutination of the dispersion particles. Especially well suited for such processes are coating pans or fluidized-bed-equipment like they are also used in the execution examples. The equipment of coating systems with separate spray devices is described in the state-of-the-art several times.

A further preferred embodiment of the invention realizes the geometrically parallel arrangement of the different materials for the production of layers which are durable only in a range between a defined lower pH value and a defined upper pH value, by the fact that the particles to be coated, as for example capsules, pellets, tablets or similar, are partially dipped for a certain time into solutions, dispersions, emulsions or other liquid or fluidized media which contain the materials or at least partially consist of them. During the dipping a portion of the medium sticks onto the particles and forms an according layer after taking the one or more particles out of the medium, preferably by drying, polymerization, gelation, hardening or other kinds of film-formation. After completion of the film-formation of the first material to be used all materials to be used are used subsequently. Partial dipping takes place with different materials in each case with changed geometrical orientation of the particle and only after the layer-formation after the respectively preceding dipping process is completed at least to a large extent, so that the individual materials do not interact, or at least do not interact so far that the solubility properties or swellability properties would be changed significantly.

Preferably the areas in which different materials or material mixtures are applied abut directly. More preferably the according areas overlap, particularly preferably by more than 10% of their surface area, especially preferably by more than 25% of their surface area. A possible embodiment is shown in execution example 14, a further one is shown in execution example 21.

A further preferred embodiment of the invention realizes the geometrically parallel arrangement of the different materials for the production of layers which are durable only in a range between a defined lower pH value and a defined upper pH value, by the use of differently coated capsule halves, or of capsule halves which are made of different materials. For example, the capsule bottom (partially also called as capsule body) is coated with a material, or made of such a material which is dissolvable or permeable with values below a defined lower pH value. The capsule lid is coated with a material, or made of such a material which is dissolvable or permeable with values above a defined upper pH value. Preferably a sealing of the resulting gap is carried out after the filling and fitting together both capsule halves for which suitable processes are known to the person skilled in the art from the state of the art (e.g., dispensation of a not water-soluble polymer in the form of a solution or dispersion).

For the coating of capsule halves different known processes can be used, for example, the dip-coating, as also described in U.S. Ser. No. 12/845,994 or US 2011/0033530 A1, or also spray coating or powder layering processes.

Particularly with the spray coating several different materials or material mixtures can also be applied effectively in parallel onto a capsule half, e.g. while certain areas are protected by shadow masks from the contact with the spray mist, or the different materials are sprayed on from different directions. Thereby it is possible to achieve a particularly quick and very even dissolution of the capsule.

The use of the shadow masks which are arranged between the spray device and the surface to be coated and which allow the spray mist to hit the surface only at the places at which they have suitable openings, is not limited to the coating of capsules, but can also take place with other administration forms, as for example tablets, pellets, dragée etc.

Preferably the shadow masks consist of steel sheet, particularly preferably of stainless steel sheet. The shadow masks can be coated with separating agents on their side turned to the spray device which makes easier the following cleaning from the spray mist captured above the areas of the surface to be shaded. Preferably the shadow masks are adapted to the geometry of the administration form, so that over a possibly large part of the surface an as low as possible distance to the surface is made possible in order to avoid spraying behind of the shaded areas as far as possible.

By use of different capsule sizes it is possible to arrange several such layers sequentially, while in each case a smaller capsule which is composed of correspondingly coated or produced capsule halves is introduced into a larger capsule whose capsule halves are dissolvable according to the demands for the corresponding layer.

An exemplary implementation is shown in execution example 19.

If a particularly quick release is desired, a disintegrant or super-disintegrant, for example, Explotab, can be introduced into the capsule bottoms and/or capsule caps before the transfer of the capsules into the respectively larger capsule. This also causes a better exposure of the introduced capsule if only one capsule half of the encasing capsule dissolves.

With the mixture of different dispersions or with the coating with different dispersions out of several nozzles or multi-substance nozzles, it is often advantageous to add one or several stabilizers and/or emulsifiers, or to increase the amount compared to the stabilizers and/or emulsifiers used with a single dispersion. An according further preferred embodiment of the invention is shown in execution example 9f.

With many embodiments of the invention basically also solutions of suitable polymers can be used instead of dispersions, for example, dissolved in organic solvents or as colloidal solutions. For example, Eudragit E in a colloidal solution with stearic acid, which is why the invention provides this as further preferred embodiments.

A further option to process materials which can not be processed together in dissolved, dispersed or moist condition, consists in the processing of these materials in dry or mostly dry condition.

Therefore, in a further preferred embodiment the invention provides to produce one or several layers from different particles, preferably polymer particles or copolymer particles, with different solubility properties, while a dry coating process is applied. With a dry coating process the polymer particles are mixed without addition of solvents, and are then applied onto the substrate to be coated. During the application of the particles a plasticizer is also added (with a spray process, e.g., from a separate spray nozzle, in some cases also chronologically staggered with respect to the application of the particles) which allows a congregation and/or sticking of the particles, so that a film-formation can start. If necessary small quantities of solvents are used which, however, cannot dissolve the polymer particles because of the small quantity, at least not completely. Under circumstances a thermal after-treatment process (curing) is necessary, where appropriate after the addition of small quantities of solvent (for example, water, isopropanol, etc.), for a sufficient film-formation.

Exemplary realizations are shown in the execution examples to 9c and 9d. The accompanying diagrams in the FIGS. 12 and 13 show the durability of the individual layers against solutions with certain pH values.

Accordingly usable processes are, for example, also described in "Dry coating: an innovative enteric coating method using a cellulose derivative", Sakae Obara, European Journal of Pharmaceutics and Biopharmaceutics 47 (1999). In this publication known processes are described, e.g., also known to the person skilled in the art, which allow a finding of the optimum process parameters and excipients, even if polymers are used which are based on other monomers.

It is especially advantageous if with such a process at least one of the used polymers is already softened at low temperatures and/or becomes malleable with low quantities of water, as for example hydroxypropyl-methylcellulose-acetate-succinate (HPMCAS). A further preferred embodiment of the invention uses a polymer basing on that. Another example of a polymer with accordingly low glass transition temperature is Eudragit E (Evonik, Darmstadt).

Acrylate based polymer mixtures which can not be reliably processed with the described process or other polymers difficultly mixable in dispersed state, can be processed, for example, with the dry coating process which is described in "Einfluss von Formulierungsparametern auf den Powder Layering and Dry Coating Prozess im Rotorgranulator", Jeannine Ebert, Saarbrücken. Instead of powders from a single polymer different polymers are mixed in powder form and then are processed with the dry-coating processes known to the person skilled in the art. The according publications also give instructions for the modification of the processes to achieve desired properties.

Also in "Entwicklung eines lösungsmittelfreien Befilmungsverfahrens für feste Arzneiformen", Engelmann S., Dissertation, Freiburg im Breisgau, Albert-Ludwigs-Universität, 2004, suitable processes for the dry-coating are described.

Further options for the realization of a dry-coating process are described in "PARTICLE COATING USING DRY POWDER TECHNOLOGY", L. Bilancetti, PARTEC 2007.

In "Dry polymer powder coating and comparison with conventional liquid-based coatings for Eudragit® RS, ethylcellulose and shellac", European Journal of Pharmaceutics and Biopharmaceutics, Pearnchob and Bodmeier described dry coating processes, where small proportions of water are added to the plasticizer mixture, in the year 2003.

However, these low percentages of water do not affect disadvantageously the use of polymers with different solution properties or Ionic properties which are mixed as a powder, because the contact with the water as a solvent takes place only directly with the coating process.

Also the dry coating processes described in "A novel powder coating process for attaining taste masking and moisture protective films applied to tablets", Matteo Cerea et al., International Journal of Pharmaceutics 279 (2004) can be used after replacement of the used polymers and if necessary modification of process parameters like processing temperature, plasticizer percentage etc. The mentioned publications give sufficient instructions for the person skilled in the art to adapt the processes to the according polymers, copolymers or other film-forming materials to be used, and to optimize if necessary by simple experiments.

A further preferred embodiment of the invention realizes the parallel arrangement of the materials by a geometrically defined application of the materials, or of coatings with according properties. For this purpose the coating materials are sprayed on or applied in another way subsequently or from different directions onto the possibly already precoated units, as for example particles, powders, pellets, tablets, capsules or similar where it is ensured that in each case not the whole surface is coated, so that the surface per used material has at least one area in which only this one must become dissolvable or permeable to let the surrounding aqueous solution come into contact with the next layer that is arranged further inside.

This is realized, for example, by the directed spray with solutions or dispersions of the different materials from different directions, or by several consecutive coating processes between which the coating substrate or the coating device is turned, flipped over or is otherwise changed in the geometrical arrangement. (FIG. 6).

Exemplary realizations of this embodiment are represented in the execution examples 10 and 11. The accompanying diagrams in the FIGS. 14 and 15 show the durability of the single layers compared with solutions with certain pH values.

The effectively parallel arrangement of the materials can also be realized with the use of mixtures from solutions and dispersions, respectively emulsions or also powders, be it that this mixing takes place before an application step, during this, or thereafter, which is why a further preferred embodiment of the invention provides this.

For example, the materials which are not dissolvable in organic solvents can be dispersed in these or one of those, while other materials are already dissolved in it, or are dissolved therein after the production of the dispersion. The dispersion can also be prepared in an aqueous medium and be transferred afterwards into an organic solvent or solvent mixture.

Exemplarily the production of a Chitosan dispersion from Chitosan dissolved in diluted acetic acid is mentioned (for example, by adding a sodium tripolyphosphate solution after the addition of a stabilizer or emulsifier, as for example polysorbate 80) which is transferred afterwards into a mixture of acetone and isopropanol wherein Eudragit S 100 is dissolved.

Instead of preparing the mixture before the application, a mixing can also be carried out directly with the process, for example, by the use of several spray nozzles or three-component nozzles by which the amount of the required emulsifier can be reduced.

Also the materials can be processed in different physical states. In this manner one of the materials or material mixtures can be present as a powder, while the other material or material mixture is introduced in the process as solution or dispersion. Execution example 16 shows a possible realization.

Among the rest, examples and tips to usable processes and process parameters are also to be found in "Multiparticulate Chitosan-Dispersed System for Drug Delivery", SHIMONO et al., Chem. Pharm. Bull. 51(6) 620-624 (2003), "Chitosan dispersed system for colon-specific drug delivery", SHIMONO et al., International Journal of Pharmaceutics 245 (2002) 45/54 or U.S. Pat. No. 7,604,820 B1. The used not water-soluble Eudragit polymers can be replaced by pH value dependent dissolvable polymers. If necessary the quantitative proportions are to be adapted to be able to adjust desired viscosity and further excipients like emulsifiers or separating agents to be added, e.g., to avoid sticking together of the particles what are everyday tasks for the person skilled in the art.

Also different functional particles can be used, for example, powders from anionic and cationic polymers which are embedded in a layer whose primarily film-forming polymers then may also be not water-soluble. The processes from the above-mentioned publications can be modified, for example, accordingly in such a way that the Chitosanpowder is replaced by such a mixture of several polymer powders. For example, the amount of the used Chitosan of powder is halved, and a HPMCAS powder or a powder made of Eudragit S is added, so that the original powder amount is achieved again. The HPMCAS powder or the Eudragit S powder is adjusted to the same particle size (e.g., approx. 95 μm diameter).

A further exemplary realization is shown in execution example 15.

Among the rest, such processes which use solid and more or less liquid components for the coating in one process are also called as "Powder Layering", and are sufficiently described in the state-of-the-art (e.g., in "Einfluss von Formulierungsparametern auf den Powder Layering and Dry Coating Prozess im Rotorgranulator", Jeannine Ebert, Saarbrücken). Hence, to the person skilled in the art various options through which parameter changes he can adjust the desired layer properties are also known.

Whether the more or less liquid components are used only as binder (e.g., in execution example 15), or are responsible even for functional properties of the achieved layers (e.g., in execution example 16), is widely unimportant for the coating process itself.

According to solubility properties of the used powders, it is advantageous particularly with powder layering process to replace organic binder or polymer solutions by corresponding aqueous dispersions.

Powders layering processes can be also used if materials are available which are dissolvable or permeable above a certain upper pH value, as well as below a certain lower pH value. Because then no effectively parallel arrangement of different functional materials is necessary, certain layers of the formulation can be produced according to the ECDS pellets or the capsules, described in "Multiparticulate Chitosan-Dispersed System for Drug Delivery" or "Chitosan dispersed system for colon-specific drug delivery", while, however, the Chitosan powder used there is replaced, by a powder made of one or several of the above-mentioned materials.

An exemplary realization is shown execution example 36.

A further preferred embodiment of the invention provides that such materials are, in addition, sensitive to enzymes which can be formed in the large intestine by microorganisms. Especially advantageous in this embodiment it is that a material can become dissolvable, permeable or degraded with undershoot of a certain lower pH value, as well as with exceedance of a certain upper pH value, as well as also with availability of a sufficient amount in enzymes available in the large intestine, and therefore preferably can serve as the sole material of a layer controlling the release. The material used in the above-mentioned execution example meets, for example, all these properties.

In a further preferred embodiment of the invention it is provided that such a material has, in addition, film-forming properties, so that an additional film-forming material can be renounced with the production of a layer.

A further preferred embodiment of the invention provides to realize the parallel arrangement by preparation of a matrix, with which particles with different solubility respectively permeability properties are mixed intensively with the particle to be enclosed or to be coated and then are compressed. For example, active-ingredient containing and pre-coated micropellets are mixed with at least two different powders and at least one powder is made of a polymer or copolymer which becomes dissolvable or permeable below a defined lower pH value, and at least one other powder made of a polymer or copolymer which becomes dissolvable or permeable above a defined upper pH value. Due to the intensive mixing the different polymer particles are evenly distributed, so that with onset of the solubility or permeability of one kind of powder the whole matrix is weakened in its structure and is dissolved, respectively permeable.

Example 13 describes a corresponding realization option.

Before the mixing and compressing excipients can be added as well, preferably those which the person skilled in the art usually uses with the compression of tablets.

Two possible sources for faulty release behavior with the use of parallel arrangement of different materials are:
1. The unintentional entire coating with one material, so that no way is possible for a liquid through the layer which makes only the other material dissolvable or permeable, or
2. a not completely closed layer, so that any liquid can come to contact with the underlying layer. With relatively low occurrence rate first-mentioned failure is not dramatic, because this way only a small dose reduction occurs, if a multiparticular administration form is chosen (e.g., capsule with coated pellets). However, second-mentioned failure can lead to unintentional premature release and therefore, perhaps, to systemic exposition.

However, in such a way faultily coated units can be sorted out. For this purpose the invention provides in a further preferred embodiment, to expose the units after the layer-producing process step which can be a coating, compression, dispersion or emulsification to an aqueous solution, against which the produced layer is durable, if it was formed correctly, however, against which the underlying layer is dissolvable or permeable, so that accordingly faultily coated units are dissolved, respectively their active ingredients can be released and are separated. Where required several such steps are necessary, with different solutions which do not dissolve the correctly produced layer or make it permeable, however, if applicable successively all underlying layers.

Exemplary realizations for this embodiment of the invention are shown in the execution examples 8a and 8b. The accompanying diagrams in FIG. 10 show the durability of the individual layers compared with solutions with certain pH values.

Particularly with the realization of the layers between the inner layer and the one ore more active ingredients or the one or more active-ingredient containing cores or between the inner and most inner layer it has turned out advantageous to arrange additional interlayers between the individual pH dependent layers, which are generally dissolvable in aqueous media, to let the aqueous solution come into good contact with the next inner layer also in the cases in which strong overlappings with the different materials are given and, therefore, perhaps, only small areas of the layer become permeable or dissolvable.

It is especially advantageous if this layer contains one or several chemical compounds which experience a strong volume increase in contact with water or aqueous solutions, e.g., the disintegrants of which to the person skilled in the art several different ones are known, for example (croscarmellose, crospovidon, polyvinylpyrrolidone (e.g., Kollidon), sodium-starch-glycolate (e.g., Explotab®, Vivastar®)). Corresponding layers and their production are known to the person skilled in the art, for example, from EP0210540.

The overlying layer is blown off by the great increase in volume, as soon as water or an aqueous solution penetrates through a part of this overlying layer that has become dissolvable or permeable with which the subsequent layer is exposed to it, as widespread as possible (example 12).

Such layers contain preferably more than 3% of disintegrants, more preferably more than 6% of disintegrants, even more preferably more than 15% of disintegrants and particularly preferably more than 25% of disintegrants.

Because the materials of which the different layers are composed respectively from which the matrixes or envelopments are produced, have different permeabilities, dissolution speeds, swelling abilities and other characteristics, it is advantageous to produce the different layers in different coating thickness or different surface weights (g/cm$^2$) or different total weight gain (in the state-of-the-art partially also referred to as a total weight gain (TWG)), respectively build up the matrixes from differently sized particles, which is why a further preferred embodiment of the invention provides this.

Many materials which preferably become permeable or dissolvable below a certain pH value, also have certain swelling abilities above this pH value what can cause a certain undesirable permeability which can be counteracted by a larger application quantity with the coating process or by the use of larger particles with the compressing.

Therefore, a further preferred embodiment of the invention provides that materials which are dissolvable preferably in the acidic range and/or are increased permeable particularly in the acidic range or material mixtures which comprise them, are used in a larger layer thickness and/or in the form of larger particles, than those which are dissolvable or are increased permeable preferably in the neutral or basic range.

With the use of material mixtures which rather contain materials that are rather acid-dissolvable, as well as ones that are rather dissolvable in the basic or neutral area, be it as a mixture of solutions, dispersions, emulsions, powders, as successively applied effectively in parallel arranged layers or further described implementations, a further preferred embodiment of the invention provides, that the weight and/or volume percentages, the particle size, the coating thicknesses, the kind and amount of the used excipients and other parameters which influence the properties are adjusted differently, so that dissolution behavior, permeability characteristics, release behavior and durability below and above the corresponding pH threshold values are as desired.

For example, it is advantageous to adjust the amount of the functional polymers of an acid-dissolvable chitosan-containing part layer lower than that of the HPMCAS containing part layer which shall be dissolvable in the neutral pH range, because with the same mass percentage the chitosan-containing part layer would swell and become permeable faster, what can be undesirable.

Another example is a lower coating thickness of a layer of a combination of Chitosan and ethylcellulose, if necessary together with other excipients, compared with a layer which consists of Eudragit FS 30D (also if necessary with other excipients, as for example triethyl citrate etc.). By the amount of ethylcellulose which desirably reduces the swelling behavior of the layer in the neutral range, the dissolution speed of the layer in the acidic range slows down, which is why a lower coating thickness can be necessary, in order to adjust the dissolution speed in the acidic range to the dissolution speed of the Eudragit FS 30D in the neutral to alkaline range.

The processability of materials with different properties, for example, rather acid-dissolvable materials together with rather base-dissolvable materials, anionic polymers or copolymers with cationic polymers or copolymers etc., may be difficult under circumstances if these materials interact with each other. For example, anionic and cationic polymers can form interpoly electrolyte complexes (IPEC) which have undesirable solubility properties.

This can be reduced, on the one hand, by the already described methods, as for example, the addition of suitable emulsifiers, the processing of the polymers and/or copolymers in the unsolved and not dispersed condition, among others with the dry-coating techniques (dry powder coating), or by the fact that the different materials only come to contact for a short time in dissolved or dispersed condition, as for example, with the application in the spray process from separate nozzles or from three-compound nozzles, or if the materials are introduced into the process in different physical states, as for example with the separate supply as a solution or dispersion and as a powder in the tablet coater or granulator.

On the other hand, the processability, and also the functionality of the coatings can be improved, also by the fact that a direct contact of the different materials is reduced or avoided, in that the particles used which are made of different materials, be they determined for the production of dispersions or also for dry-coating processes or to the compression of matrixes, are or become enveloped in a layer which prevents the interaction to a large extent, which is why a further preferred embodiment of the invention provides this.

This can be, for example, a thin layer of non water-soluble polymers which has sufficient permeability, so that the ions responsible for the pH value in the intestinal contents can interact with the functional polymers, but an interaction of the polymer chains of the other materials used during the coating process does not take place.

Suitable polymers are, for example, ethylcellulose and amylose. Further polymers with corresponding properties are known to the person skilled in the art (e.g., polymers usually utilized for retard-coatings like Eudragit RS, Eudragit RL, Eudragit NE, etc.).

The thickness of the coating which is necessary for this purpose usually lies under the coating thickness which is used for a delayed active ingredient release.

By using Eudragit NE above the functional Eudragit S layer of Carboxymethylcellulose-based (AcDiSol®) microspheres or micropellets a coating thickness of 12 µm turned out to be advantageous.

Also onto particles (powder particles, microspheres, micropellets etc.), which are used for dry-coating processes or for the mixed processing of liquid (dispersions, solutions etc.) and solid materials or material mixtures, such layers can be applied in order to prevent interactions between the different materials as far as necessary.

To determine the layer thickness suitable for the respective application, test batches with different layer thicknesses can be manufactured and their dissolution behavior can be tested. Usually, with an insufficient functional dissolution (e.g., in an acidic or slightly basic pH range) the layer thickness is to be reduced and it is to be increased with an increased solubility in the middle pH range which can point to the formation of IPEC or with premature coagulation during the coating process.

Such a coating of the particles used can be also used together with the further described methods, such as for example the dry-coating processes or the mixed use of solid (powders) and liquefied (solutions, dispersions, emulsions) materials.

For example, the particles used in the execution examples 8a, 8, 9c, 9d, 13 or 15 can be covered before their use in the respective coating process with such a thin polymer layer. Preferably, this is applied in a fluidized bed process and also other coating processes known in the state-of-the-art can be used, as for example emulsion evaporation processes or solution evaporation processes.

Execution example 16 shows a possible realization variant.

Because particularly after the exit from the stomach greater fluctuations or overshoots of the pH value can occur, for example, if larger amounts of bicarbonate are introduced into the intestine by digestive juices, it can be advantageous, to form the first layer which should become dissolvable or permeable after the passage of the stomach in such a way that this process takes longer than a certain time or is delayed by at least a certain time, so that underlying layers come into contact with the intestinal contents to a relevant extent only if the fluctuations or overshoots have faded away as much as possible.

It turned out that such overshoots, which in some cases can reach pH values of 6.5 or more, have often faded away within 20 minutes, in some cases only after about 40 minutes, in few cases, however, can continue up to one hour.

Therefore, a further preferred embodiment of the invention provides, that the inner layer is carried out in such a way that it is dissolved or becomes permeable within a interval between 15 and 120 minutes with appropriate pH values above the pH value above which it can become dissolvable or permeable (the defined last pH value of this layer), preferable between 25 and 90 minutes, more preferable between 40 and 70 minutes or particularly preferable between 50 and 60 minutes.

A similar behavior can also be achieved in a further provided preferential embodiment of the invention by the fact that below the inner layer an additional layer or layer sequence is arranged which dissolves or becomes permeable after a certain time largely independent of the pH value, so that the underlying layer is uncovered, respectively is exposed to the intestinal contents, delayed, even if the inner layer dissolves or becomes permeable rapidly after the passage of the stomach. The intended times apply accordingly also with this embodiment.

An exemplary implementation of this embodiment is a variation of the execution example 11 with which the coating made of Eudragit L 100 is carried out in a thickness of 20 mg/cm$^2$.

A further exemplary implementation modifies execution example 12 to the effect that before the coating with Eudragit L 100 takes place at first an additional layer made of 85% HPMC (Pharmacoat 606), 5% talc and 10% croscarmellose, and then a thin layer made of Eudragit 30D is applied. After dissolution of the layer made of Eudragit L water diffuses through the permeable layer made of Eudragit NE into the underlying disintegrant-containing layer which swells after one hour to such an extent that the permeable layer is blown off, and the underlying layer is exposed sequence. Appropriate layer constructions are known to the person skilled in the art. For example, "Development of pulsatile multiparticulate drug delivery system coated with aqueous dispersion Aquacoat ECD.", Mohamad A, Dashevsky A., Int J Pharm. 2006 Aug. 2; 318(1-2):124-31. Epub 2006 Apr. 3, is mentioned. Here, e.g., an alternative possible construction of such a delaying layer sequence is shown.

A further preferred embodiment of the invention provides to use a hot-melt process, be it as a spray process like in US2011250244 or in a melt extrusion process, at least with the production of a layer.

With a spray process the layer- or matrix-forming material or material mixture is heated up above its melting temperature and then is processed like a solution or dispersion.

With the melt extrusion process the active-ingredient containing cores are provided, if applicable already provided with one or several precoatings, are heated up together with the material or material mixture, so that at least the layer- or matrix-forming material or material mixture is heated up above its melting temperature, flows around the cores and thus controls the release accordingly.

The result of the extrusion can be provided with additional layers for which purpose the extrudate can be processed, for example, into pellets. Multiple coatings also can be realized in this way by corresponding choice of the materials and their melting points. Potentially provided further coatings of the extrudates can also be processed with the other processes deducible from the listed examples, as well as with further processes which are known to the person skilled in the art from the state-of-the-art.

For the production of the coatings, which are applied for the realization of the different embodiments of the invention, solution and vaporization processes can also be used in further preferred embodiments (solvent evaporation methods, respectively emulsion solvent evaporation methods) as they are described, e.g., in "Polymer-coated microparticles for the sustained release of nitrofurantoin", Jita Liu et al., "Enteric Micro-Particles for Targeted Oral Drug Delivery", Annalisa Dalmoro et al., or "Handbook of Pharmaceutical Controlled Release Technology", D. L. Wise. Preferably such processes are used, if especially small particle are to be coated (e.g., microspheres) and/or if the desired coating thicknesses are especially low, for example preferably with coating thicknesses from less than 30 µm, more preferably with coating thicknesses under 20 µm, particularly preferably with coating thicknesses between 7 and 15 µm.

Among the rest, with the production of functional layers or matrixes made of or with portions of solid or widely solid materials, for example, with dry powder coating processes, with the use of dispersions or with processes which deploy solid and liquid materials combined, as for example also in "Chitosan dispersed system for colon-specific drug delivery", or also with the use of dispersions, the functional properties of the layers or matrixes can be adjusted by the size of the used particles. For this purpose, for example, homogeneous particle size distributions can be used, as well as heterogeneous ones. A further preferred embodiment of the invention provides to select the distribution of the particle sizes in such a way that these lie within an order of magnitude, so the ratio of the smallest to the largest particle is smaller than 10. Preferably this ratio is smaller than 4, more preferably smaller than 2 and particularly preferably smaller than 1.4. With very homogeneous distributions steadier functional properties of the layers or matrixes arise over the entire surface, respectively the entire volume.

Further advantages can be achieved with some embodiments if the size of the particle does not differ too much from the average coating thickness of the layer to be produced. Good successes are achieved if the average particle diameters lie between 10% and 180% of the intended average coating thicknesses. This can be especially advantageously with the production of layers in the powder layering process. If this ratio approaches to 95%, the functionality of the layer, measured in the ratio of the permeability or solubility in the different aqueous solutions in which a high solubility or permeability is rather desirable, respectively rather undesirable, can improve.

Therefore, the invention provides in a further preferred embodiment, that the particle have average diameters of 10% to 180% of the coating thickness, preferable 20% to 150%, more preferable 40% to 130%, particularly preferable 60% to 115% and especially preferable 90% to 110%.

To further improve the dissolution properties of the layers or matrixes, the invention provides in a further preferred embodiment, that at least a part of the used particles are constructed heterolithic instead of monolithic, as for example with a simple powder., Among the rest, exemplary implementation are coated pellets or granulate materials or other particle forms. In the state-of-the-art such particles in some cases are also called heterogeneous.

Execution example 30 shows an exemplary realization option.

Such heterolithic particle can consist, for example, of a water-soluble core, as for example sugar pellets, HPMC granulate material, spray-dried microspheres etc., which is coated with a material which has solubility or permeability dependent on the pH value.

The core can also contain swelling agents, disintegrants, so-called distintegrants and/or Superdisintegrants, or can consist of them, in order to optimize the dissolution properties of the layers to be produced with the particles.

The processing can then be carried out similar to the already identified publications of SHIMONO et al., in that the Chitosan used there is replaced by accordingly coated particles, where particles with one kind of functional coating can be used, as well as mixtures with particles which are coated differently, for example, those which become dissolvable above a certain pH value together with such ones which become dissolvable below a certain, preferably lower pH value and even other, if necessary also in different kind functionalized particles can be added, for example, in general water-soluble particles, not dissolvable particles, especially very swellable particles and/or bacterially degradable coated particles.

These particles or corresponding mixtures can also become compressed, if necessary with additions of further excipients, to tablets, minitablets or microtablets, or also wet-granulated or melt-granulated.

With regard to the compression and other kinds of processing measures are known to the person skilled in the art how he can achieve that the functional coatings remain intact even during the compression or other processing. This concerns, for example, the choice of the core materials, among the rest, with regard to the compressibility, the elasticity module etc., the addition of suitable plasticizers to the coating materials, and some more.

Corresponding recipes and formulation instructions are to be found in the corresponding technical literature, in brochures of the appropriate manufacturers (e.g., Evonik, Darmstadt) and in published patent documents.

Implementation options are shown in the execution examples 17 and 18.

A further preferred embodiment of the invention provides, that one or several further layers, the most inner layer or the most inner layer as well as one or several of the layers arranged above that, can become dissolvable or permeable dependent not only on the pH value, but that these are, in addition, also sensitive against bacterial enzymes, so that a release can be carried out in the large intestine even without corresponding drop of the pH value if appropriate bacterial enzymes are released there.

Exemplary implementations are shown in the execution examples 1b, 1c, 3, 4, 5, 6, 7, 8a, 8b, 9a-e and 10. At place of Chitosan also other bacterially degradable polymers can be used, for example, guar, amylose, and pectin. Then, if necessary, another polymer must be added, which restores the dependence of the layer on the pH value of the aqueous solution surrounding it. With the described and implied embodiments of the invention with a most inner layer with which the defined second pH value of the most inner layer is at least as high as the pH value at most in the gastrointestinal tract to be expected and preferably is at least as high as the pH value at most to be expected in the small intestine, it is ensured that of the one or more active ingredients, or one or more active-ingredient containing cores are not released, as long as the pH value of the surrounding aqueous solution rises monotonously, because after the dissolution of each layer, or after it becomes permeable, the next layer is released, or exposed to the aqueous solution which becomes dissolvable or permeable with monotonously rising pH values only with even higher pH values which continues, until the most inner layer is reached which does not dissolve at all towards higher pH values, in any case, not within the higher pH values which do not exceed the pH value maximally to be expected in the gastrointestinal tract, and preferably not within higher pH values which do not exceed the pH value maximally to be expected in the small intestine.

Because, however, with not monotonously rising pH value, i.e., if the pH value decreases after exceedance of the last pH value of the inner layer, and therefore after the dissolution of that layer or it becoming permeable, namely below the defined lower pH value of the layer whose defined upper pH value was not yet exceeded or below the defined first pH value of the most inner layer, this layer becomes dissolvable or permeable, all still present layers become dissolvable or permeable at that time, because their defined lower or defined first pH value is also undershot therefore, so that with an appropriate drop of the pH value the one or more active ingredients or the one or more active ingredient containing cores are released.

With the described and implied embodiments of the invention without a most inner layer, or with those where the defined second pH value of the most inner layer is lower than the pH value maximally to be expected in the small intestine, the one or more active ingredients or one or more active-ingredient containing cores are also not released, as long as the pH value of the surrounding aqueous solution rises monotonously, however, only as long as the defined upper pH value of the farthest inside lying further layer or the defined second pH value of the most inner layer is not exceeded. After a corresponding exceedance the release is triggered with these embodiments. The release with not monotonously increasing pH values corresponds to the embodiments with a most inner layer with which the defined second pH value of the most inner layer is at least as high, as the pH value maximally to be expected in the small intestine.

Because no bacterial enzymes are necessary for the release in the large intestine, therefore, a preferred embodiment of the invention provides a formulation for the specific release of one or more active ingredients or one or more active-ingredient containing cores within the digestive tract, with which the release is not directly triggered by the presence of bacterial enzymes in the surrounding medium. More preferred for the realization of the coatings or the in other forms implemented envelopments no materials are used which are indissoluble in the area between pH 5 and pH 8 and at the same time are sensitive enough to enzymes of large intestine bacteria to allow a release of the active ingredients being triggered by such enzymes.

Because the drop of the pH value in the digestive tract after reaching of the ileocecal valve occurs regardless of the inner composition of the oral administration form, the invention provides a further preferred embodiment with which the dissolution of individual or several used materials or them becoming permeable does not depend on the fact that the active-ingredient containing core contains acids or acid releasing substances.

It is provided in a further preferred embodiment of the invention, that to the one or more active ingredients or the one or more active-ingredient containing cores a substance is added which increases the pH value of the latter, and that the pH value is preferably adjusted to between pH 3 and pH 8, more preferably to between pH 4 and pH 7, particularly preferably to between pH 5 and pH 6. The pH value then preferably lies relatively centered in the range to be expected in the gastrointestinal tract, in which also preferably lie the threshold values between solubility and insolubility, respectively permeability and no permeability, of the used layers.

Also a further preferred embodiment is provided with which at least one active ingredient or at least one material which is comprised by or contained in one or more active ingredient containing cores, can increase the pH value of an aqueous solution, provided that this aqueous solution itself has a pH value of below 3, preferably a pH value in the range of below 5, particularly preferably a pH value of below 7.

The risk of an unintentional absorption in the small intestine is kept extremely low by the very reliable release of the active ingredients only after reaching of the large intestine, which is why the invention is particularly suited to administer one or several active ingredients which are toxic with unintentional release in the small intestine in the used amount or cause undesirable effects which worsen the benefit-risk ratio.

Therefore, a further preferred embodiment of the invention provides to use the described formulation for the administration of one or more such active ingredients. For example, the invention is used for the administration by immunosuppressive active ingredients, steroids, corticosteroids, heavy metals, cytostatics, cytotoxic active ingredients, prednisolone, budesonide, MAO-inhibitors.

Because the influence of digestive enzymes on the one or more active ingredients to be administered is minimized by the release in the large intestine, the invention particularly recommends to administer such substances by means of the described formulation which are sensitively to the conditions in the upper digestive tract, for example, peptides, vaccines and hormones.

Further substances which the invention provides as active ingredients and which can be released targeted individually as well as in combination of two or more active ingredients by means of the invention and its embodiments are, for example:

Acebutolol, acetylcysteine, acetylsalicylic acid, acyclovir, alprazolam, alfacalcidol, allantoin, allopurinol, ambroxol, amikacin, amiloride, aminoacetic acid, amiodarone, amitriptyline, amlodipine, amoxicillin, ampicillin, ascorbic acid, aspartame, astemizole, atenolol, beclomethasone, benserazide, benzalkoniumhydrochloride, benzocaine, benzoic acid, Betamethasone, bezafibrate, biotin, biperiden, bisoprolol, bromazepam, bromhexine, bromocriptine, budesonide, bufexamac, buflomedil, buspirone, caffeine, camphor, captopril, carbamazepine, carbidopa, carboplatin, cefachlor, cefalexin, cefadroxil, cefazolin, cefixime, cefotaxime, ceftazidime, ceftriaxone, cefuroxime, selegiline, chloramphenicol, chlorhexidine, chlorpheniramine, chlortalidone, choline, cyclosporin, cilastatin, cimetidine, ciprofloxacin, Cisapride, cisplatin, clarithromycin, clavulanic acid, clomipramine, clonazepam, clonidine, clotrimazole, codeine, cholestyramine, cromoglycic acid, cyanocobalamin, cyproterone, desogestrel, dexamethasone, dexpanthenol, dextromethorphan, dextropropoxiphenes, diazepam, diclofenac, digoxin, dihydrocodeine, dihydroergotamine, dihydroergotoxin, diltiazem, diphenhydramine, dipyridamole, dipyrone, disopyramide, domperidone, dopamine, doxycycline, Enalapril, ephedrine, epinephrin, ergocalciferol, ergotamine, erythromycin, estradiol, ethinylestradiol, etoposide, Eucalyptus globulus, famotidine, felodipine, fenofibrate, fenoterol, fentanyl, flavin mononucleotide, fluconazole, flunarizine, fluorouracil, fluoxetine, flurbiprofen, furosemide, gallopamil, gemfibrozil, gentamicin, Gingko biloba, glibenclamide, glipizide, clozapine, Glycyrrhiza glabra, griseofulvin, guaifenesin, haloperidol, heparin, hyaluronic acid, Hydrochlorothiazide, hydrocodone, hydrocortisone, hydromorphone, ipratropium hydroxide, ibuprofen, imipenem, indomethacin, iohexol, iopamidol, isosorbide dinitrate, isosorbide mononitrate, isotretinoin, ketotifen, ketoconazole, ketoprofen, ketorolac, labetalol, lactulose, lecithin, levocarnitine, levodopa, levoglutamide, levonorgestrel, levothyroxine, lidocaine, lipase, imipramine, lisinopril, loperamide, lorazepam, lovastatin, medroxyprogesterone, menthol, methotrexate, methyldopa, methylprednisolone, metoclopramide, metoprolol, miconazole, midazolam, minocycline, minoxidil, misoprostol, morphine, multivitamin mixtures or combinations and mineral salts, n-methylephedrine, naftidrofuryl, naproxens, neomycin, nicardipine, nicergoline, nicotinamide, nicotine, nicotinic acid, nifedipine, Nimodipine, nitrazepam, nitrendipine, nizatidine, norethisterone, norfloxacin, norgestrel, nortriptyline, nystatin, ofloxacin, omeprazole, ondansetron, pancreatin, panthenol, pantothenic acid, paracetamol, penicillin g, penicillin v, phenobarbital, pentoxifylline, phenoxymethylpenicillin, phenylephrine, phenylpropanolamine, phenytoin, piroxicam, polymyxin b, povidone-iodine, pravastatin, prazepam, prazosin, prednisolone, prednisone, bromocriptine, propafenone, propranolol, proxyphylline, pseudoephedrine, pyridoxine, quinidine, ramipril, ranitidine, reserpine, retinol, riboflavin, rifampicin, rutoside, saccharin, salbutamol, salcatonin, salicylic acid, simvastatin, somatropin, sotalol, spironolactone, sucralfate, sulbactam, sulfamethoxazole, sulfasalazine, sulpiride, tamoxifen, tegafur, teprenone, terazosin, terbutaline, terfenadine, tetracycline, theophylline, thiamine, ticlopidine, timolol, tranexamic acid, tretinoin, triamcinolone acetonide, Triamterenes, trimethoprim, troxerutin, uracil, valproic acid, vancomycin, verapamil, vitamin e, folinic acid, zidovudine, somatostatin, insulin, calcitonin, vasopressin, gastrin, EGF (epidermal growth factor).alpha.-hANP (.alpha.-human atrial natriuretic peptide), enkephalin, endorphin, GM-CSF (GRANULOCYTE MACROPHAGE COLONY-STIMULATING FACTOR), G-CSF (GRANULOCYTE COLONY-STIMULATING FACTOR), humanly growth hormones, glucagon, t Pa (tissue plasminogen activator), TNF (TUMOR NECROSIS FACTOR), TCGF (T cell growth factor), ACTH (ADRENOCORTICOTROPHIC HORMONE), interleukins, interferon, EPO (ERYTHROPOIETIN), urokinase, neocarnostatin, bradykinin, immunoglobulin and its digestion product, various allergens and their digestion products, ketoprofen, ibuprofen, diclofenac, indometacin, ketrolac, fenbufen, loxoprofen, tenidap, piroxicam, tenoxicam, salazosulfapyridine, pipethanate hydrochloride, mepenzolate bromide, and sennosides A and B.

The invention provides in a further preferred embodiment that the one or more active ingredients are included in the formulation in a safe and effective amount. Because with the administration of one or more active ingredients by means of the different embodiments of the invention the safety is increased, or the risk of undesirable effects is reduced, compared to administration forms which release the one or more active ingredients in the large intestine only with a lower reliability a further preferred embodiment of the invention provides that the amount of the comprised active ingredients is up to 20% higher, preferably up to 50% higher and further preferably more than 50% higher than with administration forms which release the one or more active ingredients in the large intestine not reliably.

The use of the described but also of other active ingredients in one of the administration form described or suggested in the different embodiments of this invention is suited in particular for the treatment of inflammatory intestinal diseases, as for example, ulcerative colitis or Crohn's disease, of neurological disturbances, as for example, depressions or attention deficit disorders, of metabolism disturbances as, for example, diabetes, of neoplastic diseases as, for example colorectal carcinomas, which is why the invention provides such uses in further preferred embodiments.

The one ore more active-ingredient containing cores may already have release-controlling properties, as, for example, coatings with retarding properties, matrices with sustained release properties, use of cores made of biodegradable materials, which is why the invention provides in further preferred embodiments to also use such cores with all shown embodiments and with embodiments realizable by combination of different preferred possibilities of embodiment.

In a further preferred embodiment of the invention it is dispensed with the production of the most inner layer, so that the first layer applied on the one or more active ingredients or the one or more active ingredient containing cores, which has pH-dependent solubility or permeability characteristics according to the described inner, most inner or further layers, is the one or one of the described further layers.

In a further preferred embodiment this layer has a defined upper pH value which is not higher than the highest pH value which is expected in the small intestine with the target group.

In a further preferred embodiment the defined upper pH value of this layer is lower than the highest pH value which is expected in the small intestine with the target group, namely preferably so much lower that with the individuals with whom the pH value maximally to be expected in the small intestine is reached, this layer is dissolved sufficiently or has become permeable at the earliest if the ileocecal valve is reached.

This is achieved, for example, by the fact that the pH value above which the layer becomes dissolvable or permeable is reached in the small intestine of the individuals of the target group at maximum a certain time before the reaching of the ileocecal valve and the time, which is required at the achieved pH value until this layer has become dissolved or permeable enough to release the one or more active ingredients or the one or more active ingredient containing cores, is at least as long as the above-mentioned maximum time.

In a further preferred embodiment a layer is arranged below this layer, with geometrically parallel arranged layers preferably below the part layer which is dissolvable or permeable with higher pH values, which is dissolved or becomes permeable time-delayed, in order that the corresponding temporal conditions are fulfilled.

Such an embodiment is realized in the example 14 which should not limit the embodiment, however, to this realization option. Also example 38 shows a possible realization.

Preferably the time-delayed dissolvable layer dissolves within an interval of more than 10 minutes, more preferably within more than 20 minutes, particularly preferably within more than 45 minutes. The interval amounts preferably no more than 60 minutes, more preferably no more than 40 minutes and particularly preferably no more than 25 minutes. A layer becoming permeable enough time-delayed becomes permeable enough preferably after the same intervals. Preferably the above-mentioned intervals also correspond to the time before reaching of the large intestine beginning from which in the target group at the earliest the defined upper pH value of the farthest inside situated further layer is exceeded. By this delay it can be achieved that the farthest inside situated further layer does not have to be dissolvable especially slowly, so that it also results in a release if its defined upper pH value is exceeded only very shortly before reaching of the large intestine. Particularly preferably these intervals serve as a definition for "short" in the expression "shortly before the reaching of the large intestine" in terms of different embodiments of the invention.

With the embodiments with which the further layer or the further layers are realized by effectively parallel arranged part layers, of which at least one first part layer becomes dissolvable or permeable above a defined upper pH value, and at least one second part layer below a defined lower pH value, the parts of the layer arranged directly above the first part layer which becomes dissolvable or permeable above a defined pH value, and the parts of the layer arranged directly under the second part layer which become dissolvable or permeable below a defined pH value, do not substantially contribute to the release dependent on the course of the pH value. The parts of the layer arranged directly above the first part layer, which become dissolvable or permeable above a defined pH value, become, by the fact that their defined upper pH value lies lower than the one of the first part layer, dissolvable or permeable before this first part layer anyway.

The parts of the layer arranged directly under the second part layer, which become dissolvable or permeable below a defined pH value, become, by the fact that their defined lower pH value lies higher than the one of the second part layer, dissolvable or permeable as soon as this one has become dissolvable or permeable anyway, without a further change of the pH value being required.

Exemplarily it is assumed an administration form which consists of a most inner layer which becomes dissolvable below pH 6.0, a further layer which consists of effectively parallel arranged material mixtures, of which the one becomes dissolvable below pH 5.5, the other above pH 6.5, and an inner layer which becomes dissolvable above pH 6.0. If the effectively parallel arrangement of the material mixtures of the further layer is realized by geometrically lying side by side (effectively parallel) implementation of part layers, the part of the most inner layer, which lies below the part layer consisting of the material mixture which is soluble below pH 5.5, is not required because it also dissolves immediately after the dissolution of the overlying part layer of the further layer. Likewise, the part of the inner layer, which lies above the part layer with the material mixture which is soluble above pH 6.5, is not required because it is durable only in a pH range in which the underlying part layer of the further layer is also durable and, therefore, does not contribute to the functionality.

Therefore, a further preferred embodiment of the invention provides, not to form one or several of these parts of one or several corresponding layers or to remove them after the formation. In order to not form such layer parts, the corresponding ranges can be covered, for example, with the application of the layers or part layers, for example, by arrangement of shadow masks while spraying of layer-forming solutions. However, corresponding areas can be also be spared with other kinds of the geometrically defined formation of layers, for example, by defined incomplete dipping into layer-forming solutions or dispersions.

If parts of the layers, which become dissolvable or permeable above a certain upper pH value, are arranged directly underneath a part layer, which becomes dissolvable or permeable below a defined lower pH value, at least in the area in which these overlap, one of both layers is not substantially for the release dependent on the course of the pH value, which is why the invention provides in a further preferred embodiment not to form one of both layers in the overlapping area or to remove it after the formation.

In a further preferred embodiment of the invention part layers or parts of layers which are not formed according to the above-mentioned variants or are removed after the formation, become formed or are not removed at least in the edge area of the overlapping, in order to avoid an unintentional release if the parts of the respective layers or the part layers and other layers or part layers do not abut or merge gapless, for example, on the basis of manufacturing tolerances or if an overlapping is desirable.

In a further preferred embodiment one or several areas in which part layers with different sensitivities to pH values of aqueous solutions abut, are covered by application of materials or material mixtures indissoluble in aqueous solutions. Exemplarily administration forms are mentioned with which corresponding part layers are applied onto capsule bodies and capsule caps, and with which the joint or the gap originating while fitting together the capsule halves is sealed by means of banderolization or by means of introduction of a non water-soluble polymer.

A further option to release to the one or more active ingredients or one or more active-ingredient containing cores reliably with the reaching of the large intestine even if the drop of the pH value by the entry into the large intestine is lower than the interindividual variability of the maximal pH value in the small intestine, consists of the effectively parallel arrangement of two or more layer sequences of inner and most inner layers in each case with or without further layers, which is why the invention provides this in a further preferred embodiment.

This effectively parallel arrangement of layer sequences can be realized similar to the parallel arrangement of different materials or material mixtures for the production of the further layer or layers described in the above-mentioned embodiments.

For example, the parallel arrangement can be carried out by geometrically defined application of the layer sequences, as, for example, by spraying on the layer sequences from different directions, by masking of certain areas using shadow masks or by separate production of the layer sequences and subsequent mechanically parallel arrangement. Also the effectively parallel arrangement can be carried out, in that particles, for example, powder particles or microspheres, are coated with corresponding layer sequences and these are then arranged effectively in parallel, for example, by compression of active-ingredient containing particles with a mixture of particles coated with different layer sequences or by the use of particles coated with different layer sequences in powder layering processes.

Through the effectively parallel arrangement of these layer sequences, the dissolution of one of these layer sequences or the fact that one of them becomes permeable, causes that the intestinal contents come into contact with one or more of the active ingredients or one or more of the active-ingredient containing cores, and the one or more active ingredients can be released.

The individual layer sequences consist in each case of an inner layer which becomes dissolvable or permeable above the defined last pH value and a most inner layer which becomes dissolvable or permeable below a defined first pH value and the most inner layer is arranged in a way that it is exposed to the intestinal contents only when the inner layer has become dissolvable or permeable.

Between the most inner and the inner layer the individual layer sequences can contain one or more further layers as they already are described in the above-mentioned embodiments of the invention.

Each of these individual layer sequences enables the intestinal contents to get into contact with the underlying structure, which can usually consist of one or more active ingredients, one or more active-ingredient containing cores, but also of additional functional or non-functional layers, as soon as a certain pH value was exceed and afterwards the pH value has decreased below a certain pH value or by a certain pH value.

Thereby it is possible that also a small drop of the pH value can be used to controlledly release one or more active ingredients.

A single layer sequence without further layers enables this only if the maximum pH value reached in small intestine is higher than the defined last pH value of its inner layer but not higher than the sum of the defined first pH value of its most inner layer and of the drop of the pH value upon the entry into the large intestine, therefore only within a certain range of pH values.

The certain range of pH values within which the individual layer sequences enable the release with the drop of the pH value by a certain value can be adjusted by the adaptation of the defined first and last pH values of their most inner and inner layers. The range of an individual layer sequence is smaller than the value by which the pH value must maximally drop to reliably initiate a release by the distance of the defined first pH value of the most inner layer from the defined last pH value of the inner layer.

The range of pH values in which the one or more active ingredients or the one or more active ingredient containing cores are released can be enlarged by the effectively parallel arrangement of two or more such layer sequences with differently adjusted ranges, so that it is not necessary for a reliable release that the drop of the pH value upon the entry into the large intestine is greater than the interindividual variability of the pH value maximally achieved in the small intestine.

The range of pH values in which an individual layer sequence ensures the release with the drop of the pH value can be enlarged by use of further layers between the inner and most inner layers with one or several of the respective layer sequences, like they are also described with the embodiments of the invention which use only one individual layer sequence, so that less layer sequences arranged in parallel are necessary or with the same number of layer sequences arranged in parallel the range of pH values in which the formulation can be used can be enlarged, which is why a further preferred embodiment of the invention provides this.

The effectively parallel arrangement of two or more layer sequences with further layers enables, to use a lower number of further layers with the individual layer sequences, than would be required with the use of a single layer sequence.

Preferably the ranges of the individual layer sequences are adjusted so that they connect to each other, which is why the invention provides this in a further preferred embodiment. In a further, even more preferred embodiment the invention provides that the individual layer sequences are realized in such a way that the ranges slightly overlap, to ensure that no gaps appear between the ranges even with the appearance of manufacturing tolerances.

Also with the effectively parallel arrangement of two or more layer sequences it can be advantageous to choose the defined second pH value of the most inner layer smaller than the maximum expected pH value in the small intestine within the target group or to omit the formation of the most inner layer at least with one of the layer sequences, which is why the invention provides this in further preferred embodiments. With such embodiments a release can also be achieved if the pH value increases above a certain value, namely either above the above-mentioned defined second pH value, the defined upper pH value of the farthest inside arranged further layer of the layer sequence without a most inner layer, or the defined upper pH value of the inner layer of that layer sequence which has neither a most inner layer, nor a further layer. In further preferred embodiments of the invention, most inner layers of layer sequences whose defined first pH value is higher can be arranged, in addition, also below layer sequences with lower defined first pH values, or can extend underneath them, in order to simplify the effectively parallel arrangement of the individual layer sequences.

Likewise inner layers of layer sequences, whose defined last pH value is lower, in addition, be arranged also above layer sequences with higher defined first pH values, or extend across them as shown in execution example 24.

Corresponding arrangements or extensions can be carried out in each case over the entire surface of the administration, or only over certain subareas. Also with the realization of one or more further layers, corresponding extensions are possible and provided with further preferred embodiments of the invention.

The effectively parallel arrangement of layer sequences can also be carried out in a mix with the serial arrangement of inner, most inner and further layers.

Exemplary realizations of some embodiments are shown in the execution examples from 22 to 24.

With the described embodiments and with variations accordingly modifiable by the person skilled in the art it can be ensured that the amount not released before the passage of the ileocecal valve preferably is released to more than 30% before the passage of the first flexure of the large intestine, more preferably that it is released to more than 50% before the passage of the first flexure of the large intestine, particularly preferably that it is released to more than 75% before the passage of the first flexure of the large intestine.

The described embodiments of the invention are, inter alia, suitable to produce multiparticular administration forms, which is why multiparticular administration forms with the described features represent a further preferred embodiment of the invention.

In particular the described embodiments of the invention are suitable to provide single-unit administration forms, because even longer retention times of these administration forms before the ileocecal valve, as they can occasionally occur with non-multiparticular administration forms, do not lead to a premature release, because a sufficiently large drop of the pH value occurs only after the passage of the ileocecal valve. Particularly preferably for single-unit administration forms embodiments are used which have a most inner layer whose defined second pH value is at least as high, as the maximum expected pH value in the small intestine.

With correspondingly preferred embodiments of the invention it can be achieved that before reaching the large intestine maximum 50% of the one or more active ingredients are released, preferably maximum 30%, more preferably maximum 10%, particularly preferably maximum 5% and especially preferably maximum 1%.

The features of the invention can also be used in combinations which are not explicitly mentioned in examples, but are regarded as preferred embodiments of the invention. Depending on the concrete definition of tasks it can be purposeful to implement some features in their particularly preferable arrangements, but possibly not to form other optional features at all. The present description, the listed and referenced publications and the execution examples enables the person skilled in the art to apply the described features also in further meaningful combinations taking into account its specialist knowledge and the appropriate technical literature, as well as to modify the exemplarily shown ways of realization in order to bring various properties into ranges more advantageous to its concrete application.

Suitable processes can be also taken from the following writings in order to be able to produce the described layers: Bauer, Lehman, Osterwald, Rothgang "Coated Pharmaceutical Dosage Forms", 1998, Wissenschaftliche Verlagsgesellschaft mbH Stuttgart and CRC Press LCC, Boca Raton, Fla., USA or McGinity, "Aqueous Polymeric Coatings for Pharmaceutical Dosage Forms, Second Edition, Revised and Expanded", 1997, Marcel Dekker Inc., New York, USA.

The following execution examples demonstrate some embodiments of the invention. However, the invention and the accordingly described variants should not be limited to these embodiments.

EXECUTION EXAMPLES

Preparation of the active ingredients, respectively the active-ingredient containing cores 1. Hard Gelatin Capsules with Probiotic Filling Lyophilized *Escherichia coli* (100000 CFUs), 200 mg of lactose, 50 mg of microcrystalline cellulose and 20 mg of magnesium stearate are mixed and filled into hard gelatin capsules of the size 2.

2. a. Prednisolone-Coated Pellets

Nonpareille pellet cores from microcrystalline cellulose are coated with prednisolone in the fluidized bed coater.

2. b. Prednisolone-Containing Microtablets (in the State-of-the-Art Partially Also Referred to as Minitablets)

Prednisolone, lactose, hydroxypropylmethylcellulose and magnesium stearate are mixed in the ratio 8:2:6:1 and are compressed into convex microtablets with a diameter of 1.5 mm and a thickness of 1.2 mm.

2. C. Prednisolone-Containing Micropellets

Prednisolone, microcrystalline cellulose, hydroxypropylmethylcellulose and magnesium stearate are mixed in the ratio 8:2:6:1 into an aqueous solution. Then micropellets are produced in the spray drying process from this solution.

3. Tungsten-Coated Pellets

Nonpareille pellet cores made of microcrystalline cellulose are coated in the fluidized bed coater with sodium tungstate from an aqueous sodium tungstate solution.

Example 4

Hard gelatin capsules with probiotic filling are coated like in example 5 but the first coating with the ungrafted Chitosan is not carried out.

After the stomach passage the middle layer is dissolved if the pH value exceeds 6 in the duodenum or jejunum. If the pH value further increases, until it exceeds Ph 7, shortly before the reaching of the large intestine the grafted Chitosan becomes dissolvable and the capsule contents is released at the beginning of the large intestine. Though with a lower course of the pH value Ph 6 is also exceed, however, only in the course of the ileum where the middle layer dissolves. After the passage of the ileocecal valve the pH value drops below 5 whereby the grafted Chitosan gets soluble and the release is triggered.

The capsules are determined for the oral administration where the at last applied layer is dissolved in the stomach, the second to last applied layer in the small intestine, after the pH value has risen above 6, and the first applied layer if either Ph 5 is undershot, or Ph 7 is exceeded. The operating range extends from pH 6 to approx. pH 7.5. The tolerance against fluctuations of the pH value within the small intestine amounts to one pH unit.

After the passage of the ileocecal valve, 80% of the active ingredient is released within the large intestine.

Example 5

Hard gelatin capsules with probiotic filling are coated with Chitosan.

For this purpose a 2% aqueous solution is produced of the Chitosan which is deacetylated to 90%, after acetic acid was added to the water, in an amount that the molar equivalent based on the amino groups of the Chitosan is 1.9.

Then decaglycerin monopalmitic acid ester is added, in an amount of 15 weight percent of the amount of the Chitosan. The mixture is stirred until a uniform Chitosan solution has resulted. The coating is carried out with a Hicoater HC-LABO.

The application quantity amounts to 4 mg/cm$^2$. This coating is dissolvable with a pH factor below 6.5.

Then a coating with Chitosan, which is grafted to an extent of 30% with chlorogenic acid, and which is indissoluble in the Ph range from 5 to 7, but dissolvable above Ph 7 and below Ph 5, is carried out The coating corresponds to the first coating, although the Chitosan deacetylated to 90% is grafted with chlorogenic acid to an extent of 30% before the preparation of the coating solution. The grafting is carried out like in "Enzymatic Grafting of a Natural Product onto Chitosan to Confer Water Solubility Under Basic Conditions".

The application quantity is adjusted to 6.5 mg/cm$^2$.

Then the coated capsules are coated once more with an enteric coating based on Eudragit L 100, with the following composition of the spray suspension:

11.3% Eudragit L 100, 3.7% talc, 5.6% triethyl citrate, 3.8% 1N NH3 (1.7% NH3), and water. The coating thickness is 5 mg/cm$^2$. This coating is dissolvable with a pH value of above 6.

Then one more coating is carried out with Kollicoat Smartseal 30D in an Aeromatic Streal with a supply air temperature of 55° and a spray rate of 8 g/min with a pressure of 1.5 bar and a nozzle diameter of 0.8 mm. In the course of this the product temperature remains below 40°, the coating thickness is 4.5 mg/cm$^2$. The drying is carried out for 5 minutes with 55° and for further approx. 10 minutes with 45° until the outlet temperature reaches 40°.

The spray suspension contains 33.33% Kollicoat Smartseal 30D, 1.5% tributylcitrate, 0.1% of butylated hydroxytoluene, 6% of talc and as remaining ingredient water.

This coating is dissolvable with a pH value of up to 5.5.

The capsules are determined for the oral administration where the at last applied layer dissolves in the stomach, the second to last applied layer in the small intestine after the pH value has risen above 6, the next layer if either Ph 5 is undershot, or Ph 7 is exceed, and the first applied layer finally in the cecum, as soon as the pH value drops below 6.5, or as soon as the preceding layer had dissolved after the drop below Ph 5.

Example 5b

Hard gelatin capsules with probiotic filling are coated like in example 5 but the first coating is, however, carried out just like the last coating (process and coating materials like coating 4 in example 5).

The capsules are determined for the oral administration where the at last applied layer is dissolved in the stomach, the second to last applied layer in the small intestine, after the pH value has risen above 6, the next layer if either Ph 5 is undershot or Ph 7 is exceeded, and the first applied layer finally in the cecum, as soon as the pH factor drops below 5.5, or immediately after the preceding layer had been dissolved with the drop below Ph 5.

Example 5c

Hard gelatin capsules with probiotic filling are coated with a poly(MMA-DEAEMA) copolymer. The copolymer and the spray solution made from it, as well as the coating process correspond to the last coating from example 5 although with the preparation of the copolymer the percentage of DEAEMA is increased compared to the normal Kollicoat Smartseal 30D, so that the copolymer already becomes dissolvable with undershoot of a pH value of 6.0 (layer C, FIG. 6).

Then a coating with Chitosan which is grafted with chlorogenic acid to an extent of 30%, and which is indissoluble or only a little and slowly dissolvable in a pH range of 5 to 7, but is dissolvable above pH 7 and below pH 5 is carried out.

For this purpose from Chitosan which is deacetylated to 90% is grafted with chlorogenic acid to an extent of 30%. The grafting is carried out like in "Enzymatic Grafting of a Natural Product onto Chitosan to Confer Water Solubility Under Basic Conditions".

A 2% aqueous solution is prepared from this grafted Chitosan, after acetic acid was added to the water, in an amount that the molar equivalent based on the amino groups of the Chitosan is 1.5.

Surelease (ethylcellulose, Colorcon, Harleysville USA) is diluted 1:1 with water. The Surelease solution and the Chitosan solution are mixed in a ratio of 1:1 (w/w) and stirred until a uniformly intermixing is achieved.

The coating is carried out with a Hicoater HC-LABO.

The application quantity is adjusted to 7.5 mg/cm$^2$.

Then the coated capsules are coated once more with an enteric coating based on Eudragit L 100 (process like the third coating in example 5).

Then a last coating with Kollicoat Smartseal 30D is carried out like the last coating from example 5.

The capsules are determined for the oral administration where the at last applied layer dissolves in the stomach, the second to last applied layer in the small intestine after the pH value has risen above 6, the next layer if either pH 5 is undershot, or pH 7 is exceeded, and the first applied layer finally in the cecum, as soon as the pH value drops below 6, or immediately after the preceding layer had been dissolved with the drop below pH 5.

Example 6

Hard gelatin capsules with probiotic filling are coated with Chitosan, which is dissolvable below pH 6.5 (process like the first layer in example 5).

Then a coating with Chitosan which is grafted with chlorogenic acid to an extent of 50%, and is indissolubly in the pH range from 5.5 to 6.5 is carried out.

The coating corresponds to the first coating although the Chitosan, deacetylated to 90%, is grafted with chlorogenic acid to an extent of 50% before the preparation of the coating solution.

The application quantity is adjusted to 7.5 mg/cm$^2$.

Then the coated capsules are coated once more with an enteric coating based on Eudragit L 100 (process like the third coating in example 5).

Then a last coating with Kollicoat Smartseal 30D is carried out like the last coating from example 5.

The capsules are determined for the oral administration where the at last applied layer is dissolved in the stomach, the second to last applied layer in the small intestine after the pH value has risen above 6, the next layer if either 5.5 is undershot or 6.5 is exceeded, and the first applied layer finally in the cecum, as soon as the pH value drops under 6.5, or immediately after the preceding layer had been dissolved with the drop under pH 5.5.

Example 7

Tungsten-coated pellets are coated with a citric acid-containing HPMC layer. The water-based spray solution is composed of 2.8% Pharmacoat 606 and 1.2% talc where citric acid is added, until a pH value of 5.0 is achieved The coating thickness is 4.2 mg/cm$^2$.

Then a coating with Chitosan is carried out (process like the first layer with example 5).

Then a coating with Chitosan which is deacetylated to 80% and is grafted with chlorogenic acid to an extent of 30%, and is indissoluble in the pH range from 6 to 7 is carried out. Apart from that, the preparation of the Chitosan solution is carried out according to the first coating.

The layer thickness amounts to 6 mg/cm$^2$.

Then a coating with Chitosan, which is grafted with chlorogenic acid to an extent of 50%, and is indissoluble in the pH range from 5.5 to 6.5 like the corresponding coating in example 6, is carried out.

Then the coated pellets are coated once more with an enteric coating based on Eudragit L 100 (process like the third coating in example 5).

The so coated pellets are filled into hard gelatin capsules.

The release of the tungsten completely takes place in the large intestine, even if the interindividual variability of the pH value in the small intestine of the target group amounts to 1.5 ph units (pH 6 to pH 7.5), the drop of the pH value after passage of the ileocecal valve, however, to only maximum 1 pH unit.

Fluctuations of the pH value within the small intestine by up to 0.4 pH units do not affect the reliability of the release.

Without the "further layers" (see examples 1a and 2a), with the requirement of the same variability tolerance and the same maximally necessary drop of pH in the large intestine, a reliable release would be possible only with individuals whose pH value before the reaching of the ileocecal valve lies between pH 6 and pH 6.5, or a stronger pH drop after the passage of the ileocecal valve would have to be achieved or the variability tolerance have to specified lower.

The tolerated interindividual variability of the pH value before the reaching of the ileocecal valve can be further increased by additional interlayers "further layers" with accordingly modified polymers and use of other final coatings (e.g., Eudragit L 30 D-55), without a stronger drop of the pH value with the passage of the ileocecal valve being necessary.

Example 8a

Prednisolone-containing micropellets are compressed to a matrix together with micropellets from Chitosan. Therefor the Chitosan micropellets are produced by spray drying of a 4% Chitosan solution (adjusted with acetic acid to a pH value of 5.2). The matrix particles are ground to granulate material with particle sizes between 0.25 and 0.35 mm. Within 90 minutes, the not completely in the matrix enclosed prednisolone is extracted in an aqueous solution with a pH value of 7.5. The granulate material particles then are compressed to tablets, with granulate material of the same particle size made of Chitosan which is grafted with chlorogenic acid to an extent of 30%, and is durable against aqueous solutions in the range between pH 5 and pH 7, which are coated afterwards with Eudragit L 100 (process like the third coating in example 5).

Finally a last coating with Kollicoat Smartseal 30D is carried out like the last coating from example 5, however, with 2% more plasticizer.

During release tests a release of 65% of the prednisolone arises after the simulated passage through the ileocecal valve.

Example 8b

Prednisolone-containing micropellets are processed like in example 8a. However, before the coating with the Eudragit L 100 the tablets are washed for 30 minutes in an aqueous solution with a pH value of 5.8 and are redried.

During release tests a release of more than 90% of the prednisolone arises after the simulated passage through the ileocecal valve. 30% of the prednisolone is released before reaching of the first flexure of the large intestine.

Example 9a

Tungsten-coated pellets are coated with Chitosan. Process like with the first layer with example 5.

Then the coated pellets are coated once more with a dispersion consisting of a mixture of dispersion particles from which 50% are dissolvable with a pH value of above 7 and 50% dissolvable with a pH value of less than 5.5.

The spray suspension is composed as follows:
Part 1:
1.2% triethyl citrate and 7.5% talc are dissolved in 58.3% water, then 33% Kollicoat Smartseal 30D are stirred in. The suspension is adjusted to a pH value of 6.2 by use of NH3, or citric acid.
Part 2:
1.2% triethyl citrate and 7.5% talc are dissolved in 58.3% water, then 33% of Eudragit FS 30D are stirred in. The suspension is adjusted to a pH factor of 6.2 by use of NH3, NaOH or citric acid.

Both solutions are mixed under slow stirring 30 minutes before beginning of the spray process and are stirred on slowly for these 30 minutes.

The coating thickness is adjusted to 4.5 mg/cm$^2$.

Then the coated capsules are coated once more with an enteric coating based on Eudragit L 100 (process like the third coating in example 5).

The so coated pellets are filled into hard gelatin capsules.

Example 9b

Tungsten-coated pellets are coated with Chitosan (process like with the first layer with example 5).

Then the pellets are coated with a citric acid-containing HPMC layer. The water-based spray solution is composed of 2.8% Pharmacoat 606 and 1.2% talc and citric acid is added, until a pH value of 5.0 is achieved.

The coating thickness is 4.2 mg/cm$^2$. The spray amount per time is adjusted so low that the Chitosan layer does not become significantly partially dissolved.

Then the coated pellets are coated once more with a dispersion consisting of a mixture of dispersion particles from which approx. 50% are dissolvable with a pH value of above 7 and approx. 50% dissolvable with a pH value of less than 5.5 analogously examples 9a.

Then the coated capsules are coated once more with an enteric coating based on Eudragit L 100 (process like the third coating in example 5).

The so coated pellets are filled into hard gelatin capsules.

The tungsten is not released before reaching of the ileocecal valve. The release takes place after the passage of the ileocecal valve. More than 50% are released before the first flexure.

Example 9c

Tungsten-coated pellets are coated with Chitosan (process like with the first layer with example 5).

Then the pellets are coated with a citric acid-containing HPMC layer. The water-based spray solution is composed of 2.8% Pharmacoat 606 and 1.2% talc, and citric acid is added, until a pH value of 5.0 is achieved.

The coating thickness is 4.2 mg/cm$^2$. The spray amount is adjusted so low that the Chitosan layer does not become significantly partially dissolved.

Then the coated pellets are coated once more in a dry-coating process.

For this purpose 40% Hydroxypropyl-Methylcellulose-Acetat-Succinat (HPMCAS; Shin-Etsu AQOAT®, model ACE HF; Shin-Etsu Chemical Co., Ltd., Niigata, Japan) and 40% Eudragit E P O are mixed with 20% talc and applied onto the pellets in a fluidized bed process (Flowcoater FLO-5) from below, while the pellets are sprayed with a plasticizer mixture out of another nozzle from above at the same time. The plasticizer consists of a mixture of 60% of triethyl citrate and 40% of acetylated monoglyceride (Myvacet®, type 9-45, Eastman, Tenn., USA). The supplied amount of the plasticizer mixture amounts to 50 weight percent of the whole polymer amount.

The coating thickness is adjusted to 8.5 mg/cm$^2$.

Afterwards the layer is also sprayed with water in a fluidized bed process. The quantity of the water amounts to 9% of the product weight. Then the pellets are thermically aftertreated with 60° for 20 minutes in an oven to finish the film formation. Then the coated capsules are coated once more with an enteric coating based on Eudragit L 100 (process like the third coating in example 5).

The so coated pellets are filled into hard gelatin capsules.

The capsules are determined for the oral administration where the hard gelatin capsule dissolves in the stomach, the enteric coating in the small intestine after the pH value has increased above 6, the further layer if the pH value decreases below 5 or increases above 6.5, and the first applied layer finally in the cecum, as soon as the pH factor drops again below 6.5.

A test in the different solutions, which simulate the conditions in the gastrointestinal tract, confirmed that the coated pellets are durable (to the effect that the active ingredient is not released) in artificial gastric juice (PH 3), artificial duodenal juice (PH 5), artificial jejunal juice (6.3) and artificial ileal juice (PH 7), both with tests with the single liquids, as well as with testing all liquids in the specified sequence.

If after a retention time of 20 minutes in jejunal- or ileal juice the coated capsule is transferred into a medium with a pH value lower by more than 1 units (e.g., in an artificial cecum or large intestine environment (PH 6)), the active-ingredient containing capsule contents are released within 25 minutes.

Example 9d

Tungsten-coated pellets are coated with Chitosan (process like with the first layer with example 5).

Then the pellets are coated with a citric acid-containing HPMC layer. The water-based spray solution is composed of 2.8% Pharmacoat 606 and 1.2% talc and citric acid is added, until a pH value of 5.0 is achieved.

The coating thickness is 4.2 mg/cm$^2$. The spray amount is adjusted so low that the Chitosan layer does not become significantly partially dissolved. Then the coated pellets are coated once more in a dry-coating process.

For this purpose 40% Hydroxypropyl-Methylcellulose-Acetat-Succinat (HPMCAS; Shin-Etsu AQOAT®, model ACE HF; Shin-Etsu Chemical Co., Ltd., Niigata, Japan) and 40% of Kollicoat Smartseal 30D (the latter processed to micronized powder by spray drying of the diluted polymer dispersion) are mixed with 20% talc and applied onto the pellets in a fluidized bed process (flowcoater FLO-5) from below, while the pellets are sprayed with a plasticizer mixture out of another nozzle from above at the same time. The plasticizer consists of a mixture of 60% triethyl citrate and 40% acetylated monoglyceride (Myvacet®, type 9-45, Eastman, Tenn., USA). The supplied amount of the plasticizer mixture amounts to 50 weight percent of the whole polymer amount.

The coating thickness is adjusted to 9 mg/cm$^2$.

Afterwards the layer is also sprayed with water in a fluidized bed process at a product temperature of 50° for 20 minutes. The quantity of the water amounts to 9% of the product weight.

Then the coated capsules are coated once more with an enteric coating based on Eudragit L 100 (process like the third coating in example 5).

The so coated pellets are filled into hard gelatin capsules.

Example 9e

Tungsten-coated pellets are coated with Chitosan (process like with the first layer with example 5).

Then the coated pellets are coated once more with a dispersion consisting of a mixture of dispersion particles of which 50% are dissolvable with a pH value of above 7 and 50% dissolvable with a pH value of less than 5.5.

The layer is realized by simultaneously spraying of two dispersions out of two separate spray nozzles.

The spray suspensions are composed as follows:
Suspension 1:
1.8% triethyl citrate and 7.5% talc are dissolved in 57.7% water, then 33% Kollicoat Smartseal 30D are stirred in.
Suspension 2:
1.2% triethyl citrate and 7.5% talc are dissolved in 58.3% water, then 33% Eudragit FS 30D are stirred in.

The coating thickness is adjusted to 4.5 mg/cm$^2$.

Then the coated pellets are coated once more with an enteric coating based on Eudragit L 100 (process like the third coating in example 5).

The so coated pellets are filled into hard gelatin capsules.

Example 9f

Tungsten-coated pellets are coated with Chitosan (process like with the first layer with example 5).

Then the coated pellets are coated once more with a dispersion consisting of a mixture of dispersion particles of which 50% are dissolvable with a pH value of above 7 and 50% dissolvable with a pH value of less than 5.5.

The layer is realized by simultaneously spraying of two dispersions from two separate spray nozzles.

The spray suspensions are composed as follows:
Suspension 1:
1.2% triethyl citrate, 3.5% polysorbate 80 and 7.5% talc are dissolved in 54.8% water, then 33% Kollicoat Smartseal 30D are stirred in.

Suspension 2:
1% triethyl citrate, 3.5% polysorbate 80 and 7.5% talc are dissolved in 55% water, then 33% Eudragit FS 30D are stirred in.

The coating thickness is adjusted to 5.2 mg/cm$^2$.

Then the coated pellets are coated once more with an enteric coating based on Eudragit L 100 (process like the third coating in example 5).

The so coated pellets are filled into hard gelatin capsules.

Example 10

Prednisolone-containing microtablets are coated with Chitosan (process like with the first layer with example 5).

Then the coated microtablets are arranged flat on a fine grating and are sprayed from spray nozzles arranged above the tablets with a spray suspension made of 43% Eudragit FS 30D, 6.45% talc, 0.65% triethyl citrate and water as remaining ingredient. A simultaneous dry air supply with a temperature of 55° is carried out through the grating from below. The spray amount per time unit is adjusted so that the dissolved polymer dries at the top side and at the lateral surfaces of the microtablets, before it can run down the lateral surfaces to the underside.

After complete coating of the top- and lateral surfaces the microtablets are turned over, and the coating process is repeated with the Kollicoat Smartseal 30D-solution from example 5 in an appropriate layer thickness (4.5 mg/cm$^2$). The spray amount per time unitis adjusted so that a running down of the suspension onto the underside of the microtablets is avoided.

Then the microtablets are coated with Eudragit L 100 (process like the third coating in example 5) and filled into hard gelatin capsules.

Example 11

Prednisolone-containing microtablets (body W, FIG. 6) are coated with a poly(MMA-DEAEMA) copolymer. The copolymer and the spray solution made from it, as well as the coating process correspond to the last layer from example 5 although in the preparation of the copolymer the percentage of DEAEMA is increased compared with the normal Kollicoat Smartseal 30D, so that the copolymer becomes already dissolvable with undershoot of a pH value of 6.0 (layer C, FIG. 6).

Then the coated microtablets are arranged flat on a fine grating and are sprayed from spray nozzles arranged above the tablets with the following spray solution: 25% Eudragit L 12.5, 25% Eudragit S 12.5, 3.1% talc, 0.6% triethyl citrate, 46.3% isopropanol (97%)

A simultaneous dry air supply with a temperature of 55° is carried out from below through the grating. The spray amount per time unit is adjusted so that the dissolved polymer dries at the top side and at the lateral surfaces of the microtablets, before it can run down the lateral surfaces to the underside (layer C1a, FIG. 6). The coating thickness is 5 mg/cm$^2$. This coating is dissolvable with a pH value of above 6.5.

After complete coating of the top- and lateral surfaces the microtablets are turned over, and the coating process is repeated with the Kollicoat Smartseal 30D-solution from example 5 in an appropriate layer thickness (4.5 mg/cm$^2$). The spray amount per time unit is adjusted so that a running down of the suspension onto the underside of the microtablets is avoided (layer C1b, FIG. 6). Then the microtablets are coated with Eudragit L 100 (process like the third coating in example 5, layer E, FIG. 6) and filled into hard gelatin capsules.

Example 12

Prednisolone-containing microtablets are coated and encapsulated like described in example 11. However, the microtablets are coated with a layer made of 85% HPMC (Pharmacoat 606), 5% talc and 10% croscarmellose after the first coating (before the arrangement on the grating).

This layer has a very strong swelling capacity? in contact with aqueous solutions.

Example 13

Prednisolone-containing micropellets are coated like with the first coating in example 11. However, the layer thickness is increased by 50%, and the percentage of tributylcitrate is doubled.

Then 20% coated prednisolone-containing micropellets are mixed with 40% Hydroxypropyl-Methylcellulose-Acetat-Succinat powder and 40% Kollicoat Smartseal 30D (the latter processed to powder by spray drying of the diluted polymer dispersion) and compressed into microtablets which are coated afterwards with Eudragit L 100 (process like the third coating in example 5). Finally the microtablets are filled into hard gelatin capsules.

Example 14

Capsules of the size 1 made of hydroxypropylmethylcellulose (HPMC) which are filled with mesalazine are coated with an 8-percent aqueous HPMC solution with the dip method. For this purpose the capsules are dipped by two thirds into the HPMC solution and are then dried in 40 degrees warm airflow, until they do not stick with touch any more. Then they are dipped into the HPMC solution by two thirds with the opposite side to ensure an overlapping layer formation. Afterwards a drying also takes place in the warm airflow, and then for 24 hours at room temperature.

Then the capsules are coated with the same method, however, only with a one-sided dip process two further times by two thirds with a HPMC solution which contains, in addition, 5% Eudragit RS and afterwards the same two thirds once more with Eudragit FS 30D for one time.

Then they are coated also by two thirds on the opposite side with Kollicoat Smartseal 30D, so that both coatings slightly overlap. Prior to this, 4.5% triethyl citrate (15% referred to the polymer weight) are added to the Kollicoat Smartseal 30D.

Afterwards the so coated capsules are dried at room temperature for 24 hours.

Then the capsules are coated with Kollicoat MAE 30DP, to which 5% triethyl citrate were added, with the same method like with the first coating.

Finally the coated capsules are filled into hard gelatin capsules of the size 00.

The active ingredient is released neither in the stomach, nor if after the stomach the pH value in the small intestine increases to pH 6.5. Only if the pH value decreases below pH 5.5 after the passage of the ileocecal valve, or the pH value increases to above 7 towards the end of the small intestine passage, the mesalazine is released. Due to the multiple untercoating of the Eudragit FS 30D layer with HPMC and Eudragit RS the dissolution after exceedance of pH 7 lasts so long that the active ingredient release takes place only after the passage of the ileocecal valve.

Example 15

Hard gelatin capsules with probiotic filling are coated with a poly(MMA-DEAEMA) copolymer. The copolymer and the spray solution made from it, as well as the coating process correspond to the last layer from example 5 although with the preparation of the copolymer the percentage of DEAEMA is increased compared with the normal Kollicoat Smartseal 30D, so that the copolymer becomes dissolvable already with undershoot of a pH value of 7.

500 g of such coated hard gelatin capsules are given into a CF-Granulator which is adjusted to 250 revolutions per minute and 150 l/min. of intake air with 30°. A suspension made of 300 g of a 4-percent Eudragit RS solution (12 g polymer in 288 g ethanol), 12 g Chitosan powder and 12 g Eudragit S powder (in each case by an average particle size of 95 µm), is dropped onto the capsule bed with a supply rate of 3.5 g/min.

After drying of the layer the coated capsules are coated once more with an enteric coating based on Eudragit L 100 and Eudragit S 100.

Composition of the Spray Solution:

25% Eudragit L 12.5, 25% Eudragit S 12.5, 3.1% talc, 0.6% triethyl citrate, 46.3% isopropanol (97%)

Process Equipment:

Glatt GPGC 1.1—top spray, nozzle: Schlick 970/0

Set-Up:

Nozzle opening: 1.2 mm, spray pressure: 2 bar, filter joggle time: 5 se, filter joggle interval: 30 s, supply air temperature: 33°, outlet temperature: 25°, spray rate: 15 g/min./kg, pressure difference bottom/product: 850 mbar, pressure difference filter: 450 mbar, drying air volume: 65 m$^3$/h, drying time at 40°: 2 h The coating thickness is 5 mg/cm$^2$. This coating is dissolvable with a pH value of above 6.5.

Then a last coating with Kollicoat Smartseal 30D is carried out like the last coating from example 5.

Such coated capsules release their contents if the pH value increases above 6.5 after the stomach passage, and afterwards once again drops below 6.5.

If the pH value increases above 7, the capsule contents are released even if the pH value afterwards only drops below a value of 7.

Example 15b

Capsules are produced like in example 15, however, the spray rate is halved with the first coating and HPMC capsules are used. The 4-percent Eudragit RS solution is replaced with a Eudragit 30 D dispersion which is diluted to 12% polymer content with water and adjusted to pH 6.75.

Example 16

Hard gelatin capsules with probiotic filling are coated with a poly(MMA-DEAEMA) copolymer. The copolymer and the spray solution made from it, as well as the coating process correspond to the last coating from example 5 although in the preparation of the copolymer the percentage of DEAEMA is increased compared with the normal Kollicoat Smartseal 30D, so that the copolymer becomes dissolvable already with undershoot of a pH value of 7.

500 g of such coated hard gelatin capsules are given into a CF-Granulator which is adjusted to 250 revolutions per minute and 150 l/min. of intake air with 30°. A solution made of 600 g of a 2-percent Chitosan solution (12 g of polymer and 10 g of acetic acid in 578 g of water) is dropped onto the capsule bed with a supply rate of 6 g/min. At the same time 12 g of Eudragit S powder with an average particle size of 95 µm, which was coated before with a 10 µm thick layer of Eudragit RS in a fluidized bed coater, are dispensed onto the capsule bed with a supply rate of 120 mg/minute.

After drying of the layer the coated capsules are coated with an enteric coating (analogously example 15) and then a last coating with Kollicoat Smartseal 30D is carried out like the last coating from example 5.

Such coated capsules release their contents if the pH value increases above 6.5 after the stomach passage, and afterwards once again drops below 6.5.

If the pH value increases above 7, the capsule contents are released even if the pH value afterwards only drops below a value of 7.

Example 17

Carboxymethylcellulose-microspheres with an average diameter of 50 µm are coated with Eudragit FS 30D. The layer thickness is adjusted to 25 µm.

Carboxymethylcellulose-microspheres with an average diameter of 50 µm are coated with Kollicoat Smartseal 30D. The layer thickness is adjusted to 25 µm.

Hard gelatin capsules with probiotic filling are coated with a poly(MMA-DEAEMA) copolymer. The copolymer and the spray solution made from it, as well as the coating process correspond to the last coating from example 5 although in the preparation of the copolymer the percentage of DEAEMA is increased compared with the normal Kollicoat Smartseal 30D, so that the copolymer already becomes dissolvable with undershoot of a pH value of 6.5.

500 g of such coated hard gelatin capsules are given into a CF-Granulator which is adjusted to 250 revolutions per minute and 150 l/min. of intake air with 30°. A suspension made of 300 g of a 4-percent Eudragit RS solution (12 g of polymer in 288 g of ethanol), 12 g micropellets coated with Kollicoat Smartseal and 12 g micropellets coated with Eudragit FS 30D, is dropped onto the capsule bed with a supply rate of 3.5 g/min.

After drying of the layer the coated capsules are coated with an enteric coating (analogously to the third coating from example 5) and then a last coating with Kollicoat Smartseal 30D is carried out like the last coating from example 5.

Such coated capsules release their contents if the pH value increases above 6 after the stomach passage, and afterwards once again drops below pH 5.5.

If the pH value increases above 7, the capsule contents are released even if the pH value afterwards only drops below a value of 6.5.

Example 18

Hard gelatin capsules with probiotic filling are coated with Chitosan, according to the first coating from example 5.

500 g of such coated hard gelatin capsules are given into a CF-Granulator which is adjusted to 250 revolutions per minute and 150 l/min. of intake air with 30°. A suspension made of 300 g of a 4-percent Eudragit RS solution (12 g of polymer in 288 g of ethanol), 12 g micropellets coated with Kollicoat Smartseal and 12 g micropellets coated with Eudragit FS 30D, is dropped onto the capsule bed with a supply rate of 3.5 g/min.

After drying of the layer the coated capsules are coated with an enteric coating (analogously to the third coating from example 5) and then a last coating with Kollicoat Smartseal 30D takes place like the last coating from example 5.

Such coated capsules release their contents if the pH value increases above 6 after the stomach passage, and afterwards once again drops below pH 5.5.

If the pH value increases above 7, the capsule contents are released even if the pH value afterwards only drops below a value of 6.5.

Example 19

Capsule bottoms (in the state-of-the-art partially also referred to as a capsule body) of the size 0 are produced with a reduced wall thickness of 60 µm and as described in US 2011/0033530 A1 coated with 40 µm thick functional layer (analogously to example 3 of the mentioned document). For this purpose they remain on the dip stick. However, Eudragit L 100 is used instead of Eudragit L 100-55 as a functional polymer (methacrylic acid-methylmethacrylate copolymer (1:2)), so that the layer does not become dissolvable above Ph 5.5 but only above Ph 6.0. The addition of triethyl citrate is increased from 10% to 13%. With the production of the functional coating, the capsule bottoms are, however, dipped only so far that, on fitting together with a capsule cap, the functional coating extends two millimeters under the capsule cap.

Capsule bottoms of the size 1 are produced and coated as described above. However, a methacrylic acid-methylmethacrylate copolymer (1:1.5) is used instead of Eudragit L 100 as the functional polymer analogous to Eudragit S 100 or Eudragit L 100, but with a monomer ratio lying between these both copolymers, so that the layer becomes dissolvable only above pH 6.5.

Capsule bottoms of the size 2 are produced and coated as described above. However, Eudragit S 100 is used instead of Eudragit L 100 as the functional polymer (methacrylic acid-methylmethacrylate copolymer (1:2)), so that the layer becomes dissolvable only above pH 7.0.

Capsule caps of the size 1 are produced with a reduced wall thickness of 60 µm and as described in US 2011/0033530 A1 coated with a 40 µm thick functional polymer layer (by analogy with example C6 of the mentioned document). However, Kollicoat Smartseal 30D is used instead of Eudragit FS 30D as a functional polymer. On account of the low viscosity of the dispersion the layer is produced with several immersions.

Capsule caps of the size 0 are produced and coated as described above. However, instead of Kollicoat Smartseal 30D as a functional polymer a polymer is used which is produced like Kollicoat Smartseal 30 D where, however, a decreased percentage in diethylaminoethylmethacrylate monomers is used, so that the polymer becomes dissolvable only below Ph 5.

Capsule caps of the size 2 are produced and coated as described above. However, instead of Kollicoat Smartseal 30D as a functional polymer a polymer is used which is produced like Kollicoat Smartseal 30D where, however, an increased percentage in diethylaminoethylmethacrylate monomers is used, so that the polymer already becomes dissolvable below Ph 6.

Capsule bottoms and capsule caps of the size 3 are produced and coated as described above. However, instead of Kollicoat Smartseal 30D as a functional polymer a polymer is used which is produced like Kollicoat Smartseal 30D where, however, an increased percentage in diethylaminoethylmethacrylate monomers is used, so that the polymer already becomes dissolvable below Ph 6.5.

Capsule bottoms and capsule caps of the size 00 are produced with a reduced wall thickness of 60 µm and as described in US 2011/0033530 A1 coated with a 40 µm thick layer made of Eudragit L 100-55 and Eudragit 30 D (example 1 of the mentioned document). The functional layer becomes dissolvable above pH 5.5.

The coated capsule bottoms of the size 3 are filled with an active ingredient, for example, 250 mg of mesalazine, and then closed with the coated capsule caps of the size 3. The gap between the capsule halves is sealed with the same polymer dispersion with which the capsule cap was coated. For this purpose it is dispensed into the gap and dried.

The capsules of the size 3 are transferred into coated capsule bottoms of the size 2 and those are closed with coated capsule caps of the size 2. The gap between the capsule halves is sealed with the same polymer dispersion with which the capsule cap was coated. For this purpose it is dispensed into the gap and dried.

The capsules of the size 2 are transferred into coated capsule bottoms of the size 1, and those are closed with coated capsule caps of the size 1. The gap between the capsule halves is sealed with the same polymer dispersion with which the capsule cap was coated. For this purpose it is dispensed into the gap and dried.

The capsules of the size 1 are transferred into coated capsule bottoms of the size 0, and those are closed with coated capsule caps of the size 0. The gap between the capsule halves is sealed with the same polymer dispersion with which the capsule cap was coated. For this purpose it is dispensed into the gap and dried.

The capsules of the size 0 are transferred in coated capsule bottoms of the size 00, and those are closed with coated capsule caps of the size 00. The gap between the capsule halves is sealed with the same polymer dispersion with which the capsule cap was coated. For this purpose it is dispensed into the gap and dried.

The capsules of the size 00 are transferred in capsule bottoms of the size 000, and those are closed with capsule caps of the size 000.

The capsules reliably release the active ingredient in the large intestine if the drop of the pH value amounts at least to one pH unit after the passage of the ileocecal valve, and the maximal pH value in the small intestine lies between 5.5 and 7.5.

The usually used capsule sizes and their measures are known to the person skilled in the art from the appropriate literature. For example, these are described in "Die Kapsel, Grundlagen, Technologie and Biopharmazie einer modernen Arzneiform", Fahrig W. and Hofer U. (1983), Wissenschaftliche Verlagsgesellschaft mbH Stuttgart.

If for the coating polymers or copolymers are used whose threshold values lie with lower and/or higher pH values, the operating range of the formulation (the range in pH values within which the release takes place with a drop of the pH value by a certain amount) can be expanded down to as low as pH 2 and upwards to up to pH 9. Preferably an operating range is aimed of from pH 3 to 9, is more preferably from pH 4 to pH 8, particularly preferably from pH 5.5 and Ph 7.5.

Such changes of the operating range can be also made with the other execution example, embodiments and variants.

Example 21

Oblong tablets of the size 4×4×14 mm are coated with the dip method with a 2-percent Chitosan solution (2% of Chitosan dissolved in one and a half-percent acetic acid). For this purpose the capsules are dipped by two thirds into the Chitosan solution and then are dried in 55 degrees warm airflow, until they do not stick with touch any more. This process is repeated three times. Then they are dipped at the opposite end by two thirds into the Chitosan solution to ensure an overlapping layer formation. Afterwards a drying is also carried out in the warm airflow. This process is also repeated three times. Then a drying is carried out with room temperature for 24 hours.

Then the oblong tablets are dipped for 140 seconds by two thirds into a 0.1-molar phosphate buffer with pH 7.8 and afterwards in deionised water for removing the residuals of the buffer solution. Both liquids are in light stream due to a magnetic stirrer. Afterwards a drying is carried out in the warm airflow.

Then the same after-treatment is carried out at the other end of the oblong tablet, also by two thirds, so that the after-treated areas overlap.

After a subsequent drying over 24 hours the oblong tablets are dipped by two thirds into Eudragit FS 30D (mixed with 10% triethyl citrate referred to the polymer amount) and then dried in a 50 degrees warm airflow, until they do not stick with touch any more.

Then they are dipped at the opposite end also by two thirds into Kollicoat Smartseal 30D, so that both coatings slightly overlap. To the Kollicoat Smartseal 30D 4.5% triethyl citrate (15% referred to the polymer weight) are added beforehand. Then they are dried in a 50 degrees warm airflow, until they do not stick with touch any more.

Afterwards the so coated oblong tablets are dried for 24 hours at room temperature.

Then the oblong tablets are coated with the same method from both ends in each case by two thirds with Kollicoat MAE the 30DP to which 5% triethyl citrate were added.

Finally the coated oblong tablets are filled into hard gelatin capsules of the size 00.

The active ingredient is released neither in the stomach, nor if after the stomach the pH value in the small intestine rises to pH 6.5. Only if the pH value sinks below pH 5.5 after the passage through the ileocecal valve, or the pH value rises above 7 towards the end of the small intestine passage, and afterwards after the passage through the ileocecal valve sinks below pH 6.5, the active ingredient of the oblong tablet is released.

Example 22

Capsule caps of the size 1 made of gelatin or preferably HPMC are produced with a reduced wall thickness of 50 µm and coated with a 25 µm thick functional polymer layer as described in US 2011/0033530 A1 (by analogy with example C6 of the mentioned document). However, Kollicoat Smartseal 30D is used instead of Eudragit FS 30D as functional polymer. On account of the low viscosity of the dispersion the layer is produced in several clippings. This layer becomes dissolvable below pH 5.5.

Then the capsule caps are coated with a second 25 µm thick functional layer (by analogy example 3 of the mentioned document). However, Eudragit L 100 (methacrylic acid-methylmethacrylate copolymer (1:2)) is used instead of Eudragit L 100-55 as functional polymer, so that the layer does not become dissolvable above pH 5.5 but only above pH 6.0. The addition of triethyl citrate is increased from 10% to 13%. Only after the coating processes have taken place the capsule caps are stripped off of the dip-sticks.

Capsule bottoms (in the state-of-the-art partially also referred to as a capsule body) of the size 1 are produced and coated like described before with the capsule caps. However, instead of Kollicoat Smartseal 30D as functional polymer a polymer is used which is produced like Kollicoat Smartseal 30D where, however, an increased percentage of diethylaminoethylmethacrylate monomers is used, so that the first coating becomes dissolvable already below pH 6.5.

Instead of Eudragit L 100, Eudragit S 100 (methacrylic acid-methylmethacrylate copolymer (1:2)) is used as functional polymer, so that the second layer becomes dissolvable only above pH 7.0.

The coated capsule bottoms are filled with an active ingredient, for example, 400 mg of mesalazine, and closed with the coated capsule caps. The gap between capsule halves is sealed with a not water-soluble polymer dispersion. For this purpose this is dispensed into the gap and dried. For example, Eudragit RS, Eudragit NE or ethylcellulose can be used.

The capsules of the size 1 are inserted in capsule bottoms of the size 0, and closed with capsule caps of the size 0.

The capsules reliably release the active ingredient in the large intestine if the drop of the pH value amounts to at least 1.5 pH units after the passage of the ileocecal valve, and the maximal pH value in the small intestine lies between 6 and 8.

Example 23

Carboxymethylcellulose-microspheres are split in three groups.

Group 1 is coated with a poly(MMA-DEAEMA) copolymer (poly(methylmethacrylate-diethylaminoethylmethacrylate)) which becomes dissolvable below pH 5.5. Then a layer made of a Poly(MMA-AA) copolymer or a poly (methacrylic acid-methylmethacrylate)-copolymer is applied which becomes dissolvable above pH 5.8.

Group 2 is coated with a poly(MMA-DEAEMA) copolymer which becomes dissolvable below pH 6.0. Then a layer made of a Poly(MMA-AA) copolymer or a poly (methacrylic acid-methylmethacrylate)-copolymer is applied which becomes dissolvable above pH 6.3.

Group 3 is coated with a poly(MMA-DEAEMA) copolymer which becomes dissolvable below pH 6.5. Then a layer made of a Poly(MMA-AA) copolymer or a poly (methacrylic acid-methylmethacrylate)-copolymer is applied which becomes dissolvable above pH 6.8.

With the coatings also plasticizers, anti-adhesives and if necessary further excipients are used in addition to the copolymers.

500 g of hard gelatin capsules of the size 2 with active ingredient filling are given into a CF-Granulator which is adjusted on 250 revolutions per minute and 150 l/min. of intake air with 30°. 300 g of a 4-percent Eudragit RS solution is dropped onto the capsule bed with a supply rate of 3.5 g/min. At the same time a mixture composed of the three groups of coated microspheres (in each case 8 g, so a total of 24 g of microspheres) is dispensed onto the capsule bed with a supply rate of 280 mg/minute. After drying of the layer the coated capsules are transferred into hard gelatin capsules of the size 0.

The capsules reliably release the active ingredient in the large intestine if the drop of the pH value after the passage of the ileocecal valve amounts at least 0.8 pH units, and the maximal pH value in the small intestine lies between 5.8 and 7.3.

Example 24

Active-ingredient containing plane-parallel tablets, diameters 13 mm, height 3 mm, facet 0.5 mm, are stacked to rolls and are held between two holding discs at the end faces of the rolls. Then the rolls are coated with an organic poly methylmethacrylate solution (acetone as a solvent) in a spray process. Spray amount, dry air amount and dry air temperature are adjusted so that at the tablet edges a steady polymer film is formed, the tablet surfaces, nevertheless, neither are coated, nor stick together so intense that they might not be separated any more without damage.

After the separation from the roll piles the tablets such water-indissolubly coated at their edge surfaces are arranged flat on a fine grating. The top of the tablets is covered with a shadow mask made from stainless steel sheet which has square recesses of 3 mm by 3 mm in a right-angled repetition grid of 5 mm by 5 mm along its X and Y axis. Between the recesses bars of 2-mm width are located.

Coating processes are carried out through these recesses by means of spray nozzles arranged above the shadow mask. Also from above the shadow mask the supply of 55° C. warm dry air is carried out, which is sucked off primarily in the tablet interspaces through the fine grating.

First a coating with a poly(MMA-DEAEMA)-copolymer which is dissolvable below pH 6.8 is carried out.

After the shadow mask was moved by 2.5 mm along its X axis, a coating with a poly (MMA-DEAEMA)-copolymer which is dissolvable below pH 6.3 is carried out.

After the shadow mask was moved by 2.5 mm along its Y axis, a coating with a poly (MMA-DEAEMA)-copolymer which is dissolvable below pH 5.8 is carried out.

After the shadow mask was moved again by 2.5 mm along its X axis (preferably against the previous dislocation direction along the X axis), a coating with a poly(MMA-DEAEMA)-copolymer which is dissolvable below pH 5.3 is carried out.

Afterwards shadow mask is moved again by 2.5 mm along its Y axis preferably against the previous dislocation direction along the Y axis).

Then a coating with a poly(methacrylic acid-methylmethacrylate)-copolymer which is dissolvable above pH 7 is carried out.

After the shadow mask was moved by 2.5 mm along their X axis, a coating with a poly (methacrylic acid-methylmethacrylate)-copolymer which is dissolvable above pH 6.5 is carried out.

After the shadow mask was moved by 2.5 mm along their Y axis, a coating with a poly (methacrylic acid-methylmethacrylate)-copolymer which is dissolvable above pH 6 is carried out.

After the shadow mask was removed, a coating with a poly (methacrylic acid-methylmethacrylate)-copolymer which is dissolvable above pH 5.5 is carried out.

Afterwards the tablets are coated with a poly(MMA-DEAEMA)-copolymer which is dissolvable below pH 5.5.

Then the tablets are turned over and coated on the opposite side in the same manner, like on the first side.

The coating thicknesses are adjusted in each case to 4.5 g per cm². By means of addition of plasticizers it is ensured that with the used dry air temperature a reliable film formation is achieved.

By the shadow mask openings of 3 mm in the grid of 5 mm it is ensured that the individual layer sequences slightly overlap geometrically, so that no uncoated gaps result.

The tablets release the active ingredient if the pH value after the stomach passage rises above pH 5.5, and afterwards once again drops. Up to a pH value maximally being present in the small intestine of 7.5 a drop by more than 0.7 pH units is sufficient to trigger the release.

If for the coating of the second tablet side polymers or copolymers are used whose threshold values of the pH value, above or below which they become dissolvable or permeable, are offset upwards by 0.25 pH units, already a drop of the pH value by 0.5 units is sufficient to trigger a release, provided that the pH value at most being present in the small intestine lies between 5.5 and 7.5.

If for the coating polymers or copolymers are used whose threshold values lie with lower and/or higher pH values, the operating range of the formulation (the range of pH values within which the release takes place with a drop of the pH value by a certain amount) can be expanded downwards to as low as pH 2 and upwards to up to pH 9. Preferably an operating range of from pH 3 to 9 is aimed, more preferably from pH 4 to pH 8, particularly preferably from pH 5.5 and pH 7.5.

If positive overshoots of the pH value after the stomach passage are to be expected in the target group for the application of the tablets, between the removal of the shadow mask and the coating with the poly (methacrylic acid—the methylmethacrylate) copolymer which is dissolvable above pH 5.5 an additional coating can be carried out which is dissolved time-delayed, so that possible positive overshoots of the pH value have declined till the entire dissolution of this layer at least to a large extent. This additional coating can consist, for example, of slowly dissolving polymers, or of a layer sequence, e.g., from an disintegrating layer and an overlying slightly permeable layer, as already described above for the achievement of a time delay.

To be able to adjust the fine gradations of the solubility threshold values, special polymers or copolymers with distinct monomer ratios do not necessarily have to be synthesized in each case for every coating. In certain ranges a setting of the solubility threshold values is also possible by mixture of copolymers with different monomer percentages, as for example by mixture of organic spray solutions of Eudragit L and Eudragit S in different percentages by weight.

Example 25

Paracetamol (acetaminophens) E-CDS pellets are produced like described in "Multiparticulate Chitosan-Dispersed System for Drug Delivery", Norihito SHIMONO et al., Chem. Pharm. Bull. 51(6) 620-624 (2003). However after the step of "Preparation of Drug Cores" the active ingredient-loaded cores are at first coated with a layer which is dissolvable below pH 6 but is insoluble above that.

For this purpose a poly(MMA-DEAEMA) copolymer dispersion is produced according to Kollicoat Smartseal 30D (see WO 2009/016258 A1, example 1) with which the DEAEMA percentage is increased so far that the threshold value for the solubility is raised from pH 5.5 to pH 6.0.

A spray suspension is prepared consisting of 33% of the described dispersion, 1.5% triethyl citrate, 8% talc, and 57.5% water. The coating is carried out in an Aeromatic Streal by means of top spray.

The intake air temperature amounts to 55°, the product amount 0.5 kg, the spray rate 6 g/min, the nozzle diameters 0.8 mm, the spray pressure 1.5 bar. The coating is carried out up to a weight increase of 30%. Then a drying is carried out for approx. 10 to 15 min at 55° C.

Then the coating is carried out as described in "Preparation of CDS Pellets" although no Chitosan powder is used, but a powder of comparable particle size which is produced as follows:

Chitosan acetate (average molecular weight of the Chitosan approx. 22000 Dalton) is dissolved in the 150-fold amount (weight/weight) of deionized water. Succinic anhydride is added with 7 minutes of vigorous stirring in an amount of 32% of the polymer dry weight. After 70 minutes of reaction time at room temperature the pH value of the solution is adjusted to 8.6 using 0.2 N sodium hydrogen carbonate, and the solution is stirred moderately for 10 hours at room temperature. Then the solution is dialyzed by means of a dialysis membrane with a cut-off of 3500 Dalton against water which is adjusted to pH 10.3 with sodium hydroxide. Then a further dialysis is carried out against deionized water enriched with carbonic acid under a CO2 atmosphere with a pressure of 3.5 to 4 bar. According to desired height of the solubility pH threshold values, or of the corresponding dissolution speed above or below the indissoluble area a dialysis can also be carried out against an acetic acid-, sodium lye-, or ammonia solution (if applicable also against a mixture of carbonic- and acetic acid solution or a mixture of sodium hydroxide solution and ammonia solution) where the concentration of the ions remaining after the drying can serve for the setting of the dissolution speeds.

The dried reaction product is dissolvable in aqueous solutions with pH values below pH 5.2 and above pH 6.3, in between it is not dissolvable. The range, in which the reaction product is insoluble, can be lowered towards lower pH values by increase of the amount of the succinic anhydride, and increased by reduction of the amount. The width of the indissoluble range can be influenced by the choice of the molecule weight of the Chitosan used.

The reaction product is processed by spray drying, drying and grinding or other suitable processes into powder of the suitable particle size (on average approx. 85 μm).

After this coating the enteric coating is carried out as described in "Preparation of E-CDS Pellets".

In gastric juice at pH 1.2 a release of less than 2 percent of the paracetamol occurs within 2 hours. In the subsequently following intestinal juice at pH 6 a release of less than 4 percent of the paracetamol (including the amount released in the gastric juice) occurs within further 2 hours. In the subsequently following intestinal juice at pH 6.7 a release of less than 5 percent of the paracetamol (including the amount released in the gastric juice and intestinal juice at pH 6) occurs within further 2 hours. In the subsequently following cecal juice at pH 5.6 a release of more than 50% of the paracetamol occurs within one hour.

If a cecal juice at pH 4.8 follows the intestinal juice at pH 6.0 directly, a release of more than 50% of the paracetamol also occurs within one hour.

Example 26

Hard gelatin capsules of the size 3 are filled with 195 mg of mesalazine and 25 mg of Explotab each and are closed. Then a coating with hydroxypropylcellulose is carried out. For this 66 g of Klucel EF are dissolved in 660 g deionized water and are sprayed onto 1.5 kg of filled capsules in an O'Hara Labcoat 1 from a 1.2 mm nozzle with 1.1 bar. The intake air is adjusted to 150 m³ per hour and 35° C., the spray rate amounts to 4 g/min. According to the humidity concentration of the intake air the spray rate can be increased, or must be further reduced to avoid softening the capsules. The capsules are dried at room temperature for 12 hours.

Then a coating is carried out with a poly(MMA-DEAEMA) copolymer dispersion which is produced according to Kollicoat Smartseal 30D (see WO 2009/016258 A1, example 1). However, the percentage of DEAEMA is adjusted so that the threshold value for the solubility is raised from pH 5.5 to pH 6.0.

820 g of such produced dispersion with 30% polymer content are mixed with 25 g triethyl citrate, 120 g talc and 1000 g water into a spray solution. The coating is carried out with the same process like the coating with hydroxypropylcellulose. However, a spray rate of 15 g/min can be used on account of the precoating (reduced to 9 g/min during the first 10 minutes).

200 g of a dried Chitosan succinic anhydride reaction product as described in example 25 is homogenized in carbonated water and dissolved overnight under CO2 atmosphere (gas pressure 3.5 bars) and vigorous stirring. Then the solution is adjusted to a viscosity of 100 mPa*s with deionized water at 2 bar CO2, and is sprayed on like with both preceding coating processes, while a 0.8 mm nozzle is used. The spray rate amounts to 4 g/min at the beginning, after spraying on of 10% of the solution being done 10 g/min.

Instead of using CO2 the solution alternatively can also be produced with an aqueous ammonia solution, where the pH is adjusted to approx. 7.5. The production of the spray solution with use of sodium lye (also approx. pH 7.5) or acetic acid (approx. pH 4.4) is also possible, where, however, the solubility threshold values can shift to lower or higher pH values which must be compensated if necessary by a change of the amount of succinic anhydride with the production of the polymer.

The capsules are dried afterwards for 24 hours at 30° C.

Then a further coating with hydroxypropylcellulose is carried out, by analogy to the first applied layer.

Then an enteric coating is carried out. For this 820 g Eudragit L 30 D-55 are mixed with 123 g talc, 24 g triethyl citrate and 1000 g water into a spray solution. The spray process is carried out like with the coating with the poly (MMA-DEAEMA) copolymer dispersion. Afterwards a drying is carried out at room temperature for 24 hours.

In the gastric juice (pH 1.2 for 2 hours) and in the small intestine juice (pH 6 for 2 hours and pH 6.7 for further 2 hours) no release of mesalazine takes place. In the cecal juice (pH 5.6 after the small intestine juice with pH 6.7, respectively pH 4.8 after the small intestine juice with pH 6.0) the capsule shell ruptures after 30 minutes and the mesalazine is released.

Example 27

Paracetamol (acetaminophen) CDS pellets are produced as described in "Multiparticulate Chitosan-Dispersed System for Drug Delivery", Norihito SHIMONO et al., Chem. Pharm. Bull. 51(6) 620-624 (2003).

Then a further coating is carried out as described under "Preparation of CDS Pellets", although no Chitosan powder is used, but a powder of comparable particle size which is produced as follows:

Chitosan acetate (average molecular weight of the Chitosan approx. 15000 Dalton) is dissolved in the 150-fold amount (weight/weight) of deionized water. Succinic anhydride is added with 7 minutes of vigorous stirring in an amount from 31% of the polymer dry weight. After 70 minutes of reaction time at room temperature the pH value of the solution is adjusted to 8.6 using 0.2 N sodium hydrogen carbonate, and the solution is stirred moderately for 10 hours at room temperature. Then the solution is dialyzed by means of a dialysis membrane with a cut-off of the 3500 Dalton against water which is adjusted to pH 10.3 with sodium hydroxide. Then a further dialysis is carried out against water which is adjusted to pH 8.2 with ammonia.

The dried reaction product is dissolvable in aqueous solutions with pH values below pH 5.8 and above pH 7.1, in between it is not dissolvable. The range, in which the reaction product is insoluble, can be lowered towards lower pH values by increase of the amount of the succinic anhydride, and increased by reduction of the amount. The width of the indissoluble range can be influenced by the choice of the molecule weight of the Chitosan used.

The reaction product is processed to powder of the suitable particle size (on average approx. 85 μm) by spray drying, drying and grinding or other suitable processes.

After this coating the enteric coating is carried out as described under "Preparation of E-CDS Pellets". However, the Eudragit L 100-55 is replaced with Eudragit L 100 and, in addition, triethyl citrate (10 weight percent referred to the Eudragit L 100) is added.

In gastric juice at pH 1.2 a release of less than 2 percent of the paracetamol occurs within 2 hours. In the subsequently following intestinal juice at pH 6.8 a release of less than 4 percent of the paracetamol (including the amount released in the gastric juice) occurs within further 2 hours. In the subsequently following intestinal juice at pH 7.4 a release of less than 5 percent of the paracetamol (including the amount released in the gastric juice and intestinal juice at pH 6.8) occurs within further 2 hours. In the subsequently following cecal juice at pH 6.0 a release of approx. 30% of the paracetamol occurs within one hour.

If a cecal juice at pH 5.4 follows the intestinal juice at pH 6.8 directly, a release of approx. 30% of the paracetamol also occurs within one hour.

During the next 5 hours the release occurs with approx. 10% of the paracetamol per hour. Then the release rate slightly drops.

Example 28

Active-ingredient containing quick-disintegrating pellets are produced as described in EP 0925060 example 1.

The pellets are coated, as described in "Multiparticulate Chitosan-Dispersed System for Drug Delivery", Norihito SHIMONO et al., Chem. Pharm. Bull. 51(6) 620-624 (2003), under "Preparation of CDS Pellets".

Then the same coating processes are carried out as described in example 27 of the present invention after the production of the CDS pellets.

The beginning of the release occurs comparably to the dependence on the course of the pH values described in example 27.

However, the release occurs to more than 70% within 30 minutes after the transfer into cecal juice.

Example 29

Active-ingredient containing pellets are produced and coated as described in example 28.

However, an additional coating with low substituted hydroxypropylcellulose (20% weight increase) is carried out between the both coating processes with the different Chitosan powders (unmodified and modified) as described in EP0210540 example 2.

The release occurs comparably with the characteristics described in example 28, however, after the transfer from intestinal juice at pH 7.4 into cecal juice at pH 6.0 already after 20 minutes a release of more than 70% occurs.

Example 30

Paracetamol pellets are produced like in example 25.

However, the modified Chitosan is not used as a powder for the second coating directly, but sucrose microspheres which are coated with the modified Chitosan.

The coated microspheres are produced as follows:

Sucrose microspheres, for example, produced in a Liquiflash process, as described in U.S. Pat. No. 5,874,110 example I, are dispersed in hexafluoroisopropanol in which Chitosan which is modified like in example 25 is dissolved (85 weight percent of modified Chitosan referred to the mass of the microspheres). On transfer into the liquid paraffin which contains 4% of Span 80 (stirred with 150 rpm) the hexafluoroisopropanol is evaporated (4 hours of stirring with 30° C.). Afterwards the coated microspheres are obtained by filtration and are washed several times with petroleum ether (40-60°). Then the microspheres are dried at room temperature for 24 hours.

Then the coated microspheres are used at place of the powder made of modified Chitosan.

The release characteristics correspond to a large extent to the one described in example 25. However, a release of more than 50% of the paracetamol is achieved within 20 minutes after transfer into cecal juice.

Example 31

Uncoated paracetamol (acetaminophen) pellets are coated with a layer, which is dissolvable below pH 7, but is insoluble above that. For this purpose a poly (N-acryloyl-N'-ethyl piperazine co methyl methcrylate) copolymer is produced, as described in "Solution Properties of Water-Soluble "Smart" Poly(N-acryloyl-N'-ethyl piperazine-co-methyl methacrylate)", G. Roshan Deen, Polymers 2012, 4, 32-45; doi:10.3390/polym4010032. The percentage of ArcNEP is 52 mol %.

The coating is carried out as described in "Multiparticulate Chitosan-Dispersed System for Drug Delivery", Norihito SHIMONO et al. under "Preparation of E-CDS Pellets".

However, the spray solution is produced from the poly (MMA-ArcNEP) copolymer, talc, triethyl citrate, acetone, ethanol (95%) (6:3:0,5:45,5:45).

Then a further coating is carried out, where, however, instead of the poly (MMA-ArcNEP) copolymer a PHEA-g-$C_{18}$10-1M50 polymer is used which is produced as described in "Tunable phase transition behaviors of pH-sensitive polyaspartamides having various cationic pendant groups", Han Woong Park, Colloid Polym Sci (2009)287: 919-926.

This coating is dissolvable in aqueous solutions below pH 6.5 and above pH 7.2.

After this coating the enteric coating is carried out as described under "Preparation of E-CDS Pellets". However, the Eudragit L 100-55 is replaced with a mixture of 80% Eudragit S 100 and 20% Eudragit L 100 and, in addition, triethyl citrate (10 weight percent referred to the Eudragit S/L mixture) is added.

This coating is dissolvable in aqueous solutions above pH 6.8.

Example 32

Uncoated paracetamol (acetaminophen) pellets are coated with a layer, which is dissolvable below pH 7.7, but is soluble above that.

For this purpose a poly(N-acryloyl-N'-ethyl piperazine co methyl methcrylate) copolymer is produced, as described in "Solution Properties of Water-Soluble "Smart" Poly(N-acryloyl-N'-ethyl piperazine-co-methyl methacrylate)", G. Roshan Deen, Polymers 2012, 4, 32-45; doi:10.3390/polym4010032. The percentage of the ArcNEP is 58 mol %.

The coating is carried out as described in "Multiparticulate Chitosan-Dispersed System for Drug Delivery", Norihito SHIMONO et al. under "Preparation of E-CDS Pellets".

However, the spray solution is produced from the poly (MMA-ArcNEP) copolymer, talc, triethyl citrate, acetone, ethanol (95%) (6:3:0,5:45,5:45).

Then a further coating is carried out, where, however, instead of the poly(MMA-ArcNEP) copolymer a PHEA-g-$C_{18}$10-IM90 polymer is used, which is produced as described in "Tunable phase transition behaviors of pH-sensitive polyaspartamides having various cationic pendant groups", Han Woong Park, Colloid Polym Sci (2009) 287: 919-926.

This coating is dissolvable in aqueous solutions below pH 6.2 and above pH 7.8.

Then a coating with a modified Chitosan is carried out like already described as the second coating in example 25. The layer is dissolvable below pH 5.2 and above pH 6.3.

Then a further coating, similar to the second coating described in this example with the PHEA-g-$C_{18}$10-IM90 polymer is carried out where, however, instead of PHEA-g-$C_{18}$10-IM90 polymer a PHEA-g-$C_{18}$10-PY45 polymer is used (produced as described in "Tunable phase transition behaviors of pH-sensitive polyaspartamides having various cationic pendant groups", but with changed concentration in aminomethylpyridine).

This coating is dissolvable in aqueous solutions below pH 4.3 and above pH 5.7.

After this coating the enteric coating is carried out as described under "Preparation of E-CDS Pellets". However, the Eudragit L 100-55 is replaced with a copolymer which is produced like Eudragit L 100-55 but, however, the monomer percentage is changed so (the percentage in methacrylic acid is increased) that the copolymer becomes dissolvable already above pH 4.7.

This coating is dissolvable in aqueous solutions above pH 4.7.

The pellets then are filled into hard gelatin capsules.

The operating range of this formulation extends over a range of the pH value maximally achieved in the small intestine from 4.8 to 8.9

Example 33

Capsule caps of the size 1 made of gelatin or preferably HPMC are produced with a reduced wall thickness of 40 μm and coated with three 20 μm thick functional polymer layers. For this purpose they remain on the dip-stick, until the last coating is finished. The first coating is carried out as descried in US 2011/0033530 A1 (by analogy with example C6 of the mentioned document). However, instead of Eudragit FS 30D a poly(MMA-DEAEMA) copolymer dispersion is prepared as functional polymer according to Kollicoat Smartseal 30D (see WO 2009/016258 A1, example 1) with which the DEAEMA percentage is increased so far that the threshold value for the solubility is raised from pH 5.5 to pH 5.8. On account of the low viscosity of the dispersion the layer is produced in several clippings if necessary. This layer becomes dissolvable below pH 5.8.

Then the capsule caps are coated with a second 20 µm thick functional layer. For the production of the dipping solution, Chitosan acetate (average molecular weight of the Chitosan approx. 22000 Dalton) is dissolved in the 150-fold amount (weight/weight) of deionized water, by analogy with example 25. Succinic anhydride is added with 7 minutes of vigorous stirring in an amount of 32% of the polymer dry weight. After 70 minutes of reaction time at room temperature the pH value of the solution is adjusted to 8.6 by using 0.2 N sodium hydrogen carbonate, and the solution is stirred moderately for 10 hours at room temperature. Then the solution is dialyzed by means of a dialysis membrane with a cut-off of 3500 Dalton against water which is adjusted to pH 10.3 with sodium hydroxide. Then a further dialysis is carried out against water which is adjusted to pH 8.2 with ammonia. The solution is adjusted to a viscosity of approx. 300 mPa*s. On account of the lower solid content compared to a dispersion, if necessary several dipping processes and dry processes are required to achieve the desired coating thickness.

Finally, the capsule caps are coated with a third 20 µm thick functional layer by analogy with example 3 of US 2011/0033530 A1.

The pH value of the dipping solution is adjusted to 5.0, and the quantity of water is adjusted accordingly to achieve the desired coating thickness after the drying. This layer becomes dissolvable above pH 5.5, after it was exposed to the gastric acid.

Capsule bottoms (in the state-of-the-art partially also referred to as a capsule body) of the size 1 are produced and coated like described before with the capsule caps. However, as functional polymer for the first coating a polymer is used which is produced like Kollicoat Smartseal 30 D where, however, a further increased percentage of diethylaminoethylmethacrylate monomers is used, so that the first coating becomes dissolvable already below pH 6.8.

Alternatively a poly(MMA-ArcNEP) copolymer with 52 mol % of ArcNEP, which is dissolvable below pH 7, can be used for the first coating. This is provided as a powder with an average particle size of approx. 150 nm, and is dispersed in the triple amount of water to which 1.5% sodium lauryl sulfate and 2% stearic acid are added. Then this dispersion is mixed with the same amount of Kollicoat Smartseal 30D, and 15% PEG 35000 and 15% triethyl citrate (both referred to the polymer content of the dispersion mixture) are added to obtain the dipping solution.

For the second coating instead of the modified Chitosan a PHEA-g-$C_{18}$10-IM50 polymer is used which is produced as descried in "Tunable phase transition behaviors of pH-sensitive polyaspartamides having various cationic pendant groups", Han Woong Park, Colloid Polym Sci (2009) 287: 919-926, and is dissolvable below pH 6.5, as well as above pH 7.2. It is dissolved in an aqueous ammonia solution with pH 8.6 and is adjusted to a viscosity of approx. 300 mPa*s.

For the third coating a mixture from 80% Eudragit S 100 and 20% Eudragit L 100 (both together dissolved in isopropanol, intensely mixed, and afterwards spray dried to receive a redispersible powder) is used for the redispersion as functional polymer instead of Eudragit L 100-55, so that the third layer becomes dissolvable only above pH 6.8. The addition of triethyl citrate is increased from 10% to 15%. The dispersion is adjusted to a pH value of 6.4 with sodium hydroxide solution.

The coated capsule bottoms are filled with an active ingredient, for example, 400 mg of mesalazine, and closed with the coated capsule caps. The gap between capsule halves is sealed with a not water-soluble polymer dispersion, for example, with Eudragit 30D. For this purpose it is dispensed into the gap and dried.

The capsules of the size 1 are put in capsule bottoms of the size 0, and these are closed with capsule caps of the size 0.

The capsules reliably release the active ingredient in the large intestine if the drop of the pH value after the passage of the ileocecal valve amounts to at least 1.1 pH units, and the maximal pH value in the small intestine lies between 5.5 and 7.9 (respectively 8.1 with the use of the poly(MMA-ArcNEP) copolymer).

Example 34

Gelatin hard capsules of the size 3 are filled with 195 mg mesalazine and 25 mg Explotab in each case and are closed.

Then a coating with hydroxypropylcellulose is carried out. For this 66 g of Klucel EF are dissolved in 660 g deionized water and are sprayed onto 1.5 kg of filled capsules in an O'Hara Labcoat 1 from a 1.2 mm nozzle with 1.1 bar. The intake air is adjusted to 150 $m^3$ per hour and 35° C., the spray rate amounts to 5 g/min. According to the humidity content of the intake air the spray rate can be increased, or must be further reduced to avoid softening of the capsules. The capsules are dried at room temperature for 12 hours.

Then there is carried out a coating with a poly(MMA-DEAEMA) copolymer dispersion which is produced according to Kollicoat Smartseal 30D (see WO 2009/016258 A1, example 1). However, the percentage of DEAEMA is adjusted so that the threshold value for the solubility is raised from pH 5.5 to pH 6.5.

820 g of such produced dispersion with 30% polymer content are mixed with 25 g triethyl citrate, 125 g talc and 1000 g water into a spray solution. The coating is carried out with the same process as the coating with hydroxypropyl-cellulose. However, a spray rate of 11 g/min can be used on account of the precoating (reduced to 6 g/min during the first 10 minutes).

420 g of such coated hard gelatin capsules are given into a CF-Granulator which is adjusted on 250 revolutions per minute and 150 l/min. of intake air with 30°. A suspension made of 300 g of a Eudragit 30 D dispersion diluted with water to a polymer concentration of 12% and adjusted to pH 6.75, 12 g poly(MMA-DEAEMA)-copolymer powder and 12 g poly (MA-MMA-MAA) copolymer powder (produced from Kollicoat Smartseal 30D, respectively Eudragit FS 30D, by melt extrusion with subsequent granulation, in each case with an average particle size of 95 µm), is dropped onto the capsule bed with a supply rate of 3.5 g/min.

After drying of the layer the coated capsules are coated with an enteric coating. The spray solution is composed as follows: 820 g Eudragit L 30 D-55, 120 g talc, 25 g triethyl citrate, 1000 g water.

The coating is carried out with the same process as the second coating.

After the drying the coated capsules are transferred into hard gelatin capsules of the size 1.

Such coated capsules release their contents if the pH value increases above 5.5 after the stomach passage, and afterwards once again falls below 5.5.

If an increase of the pH value above 7 occurs, the capsule contents are released even if the pH value afterwards falls only below a value of 6.5.

Example 35

Microspheres from Chitosan and 5-fluoruracil (30% 5-FU) are produced as described in "Preparation and characterization of chitosan microspheres containing doxifluridine.", Yoshino et al., Drug Development and Industrial Pharmacy, 2003, paragraph "Preparation of Microspheres". However, Chitosan is used which is deacetylated to 85%, and has an average molecule weight of 11000 Dalton. The average diameter amounts to 650 μm.

Chitosan which was modified as in example 25, however, with 31% of succinic anhydride, is dissolved in aqueous ammonia solution at pH 8.5 (1.5%). The solution is adjusted to a viscosity of 100 mPa*s. The microspheres are coated with the spray solution in a Glatt GPCG 1.1 by top spray. Nozzle: Schlick 970/0, nozzle bore: 1.2 mm, spray pressure: 1.8 bar, supply air temperature: 35°, spray rate: 12 g/min./kg, drying air volume: 55 m$^3$/H, drying time with 40°: 2H. The coating thickness is adjusted on 20 μm.

Then they are compressed into minitablets with a diameter of 2.5 mm and a height of 1.5 mm together with microspheres. For this purpose at first, granulate material, produced from Kollicoat Smartseal 30D as described in example 34, is filled into the compression mold, afterwards a microsphere is pushed slightly concentrically into the granulate material with a vacuum pipette, and then a granulate material is filled into it, which was produced with the same process while, however, instead of Kollicoat Smartseal a mixture of 46% Eudragit S 100, 45% Eudragit L 100 and 9% triethyl citrate was used, so that it is dissolvable above pH 6.4.

A PHEA-g-C$_{18}$10-PY45 polymer is produced as described in "Tunable phase transition behaviors of pH-sensitive polyaspartamides having various cationic pendant groups", but with appropriately changed percentage of aminomethylpyridine). By melt extrusion and granulation a granulate material with an average particle diameter of 90 μm is produced.

300 g of the tablets are given into a CF-Granulator which is adjusted to 300 revolutions per minute and 180 l/min. of intake air with 35°. A suspension made of 300 g of a Eudragit 30 D dispersion diluted with water to a polymer concentration of 12% and adjusted to pH 5 and 24 g of the granulate material is dropped onto the tablets with a supply rate of 4.5 g/min.

After the drying the minitablets are provided with an enteric coating. For this purpose 10 g polysorbate 80, 8.5 g glycerol monostearate and 17 g triethyl citrate are homogenized for at least 15 minutes in 160 g water which was warmed up to 75° C. beforehand. Then 230 g water is stirred in, and after cooling to room temperature the suspension is stirred in into 570 g of Eudragit L 30 D-55. The coating of 2.5 kg of tablets is carried out in an O'hara LabCoat, drum speed 20 U/min, nozzle diameter 1.2 mm, pressure 1, bar with 10 cm of nozzle distance, dry air volume 170 m$^3$/H with 45° C., spray rate 10 g/min, coating thickness 7.5 mg/cm$^2$.

The minitablets are filled into hard gelatin capsules of the size 00.

Example 36

HPMC capsules of the size 000 are filled with contrast spheres (air-filled hollow spheres made of PMMA (Plexiglas), diameter 4 mm, wall thickness 0.2 mm), which well reflect ultrasound with 3.5 MHz in aqueous media. The capsules weigh approx. 330 mg each.

This is followed by a coating with hydroxypropylcellulose. For this 66 g of Klucel EF are dissolved in 660 g deionized water and sprayed onto 1.25 kg of filled capsules in an O'Hara Labcoat 1 from a 1.2 mm of nozzle with 1.1 bar. The intake air is adjusted to 150 m$^3$ per hour and 35° C., the spray rate amounts to 5 g/min. According to the humidity content of the intake air the spray rate can be increased, or must be further reduced to avoid softening of the capsules. The capsules are dried at room temperature for 12 hours.

Then a coating is carried out with a poly(MMA-DEAEMA) copolymer dispersion which is produced according to Kollicoat Smartseal 30D (see WO 2009/016258 A1, example 1). However, the percentage of DEAEMA is adjusted so that the threshold value for the solubility is raised from pH 5.5 to pH 6.0.

820 g of such produced dispersion with 30% of polymer content are mixed with 25 g triethyl citrate, 125 g talc and 1000 g water into a spray solution. The coating is carried out with the same process as the coating with hydroxypropylcellulose. However, a spray rate of 11 g/min can be used on account of the precoating (reduced to 6 g/min during the first 10 minutes).

250 g of such coated hard gelatin capsules are given into a CF-Granulator which is adjusted on 180 revolutions per minute and 150 l/min. of intake air with 30°. A suspension made of 300 g of a Eudragit 30 D dispersion diluted with water to apolymer concentration of 12% and adjusted to pH 6.75 and 24 g of SALM-CS powder, produced as described in "Zwitterionic Chitosan Derivatives for pH-Sensitive Stealth Coating", Peisheng Xu et al., Biomacromolecules, Vol. 11, No. 9, 2010, with a An/Am ratio of 0.65 and an average particle size of 80 μm, is dropped onto the capsule bed with a supply rate of 3.5 g/min.

After drying of the layer 1.25 kg coated capsules are coated with an enteric coating. The spray solution is composed as follows: 820 g Eudragit L 30 D-55, 120 g talc, 25 g triethyl citrate, 1000 g water.

The coating is carried out with the same process as the second coating.

After the drying a coating with the poly(MMA-DEAEMA) copolymer is carried out once again as with the second applied layer.

The described capsules were given to a volunteer (male, 40 years) on six consecutive days. On day 1 and 2 in each case 30 minutes before the breakfast, day 3 and 4 in each case 15 minutes after the lunch and day 5 and 6 two hours after a light breakfast (yogurt with rice flakes). At intervals of 60 minutes each the abdomen of the volunteer was examined by means of ultrasound (Hitachi/Picker LC7000A with 3.5 MHz convex sensor) to localize the given capsule and to assess its condition. As reference objects one week before corresponding ultrasonic investigations with the volunteer were carried out with capsules which were coated with an indissoluble polymer (PMMA), and a further week before this with capsules which were coated only resistant to gastric juice (Eudragit L 30 D-55). In the ultrasound image the indissolubly coated capsule with the contrast spheres contained in it could be clearly distinguished from the contrast spheres escaped out of the capsule coated only resistant to gastric juice. In preceding investigations the localization of the air-filled contrast spheres was hindered partially by intestinal gases, which is why the volunteer received a diet poor in flatulence inducing ingredients in each case two days before the reference investigations and two days before, as well as during the test duration, by which the localization of the contrast spheres was clearly made easier.

With the investigation the capsules could be localized, nevertheless, not reliably with every sonography, as long as they were still in the upper and middle small intestine, but only with approx. 40% of the sonographies. Nevertheless, the terminal ileum, and the capsules if they were there, were always well recognizable. If the capsules were localized within the small intestine, they were always intact. 5 of the 6 given capsules could be localized in the area of the ileocecal valve intactly, two of them shortly before the passage, three of them shortly after. These last-mentioned 3 capsules could not be localized intactly with the next measurement any more. The distribution of the contrast spheres led to the conclusion that the capsule shell was still partly intact, but a part of the contrast spheres had already begun to spread in the large intestine contents. With this measurement the other 2 capsules could be localized intactly in the cecum. With the next measurement contrast spheres had also escaped from these capsules. The capsule of day 2 which could not be localized near the ileocecal valve could be localized with the subsequent measurement in the ascending large intestine where already escaped contrast spheres could also be localized. The capsule of day 5 could be already localized 3 hours after the taking before the ileocecal valve and was to be assessed there still as intact 5 hours after the taking. Then 6 hours after the taking (approx. 45 minutes after the lunch) the contrast spheres were localizable spread out in the cecum. No release could be ascertained in the small intestine. In the large intestine the contrast spheres were released before the hepatic flexure in all cases.

Example 37

Pellets or capsules are produced as described in U.S. Pat. No. 7,604,820 in the examples 1 or 2 or the combination of the examples 6 and 7 where instead of the Chitosan powder a powder of the same particle size distribution is used which consist, however, either of SALM-CS with a An/Am ratio of 0.65 like used in example 36, or a PHEA-g-$C_{18}$10-PY70 copolymer by corresponding particle size. The pellets and capsules show similar release characteristics as shown in U.S. Pat. No. 7,604,820 for the examples described there while the second test liquid (2Nd Fluid) is adjusted to 6.2 instead of pH 6.8. However, in addition, the active ingredient is also released even if instead of the third test medium with a pH value of 4.0 one with pH 7.4 is used. So the active ingredient is released when after an increase to above pH 6 a drop occurs to pH 4, as well as when the pH value rises up to 7.4.

Example 38

Paracetamol (acetaminophen) E-CDS pellets are produced as descried in example 25. However, at place of the layer which is dissolvable below pH 6 but is insoluble above that, a layer is applied which is produced like the subsequent layer, with the difference, that with the modification of the Chitosan only 30.8% of succinic anhydride is used, so that it is dissolvable below pH 6 and above pH 7.1.

So between the active-ingredient containing core and the enteric coating two further layers are comprised, of which the further inside situated one is insoluble between pH 6 and pH 7.1, and the other between pH 5.2 and pH 6.3.

The release in dependence of the pH value occurs as with example 25 where, however, the release speed is lower. In addition, with this embodiment a release is carried out even if the pellets are transferred into an artificial intestinal juice with pH 7.4. So the width of the operating range could be increased upwardly.

EXPLANATION OF THE DRAWINGS

In the figures from 1 to 6 the following identity letters are used:
W for the active ingredient core, for example, active-ingredient containing or active ingredient-coated pellets, capsules filled with active ingredient, active-ingredient containing tablets, microtablets etc.
P for protective coating (outer layer)
E for enteric coating (inner layer)
C for cecal coating (most inner layer)
C1 for cecal coating (most inner layer), or with embodiments without most inner layer the farthest inside lying further layer.
C2, C3, Cn for "further layers"
C1a for part layer 1 of a "further layer", e.g., dissolvable above to a certain upper pH value
C1b for part layer 2 of a "further layer", e.g., dissolvable below a certain lower pH value
S for disintegrating layers or layers which accelerate the dissolution of the overlying layers The FIGS. 7 to 15 show the ranges in which the pH dependent dissolvable or swellable layers used in the examples are durable. The numbering of the layers is carried out from the outside, so in the order of their contact with the surrounding aqueous solution if it is assumed that in the course of the intestinal passage all layers dissolve, respectively become permeable.

Not substantially ph dependent layers, like swelling layers, layers with disintegrating means and layers with pH value modulating characteristics are not listed in these diagrams and are skipped with the numbering of the layers.

Figure 1:
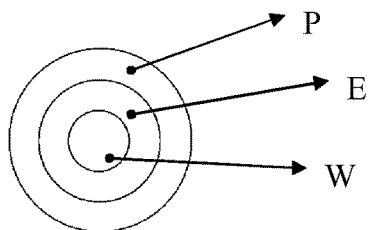

If an uncoated capsule was used in the respective example for the admission of coated pellets, microtablets, matrix-pellets etc., this is listed as a layer 1. The capsule is durable in none of the pH values occurring in the gastrointestinal tract, so that in the drawings no corresponding line is seen. However, it is durable in salivary liquid so long, until it has reached the stomach, so that the layer listed as the second layer does not come into contact with the neutral saliva but only with the acidic gastric juice. Based from the left to the right it is evident from the drawings which course the pH value of the surrounding solution must take, respectively can take, in order that the aqueous solution can successively dissolve the different layers, respectively can penetrate them.

BRIEF DESCRIPTION OF THE SEVERAL VIEWS OF THE DRAWINGS

FIG. 1 depicts a core (W) with enteric coating (inner layer, E) and protective coating (outer layer, P).

Figure 2:
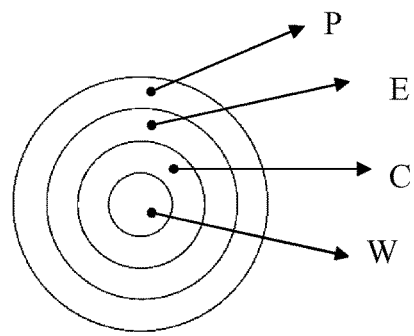

FIG. 2 depicts a core (W) coated with most inner layer (C), inner layer (E) and outer layer (P).

Figure 3:
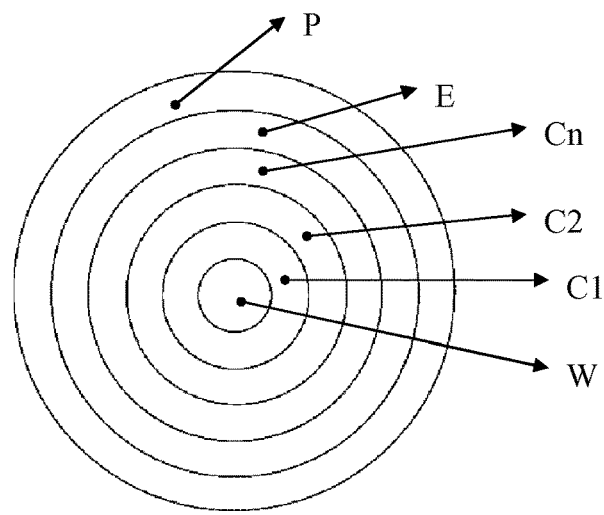
Figure 3:
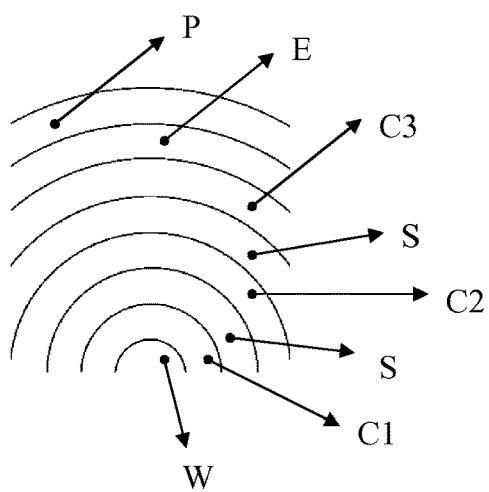
Figure 3:
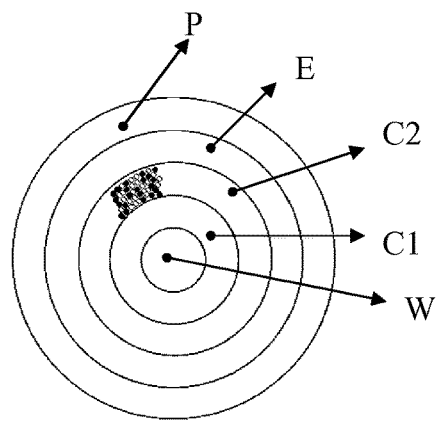

FIG. 3 depicts a core (W) coated with most inner layer or farthest inside lying further layer (C1), two or more further layers (C2 and Cn), inner layer (E) and outer layer (P).

FIG. 4 depicts a core (W) coated with most inner layer (C1), two further layers (C2 and C3), two disintegrating layers or layers which accelerate the dissolution of the overlying layers (S)), inner layer (E) and outer layer (P). Only relevant part shown.

FIG. 5 depicts a core (W) coated with most inner layer or farthest inside lying further layer (C1), further layer (C2, detailed construction layer C2 only shown partially), inner layer (E) and outer layer (P).

FIG. 6 depicts a microtablet (viewed laterally) with a core (W) coated with most inner layer (C), further layer having part layer 1 (C1a), e.g., dissolvable above to a certain upper pH value, and part layer 2 (C1b), e.g., dissolvable below a certain lower pH value, and inner layer (E).

FIG. 7 shows the ranges of durability of the layers of example 5.

FIG. 8 shows the ranges of durability of the layers of example 6.

FIG. 9 shows the ranges of durability of the layers of example 7.

FIG. 10 shows the ranges of durability of the layers of example 8a+b.

FIG. 11 shows the ranges of durability of the layers of example 9a+b.

FIG. 12 shows the ranges of durability of the layers of example 9c.

FIG. 13 shows the ranges of durability of the layers of example 9d.

FIG. 14 shows the ranges of durability of the layers of example 10.

FIG. 15 shows the ranges of durability of the layers of example 11.

It is claimed:

1. A formulation for the controlled release of one or more active ingredients in the large intestine of a mammal, characterized in that one or more active ingredients are enveloped with an Enteric layer and one or more individual further layers, wherein said one or more individual further layers are enveloped by said enteric layer, and wherein multiple further layers are enveloped by each other, and wherein each of said individual further layers is characterized by an individual defined lower pH threshold value and an individual defined upper pH threshold value and wherein each of said individual further layers is substantially or completely dissolvable or permeable in aqueous solutions with a pH value below that layer's own defined lower pH threshold value, and wherein each of said further layers is also substantially or completely dissolvable or permeable in aqueous solutions with a pH value above that layer's own defined upper pH threshold value, and wherein each of said further layers is neither substantially or completely dissolvable nor permeable in aqueous solutions with a pH value between that layer's own defined lower pH threshold value and that layer's own defined upper pH threshold value, and wherein said Enteric layer is characterized by a defined last pH threshold value, said defined last pH threshold value also being referred to as the defined upper pH threshold value of said Enteric layer, and wherein said Enteric layer is substantially or completely dissolvable or permeable in aqueous solutions only with a pH value above said defined last pH threshold value and wherein the defined last pH threshold value lies between 2 and 9, and the individual defined lower pH threshold value of each one of said one or more individual further layers is lower than the individual defined upper pH threshold value of that particular individual further layer itself, and that the defined upper pH threshold value of each single one of any of said layers that is enveloping one of said further layers lies between the individual defined lower and the individual defined upper pH threshold value of that further layer being enveloped by said single one layer.

2. A formulation according to claim 1, characterized in that the one or more active ingredients are enveloped with a Caecal layer, and the one or more active ingredients being enveloped with said Caecal layer, as well as said Caecal layer, are enveloped by the one or more further layers and the Enteric layer according to claim 1, wherein said Caecal layer is characterized by a defined lower pH threshold value, said defined lower pH threshold value of said Caecal layer also being referred to as the defined first pH threshold value, and wherein said Caecal layer is substantially or completely dissolvable or permeable in aqueous solutions only with a pH value below said defined lower pH threshold value of said Caecal layer and wherein the defined lower pH threshold value of the Caecal layer lies between 2 and 9, and that the defined upper pH threshold value of the further layer that is enveloping said Caecal layer lies above the defined lower pH threshold value of said Caecal layer.

3. A formulation according to claim 1, characterized in that at least one of said further layers comprises two different polymers, wherein at least one of said two different polymers is substantially or completely dissolvable or permeable in aqueous solutions with a pH value above a certain pH value and wherein at least another one of said two different polymers is substantially or completely dissolvable or permeable in aqueous solutions with a pH value below a certain pH value.

4. A formulation according to claim 2, characterized in that at least one of said further layers comprises two different polymers, wherein at least one of said two different polymers is substantially or completely dissolvable or permeable in aqueous solutions with a pH value above a certain pH value and wherein at least another one of said two different polymers is substantially or completely dissolvable or permeable in aqueous solutions with a pH value below a certain pH value.

5. A formulation according to claim 1, characterized in that at least one of said further layers comprises a polymer, wherein said polymer is substantially or completely dissolvable or permeable in aqueous solutions with a pH value below a certain range and wherein said polymer is also substantially or completely dissolvable or permeable in aqueous solutions with a pH value above a certain range but wherein said polymer is neither substantially or completely dissolvable nor permeable in aqueous solutions with a pH value within said certain range.

6. A formulation according to claim 2, characterized in that at least one of said further layers comprises a polymer, wherein said polymer is substantially or completely dissolvable or permeable in aqueous solutions with a pH value below a certain range and wherein said polymer is also substantially or completely dissolvable or permeable in aqueous solutions with a pH value above a certain range but wherein said polymer is neither substantially or completely dissolvable nor permeable in aqueous solutions with a pH value within said certain range.

7. A formulation according to claim 5, characterized in that at least one of said further layers comprises a Chitosan, wherein said chitosan comprises succinic acid groups.

8. A formulation according to claim 6, characterized in that at least one of said further layers comprises a Chitosan, wherein said chitosan comprises succinic acid groups.

9. A formulation according to claim 5, characterized in that at least one of said further layers comprises a Chitosan, wherein said chitosan comprises chlorogenic acid groups.

10. A formulation according to claim 6, characterized in that at least one of said further layers comprises a Chitosan, wherein said chitosan comprises chlorogenic acid groups.

11. A formulation for the controlled release of one or more active ingredients in the large intestine of a mammal, characterized in that one or more active ingredients are enveloped with a Caecal layer, an Enteric layer and one or more individual amphoteric layers, wherein said Caecal layer is enveloped by said one or more individual amphoteric layers and wherein said one or more individual amphoteric layers are enveloped by said enteric layer, and wherein multiple amphoteric layers are enveloped by each other, and wherein said Caecal layer is characterized by a defined lower pH threshold value, said defined lower pH threshold value of said Caecal layer also being referred to as the defined first pH threshold value, and wherein each of said individual amphoteric layers is characterized by an individual defined lower pH threshold value and an individual defined upper pH threshold value, and wherein said Enteric layer is characterized by a defined last pH threshold value, said defined last pH threshold value also being referred to as the defined upper pH threshold value of said Enteric layer, and wherein said Caecal layer is substantially or completely dissolvable or permeable in aqueous solutions only with a pH value below said defined first pH threshold value, and wherein each of said individual amphoteric layers is substantially or completely dissolvable or permeable in aqueous solutions with a pH value below that layer's own defined lower pH threshold value, and wherein each of said amphoteric layers is also substantially or completely dissolvable or permeable in aqueous solutions with a pH value above that layer's own defined upper pH threshold value, and wherein each of said amphoteric layers is neither substantially or completely dissolvable nor permeable in aqueous solutions with a pH value between that layer's own defined lower pH threshold value and that layer's own defined upper pH threshold value, and wherein said Enteric layer is substantially or completely dissolvable or permeable in aqueous solutions only with a pH value above said defined last pH threshold value, and wherein the defined first pH threshold value lies between pH 2 and pH 9, and wherein the defined last pH threshold value lies between pH 2 and pH 9, and wherein the individual defined lower pH threshold value of each one of said one or more individual amphoteric layers is lower than the individual defined upper pH threshold value of that particular individual amphoteric layer itself, and wherein the defined upper pH threshold value of each single one of any of said layers that is enveloping another one of said layers lies above the individual defined lower pH threshold value of the layer being enveloped by said single one layer and wherein the defined upper p threshold value of each single one of any of said layers that is enveloping one of said amphoteric layers lies below the individual defined upper pH threshold value of that amphoteric layer being enveloped by said single one layer.

12. A formulation for the controlled release of one or more active ingredients in the large intestine of a mammal, characterized in that one or more active ingredients are enveloped with an Enteric layer and an amphoteric layer, wherein said amphoteric layer is enveloped by said enteric layer, and wherein said amphoteric layer is characterized by a defined lower pH threshold value and a defined upper pH threshold value, and wherein said Enteric layer is characterized by a defined last pH threshold value, said defined last pH threshold value also being referred to as the defined upper pH threshold value of said Enteric layer, and wherein said amphoteric layers is substantially or completely dissolvable or permeable in aqueous solutions with a pH value below that layer's own defined lower pH threshold value, and wherein said amphoteric layer is also substantially or completely dissolvable or permeable in aqueous solutions with a pH value above that layer's own defined upper pH threshold value, and wherein said amphoteric layer is neither substantially or completely dissolvable nor permeable in aqueous solutions with a pH value between that layer's own defined lower pH threshold value and that layer's own defined upper pH threshold value, and wherein said Enteric layer is substantially or completely dissolvable or permeable in aqueous solutions only with a pH value above said defined last pH threshold value, and wherein the defined last pH threshold value lies between pH 2 and pH 9, and wherein the individual defined lower pH threshold value of said amphoteric layer is lower than the individual defined upper pH threshold value of that amphoteric layer itself, and wherein the defined upper pH threshold value of said Enteric layer lies between the individual defined lower and the individual defined upper pH threshold value of said amphoteric layer.

13. A formulation for the controlled release of one or more active ingredients in the large intestine of a mammal, characterized in that one or more active ingredients are enveloped with an Enteric layer and one or more individual amphoteric layers, wherein said one or more individual amphoteric layers are enveloped by said enteric layer, and wherein multiple amphoteric layers are enveloped by each other, and wherein each of said individual amphoteric layers is characterized by an individual defined lower pH threshold value and an individual defined upper pH threshold value and wherein each of said individual amphoteric layers is dissolvable or permeable in aqueous solutions with a pH value below that layer's own defined lower pH threshold value, and wherein each of said amphoteric layers is also dissolvable or permeable in aqueous solutions with a pH value above that layer's own defined upper pH threshold value, and wherein each of said amphoteric layers is neither dissolvable nor permeable in aqueous solutions with a pH value between that layer's own defined lower pH threshold value and that layer's own defined upper pH threshold value, and wherein said Enteric layer is characterized by a defined last pH threshold value, said defined last pH threshold value also being referred to as the defined upper pH threshold value of said Enteric layer, and wherein said Enteric layer is dissolvable or permeable in aqueous solutions only with a pH value above said defined last pH threshold value and wherein the defined last pH threshold value lies between 2 and 9, and the individual defined lower pH threshold value of each one of said one or more individual amphoteric layers is lower than the individual defined upper pH threshold value of that particular individual amphoteric layer itself, and that the defined upper pH threshold value each single one of any of said layers that is enveloping one of said amphoteric layers lies between the individual defined lower and the individual defined upper pH threshold value of that amphoteric layer being enveloped by said single one layer.

14. A formulation according to claim 13, characterized in that the one or more active ingredients are enveloped with a Caecal layer, and the one or more active ingredients being enveloped with said Caecal layer, as well as said Caecal layer, are enveloped by the one or more amphoteric layers and the Enteric layer according to claim 13, wherein said Caecal layer is characterized by a defined lower pH threshold value, said defined lower pH threshold value of said Caecal layer also being referred to as the defined first pH threshold value, and wherein said Caecal layer is dissolvable or permeable in aqueous solutions only with a pH value below said defined lower pH threshold value of said Caecal layer and wherein the defined lower pH threshold value of the Caecal layer lies between 2 and 9, and that the defined upper pH threshold value of the amphoteric layer that is enveloping said Caecal layer lies above the defined lower pH threshold value of said Caecal layer.

15. A formulation according to claim 13, characterized in that at least one of said amphoteric layers comprises two different polymers, wherein at least one of said two different polymers is dissolvable or permeable in aqueous solutions with a pH value above a certain pH value and wherein at least another one of said two different polymers is dissolvable or permeable in aqueous solutions with a pH value below a certain pH value.

16. A formulation according to claim 14, characterized in that at least one of said amphoteric layers comprises two different polymers, wherein at least one of said two different polymers is dissolvable or permeable in aqueous solutions with a pH value above a certain pH value and wherein at least another one of said two different polymers is dissolvable or permeable in aqueous solutions with a pH value below a certain pH value.

17. A formulation according to claim 13, characterized in that at least one of said amphoteric layers comprises a polymer, wherein said polymer is dissolvable or permeable in aqueous solutions with a pH value below a certain range and wherein said polymer is also dissolvable or permeable in aqueous solutions with a pH value above a certain range but wherein said polymer is neither dissolvable nor permeable in aqueous solutions with a pH value within said certain range.

18. A formulation according to claim 14, characterized in that at least one of said amphoteric layers comprises a polymer, wherein said polymer is dissolvable or permeable in aqueous solutions with a pH value below a certain range and wherein said polymer is also dissolvable or permeable in aqueous solutions with a pH value above a certain range but wherein said polymer is neither dissolvable nor permeable in aqueous solutions with a pH value within said certain range.

19. A formulation according to claim 17, characterized in that at least one of said amphoteric layers comprises a Chitosan, wherein said chitosan comprises succinic acid groups.

20. A formulation according to claim 18, characterized in that at least one of said amphoteric layers comprises a Chitosan, wherein said chitosan comprises succinic acid groups.

21. A formulation according to claim 15, characterized in that each of said layers is considered dissolvable if it is at least dissolvable to such an extent that is necessary in order to let the surrounding aqueous solution come into contact with the next layer that is arranged further inside.

22. A formulation according to claim 16, characterized in that each of said layers is considered dissolvable if it is at least dissolvable to such an extent that is necessary in order to let the surrounding aqueous solution come into contact with the next layer that is arranged further inside.

23. A formulation according to claim 17, characterized in that each of said layers is considered dissolvable if it is at least dissolvable to such an extent that is necessary in order to let the surrounding aqueous solution come into contact with the next layer that is arranged further inside.

24. A formulation according to claim 18, characterized in that each of said layers is considered dissolvable if it is at least dissolvable to such an extent that is necessary in order to let the surrounding aqueous solution come into contact with the next layer that is arranged further inside.

25. A formulation according to claim 13, characterized in that at least one of said amphoteric layers comprises two different polymers, wherein at least one of said two different polymers is dissolvable or permeable in aqueous solutions with a pH value above a certain pH value, being about the same as the defined upper pH threshold value of said at least one amphoteric layer comprising said at least one polymer and wherein at least another one of said two different polymers is dissolvable or permeable in aqueous solutions with a pH value below a certain pH value, being about the same as the defined lower pH threshold value of said at least one amphoteric layer comprising said at least another one polymer.

26. A formulation according to claim 14, characterized in that at least one of said amphoteric layers comprises two different polymers, wherein at least one of said two different polymers is dissolvable or permeable in aqueous solutions with a pH value above a certain pH value, being about the same as the defined upper pH threshold value of said at least one amphoteric layer comprising said at least one polymer and wherein at least another one of said two different polymers is dissolvable or permeable in aqueous solutions with a pH value below a certain pH value, being about the same as the defined lower pH threshold value of said at least one amphoteric layer comprising said at least another one polymer.

27. A formulation according to claim 25, characterized in that said two different polymers are arranged effectively parallel, wherein effectively parallel means that as soon as one of said two polymers becomes dissolved, the surrounding solution can pass the other one of said two polymers and comes into contact with the next layer that is arranged further inside or with the one or more active ingredients.

28. A formulation according to claim 26, characterized in that said two different polymers are arranged effectively parallel, wherein effectively parallel means that as soon as one of said two polymers becomes dissolved, the surrounding solution can pass the other one of said two polymers and comes into contact with the next layer that is arranged further inside or with the one or more active ingredients.

29. A formulation according to claim 13, characterized in that the formulation comprises two amphoteric layers, wherein the Enteric layer envelops the second amphoteric layer and the second amphoteric layer envelops the first amphoteric layer and wherein the defined lower pH threshold value of the second amphoteric layer is lower than the defined lower pH threshold value of the first amphoteric layer and wherein the defined upper pH threshold value of the second amphoteric layer lies between the defined lower pH threshold value and the defined upper pH threshold value of the first amphoteric layer.

* * * * *